US012674199B2

(12) United States Patent
Oberstrass et al.

(10) Patent No.: US 12,674,199 B2
(45) Date of Patent: Jul. 7, 2026

(54) METHODS OF SEQUENCING NUCLEIC ACID MOLECULES

(71) Applicant: Ultima Genomics, Inc., Newark, CA (US)

(72) Inventors: Florian Oberstrass, Menlo Park, CA (US); Gilad Almogy, Palo Alto, CA (US); Linda Lee, Palo Alto, CA (US); Eliane Trepagnier, Oakland, CA (US); Geunwon Jung, San Mateo, CA (US)

(73) Assignee: Ultima Genomics, Inc., Fremont, CA (US)

( * ) Notice: Subject to any disclaimer, the term of this patent is extended or adjusted under 35 U.S.C. 154(b) by 1093 days.

(21) Appl. No.: 17/515,958

(22) Filed: Nov. 1, 2021

(65) Prior Publication Data

US 2022/0154272 A1 May 19, 2022

Related U.S. Application Data

(63) Continuation of application No. PCT/US2020/031196, filed on May 1, 2020.

(60) Provisional application No. 62/909,389, filed on Oct. 2, 2019, provisional application No. 62/842,534, filed on May 3, 2019.

(51) Int. Cl.

| | |
|---|---|
| ***C12P 19/34*** | (2006.01) |
| ***C12N 9/12*** | (2006.01) |
| ***C12Q 1/6853*** | (2018.01) |
| ***C12Q 1/6874*** | (2018.01) |

(Continued)

(52) U.S. Cl.
CPC ......... *C12Q 1/6874* (2013.01); *C12N 9/1252* (2013.01); *C12Q 1/6853* (2013.01); *C12Q 1/6876* (2013.01); *G01N 21/6428* (2013.01); *G01N 2021/6439* (2013.01)

(58) Field of Classification Search
USPC ......... 435/6.1, 6.11, 6.12, 91.1, 91.2, 91.51; 436/94, 501; 536/23.1, 24.3, 24.33, 25.3
See application file for complete search history.

(56) References Cited

U.S. PATENT DOCUMENTS

| | | | |
|---|---|---|---|
| 5,409,811 | A | 4/1995 | Tabor et al. |
| 5,674,716 | A | 10/1997 | Tabor et al. |

(Continued)

FOREIGN PATENT DOCUMENTS

| | | | |
|---|---|---|---|
| EP | 3775259 | A4 | 1/2022 |
| JP | 2012090546 | A | 5/2012 |

(Continued)

OTHER PUBLICATIONS

The definition "mutually exclusive" from Cambridge English Dictionary. Printed on Aug. 6, 2005.*

(Continued)

*Primary Examiner* — Frank W Lu
(74) *Attorney, Agent, or Firm* — Wilson Sonsini Goodrich & Rosati

(57) ABSTRACT

The present disclosure provides methods for nucleic acid sequence identification. The methods may comprise bringing a plurality of nucleic acid molecules in contact with a reaction mixture including a concentration of nucleotides that results in fractional labeling of the nucleic acid molecules. The methods may comprise starting a next reversibly-terminated, sequencing cycle prior to completion of unblocking of reversible terminators in a previous sequencing cycle.

17 Claims, 10 Drawing Sheets

Specification includes a Sequence Listing.

(51) Int. Cl.

| | |
|---|---|
| ***C12Q 1/6876*** | (2018.01) |
| ***G01N 21/64*** | (2006.01) |

(56) References Cited

U.S. PATENT DOCUMENTS

| | | | |
|---|---|---|---|
| 7,476,503 | B2 | 1/2009 | Turner et al. |
| 9,222,132 | B2 | 12/2015 | Drmanac |
| 9,453,258 | B2 | 9/2016 | Kain et al. |
| 2002/0025529 | A1 | 2/2002 | Quake et al. |
| 2006/0147935 | A1 | 7/2006 | Linnarsson |
| 2006/0172328 | A1 | 8/2006 | Buzby |
| 2010/0035253 | A1 | 2/2010 | Gordon et al. |
| 2010/0143900 | A1 | 6/2010 | Peluso et al. |
| 2011/0076679 | A1 | 3/2011 | Shin et al. |
| 2012/0264621 | A1 | 10/2012 | Hubbell et al. |
| 2013/0281306 | A1 | 10/2013 | Rigatti et al. |
| 2016/0273032 | A1 | 9/2016 | Esfandyarpour et al. |
| 2017/0044601 | A1 | 2/2017 | Crnogorac et al. |
| 2017/0275678 | A1 | 9/2017 | Sharaf et al. |
| 2017/0314064 | A1 | 11/2017 | Iyidogan et al. |
| 2018/0155698 | A1 | 6/2018 | Iyidogan et al. |
| 2018/0274024 | A1 | 9/2018 | Ju et al. |
| 2021/0079465 | A1 | 3/2021 | Almogy et al. |
| 2022/0064728 | A1 | 3/2022 | Almogy et al. |

FOREIGN PATENT DOCUMENTS

| | | | |
|---|---|---|---|
| WO | WO-2011120964 | A1 | 10/2011 |
| WO | WO-2012162429 | A2 | 11/2012 |
| WO | WO-2012166742 | A2 | 12/2012 |
| WO | WO-2012166742 | A3 | 4/2013 |
| WO | WO-2015002789 | A1 | 1/2015 |
| WO | WO-2017058953 | A1 | 4/2017 |
| WO | WO-2017084580 | A1 | 5/2017 |
| WO | WO-2018035134 | A1 | 2/2018 |
| WO | WO-2018064297 | A1 | 4/2018 |
| WO | WO-2019191003 | A1 | 10/2019 |
| WO | WO-2020227161 | A1 | 11/2020 |

OTHER PUBLICATIONS

The definition of "mutually exclusive" from Merriam-Webster Dictionary. Printed on Aug. 6, 2025.*

The definition "subsequent to" from Merriam-Webster Dictionary. Printed on Aug. 6, 2025.*

U.S. Appl. No. 17/487,804 Final Office Action dated Aug. 29, 2021.

Guo et al. An Integrated System for DNA Sequencing by Synthesis Using Novel Nucleotide Analogues. Accounts of Chemical Research 43(4):551-563 (Apr. 2010).

Guo et al. Four-color DNA sequencing with 3'-0-modified nucleotide reversible terminators and chemically cleavable fluorescent dideoxynucleotides. PNAs, vol. 105, No. 7, pp. 9145-9150 (Jul. 8, 2008).

Ju, et al., Four-color DNA sequencing by synthesis using cleavable fluorescent nucleotide reversible terminators. PNAS. Dec. 2006. 103(52):19635-19640.

U.S. Appl. No. 17/032,023 Office Action dated Sep. 21, 2023.

U.S. Appl. No. 17/487,804 Advisory Action dated Jul. 31, 2023.

U.S. Appl. No. 17/487,804 Office Action dated Nov. 16, 2023.

Co-pending U.S. Application No. 202117487804, inventors Almogy; Gilad et al., filed on Sep. 28, 2021.

EP19776285.9 Extended Search Report dated Dec. 2, 2021.

Frank, et al. Increased catalytic activity and altered fidelity of human DNA polymerase iota in the presence of manganese. J Biol Chem. Aug. 24, 2007;282(34):24689-96. Epub Jul. 2, 2007.

Knapp, D. et al. Fluorescent labeling of (oligo)nucleotides by a new fluoride cleavable linker capable of versatile attachment modes. Bioconjugate chemistry vol. 21,6 (2010): 1043-55. doi:10.1021/bc900542f.

Knapp, et al. Fluoride-Cleavable, Fluorescently Labelled Reversible Terminators: Synthesis and Use in Primer Extension. Chemistry. Mar. 1, 2011;17(10):2903-15. doi: 10.1002/chem.201001952. Epub Feb. 3, 2011.

PCT/US19/23926 International Search Report and Written Opinion dated Jul. 23, 2019.

PCT/US20/31196 International Search Report and Written Opinion dated Aug. 27, 2020.

Tabor, et al., Effect of manganese ions on the incorporation of dideoxynucleotides by bacteriophage T7 DNA polymerase and *Escherichia coli* DNA polymerase I, Proc. Natl. Acad. Sci. USA, Jun. 1989, 86:4076-80.

U.S. Appl. No. 17/487,804 Office Action dated May 9, 2022.

EP20801497.7 Extended European Search Report dated Jan. 2, 2023.

Turner, Daniel J et al. Next-generation sequencing of vertebrate experimental organisms. Mammalian genome: official journal of the International Mammalian Genome Society vol. 20,6 (2009): 327-38. doi:10.1007/s00335-009-9187-4.

U.S. Appl. No. 17/487,804 Office Action Jul. 1, 2024.

U.S. Appl. No. 17/032,023 Office Action dated Feb. 22, 2024.

U.S. Appl. No. 17/487,804 Office Action dated Feb. 22, 2024.

* cited by examiner

| | | | | |
|---|---|---|---|---|
| Image 1 signal: | 1 | 1 | 0 | 0 |
| (Image 2-Image 1) signal: | 1 | 0 | 0 | 1 |
| Base call: | A | C | G | T |

(A)

508 502 509

510 511 507

(B)

508 502 510 507

601 602 603

604 605

606 607

```
                         SEQUENCE LISTING


<160> NUMBER OF SEQ ID NOS: 1

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

tcagtacgag c                                                       11
```

METHODS OF SEQUENCING NUCLEIC ACID MOLECULES

CROSS REFERENCE

This application is a continuation of International Patent Application No. PCT/US2020/031196 filed on May 1, 2020, claims the benefit of U.S. Provisional Applications No. 62/842,534, filed May 3, 2019, and 62/909,389, filed Oct. 2, 2019, each of which applications is entirely incorporated herein by reference.

SEQUENCE LISTING

The instant application contains a Sequence Listing which has been submitted electronically in ASCII format and is hereby incorporated by reference in its entirety. Said ASCII copy, created on Dec. 9, 2021, is named 51024_733_301_SL.txt and is 598 bytes in size.

BACKGROUND

Various methods exist for identifying nucleic acid sequences. Such methods often comprise the use of fluorescently labeled nucleotides to facilitate identification of individual bases as they are incorporated into growing nucleic acid strands, such as by detecting the fluorescent labels. The bases incorporated into the growing nucleic acid strands may be terminated, for example, to prevent a second nucleotide from incorporating in the next position in the strand, corrupting a detected signal. In some instances, termination of a nucleotide may be reversed in order to incorporate subsequent bases. Alternatively or in addition, the bases incorporated into the growing nucleic acid strands may be non-terminated, and allow a second nucleotide to incorporate in the next position in the strand. Fluorescent labels may be removed prior to flowing in the subsequent batch of nucleotides to facilitate detection of the incorporation of subsequent bases. A cycle of flowing in a batch of labeled bases and reversing of terminators and/or removing dye moieties may be repeated any number of times to sequence longer strands.

SUMMARY

A nucleotide may comprise a labeling group. A nucleotide may be non-terminated.

Alternatively, a nucleotide may be reversibly terminated by modifying the nucleotide to include a blocking group, such as an azidomethyl or disulfide group, which may cap the 3'-OH group to temporarily terminate a polymerase reaction. In some instances, a blocking group may also be, or function as, a label (e.g., a fluorescent label), such that a single moiety both terminates and labels the nucleotide. Removal of such a blocking group may both reverse the termination of the nucleotide and remove the label from the nucleotide. In other instances, a fluorescent label may be removed independently of a blocking group.

Upon contacting a plurality of nucleic acid molecules (e.g., a clonal population having sequence identity) with a reaction mixture comprising nucleotides of a canonical base type, not all of the available incorporation sites configured to incorporate a nucleotide of that canonical base type may complete incorporation of the nucleotide because of, for example, reaction kinetics and/or other factors that inhibit incorporation. Such incorporation failure events may be more likely when the reaction mixture comprises nucleotides that are fluorescently labeled because the polymerase may not be as compatible with such unnatural nucleotides. Thus, interrogation of the plurality of nucleic acid molecules using that canonical base type will conclude at less than a 100% incorporation rate, and if a subsequent reaction mixture comprising nucleotides of a different canonical base type is brought into contact with the plurality of nucleic acid molecules, there will be lag phasing. In some cases, lead phasing may occur when a growing strand incorporates a nucleotide ahead of the flow. When there is lag phasing, signals from lagged strands can show up after an expected incorporation. When there is lead phasing, signals from leading strands can show up before an expected incorporation. Such lag phasing and lead phasing may eventually lead to deterioration of the sequencing quality and limit read length. Recognized herein is a need for systems and methods that address at least the above-mentioned problems.

Furthermore, the removal of fluorescent labels often results in a scar that may damage a growing nucleic acid strand. The cumulative effects of scarring on sequencing quality may be significant. Context dependence issues corresponding to variance in detected brightness based on a given sequence are also common. Furthermore, an unblocking reaction of nucleotides may be relatively slow (e.g., a minute or more), and may occur asymptotically (e.g., of a natural log) across a bulk number of strands. For example, it may take approximately 5 times as long to achieve 99.33% (e.g., $1-1/(e^5)$) completion of unblocking as it may take to achieve 63% (e.g., $1-1/e$) completion. Thus, recognized herein is a need for nucleic acid sequence identification methods that address at least the aforementioned problems, such as to alleviate the effects of scarring, phasing, and context dependence, as well as accelerate sequencing iterations. The present disclosure provides methods, systems, and kits for nucleic acid sequence identification. The methods described herein may overcome nucleic acid sequence identification while avoiding scarring, phasing, and/or context dependence issues. Similarly, the methods described herein may accelerate nucleic acid sequence identification.

In an aspect, the present disclosure provides a method for sequencing, comprising: (a) providing a plurality of nucleic acid molecules, wherein the plurality of nucleic acid molecules have sequence identity with respect to one another; (b) bringing the plurality of nucleic acid molecules in contact with a first reaction mixture comprising a first plurality of nucleotides of a same canonical base type, under conditions sufficient to incorporate the first plurality of nucleotides into a first plurality of growing strands coupled to a first subset of the plurality of nucleic acid molecules; and (c) subsequent to (b), bringing the plurality of nucleic acid molecules in contact with a second reaction mixture comprising a second plurality of nucleotides of the same canonical base type, under conditions sufficient to incorporate the second plurality of nucleotides into a second plurality of growing strands coupled to a second subset of the plurality of nucleic acid molecules, wherein the first plurality of nucleotides or the second plurality of nucleotides comprises a non-terminated nucleotide.

In some embodiments, the first reaction mixture is brought into contact with the plurality of nucleic acid molecules in (b) under a first set of reaction conditions and wherein the second reaction mixture is brought into contact with the plurality of nucleic acid molecules in (c) under a second set of reaction conditions different from the first set of reaction conditions. In some embodiments, the first set of reaction conditions and the second set of reaction conditions have one or more different conditions selected from the group consisting of temperature, pH level, salt concentration, magnesium concentration, manganese concentration, strontium concentration, nucleotide concentration, incubation time, reaction mixture volume, reaction mixture dispense velocity to the plurality of nucleic acid molecules, and crowding or viscosity reagent concentration.

In some embodiments, the first plurality of nucleotides comprises labeled nucleotides. In some embodiments, at least 5% of the first plurality of nucleotides are labeled nucleotides. In some embodiments, at least 10% of the first plurality of nucleotides are labeled nucleotides. In some embodiments, at least 20% of the first plurality of nucleotides are labeled nucleotides. In some embodiments, at least 30% of the first plurality of nucleotides are labeled nucleotides.

In some embodiments, the first plurality of nucleotides comprises unlabeled nucleotides. In some embodiments, the first plurality of nucleotides comprises labeled and unlabeled nucleotides. In some embodiments, the second plurality of nucleotides comprises unlabeled nucleotides. In some embodiments, substantially 100% of the second plurality of nucleotides are unlabeled nucleotides. In some embodiments, the second plurality of nucleotides comprises labeled nucleotides. In some embodiments, the second plurality of nucleotides comprises labeled and unlabeled nucleotides. In some embodiments, substantially 100% of nucleotides in the first reaction mixture are of the same canonical base type. In some embodiments, substantially 100% of nucleotides in the second reaction mixture are of the same canonical base type.

In some embodiments, the first plurality of nucleotides is non-terminated. In some embodiments, the second plurality of nucleotides is non-terminated. In some embodiments, the first plurality of nucleotides and the second plurality of nucleotides are non-terminated.

In some embodiments, a subset of the first plurality of nucleotides are incorporated into a growing strand of the first plurality of growing strands into nucleotide positions in the growing strand corresponding to a homopolymer sequence. In some embodiments, a subset of the second plurality of nucleotides are incorporated into a growing strand of the second plurality of growing strands into nucleotides positions in the growing strand corresponding to a homopolymer sequence. In some embodiments, the first plurality of growing strands and the second plurality of growing strands are mutually exclusive in the plurality of nucleic acid molecules. In some embodiments, the first plurality of growing strands and the second plurality of growing strands share at least one common growing strand. In some embodiments, a common growing strand of the at least one common growing strand incorporates a first nucleotide of the first plurality of nucleotides and a second nucleotide of the second plurality of nucleotides.

In some embodiments, the method further comprises bringing the plurality of nucleic acid molecules in contact with a washing solution: (i) subsequent to (b) and prior to (c), (ii) subsequent to (c), or (iii) both (i) and (ii).

In some embodiments, the first plurality of nucleotides comprise labeled nucleotides, and further comprising bringing the plurality of nucleic acid molecules in contact with a cleaving solution to cleave labels from the labeled nucleotides: (i) subsequent to (b) and prior to (c), (ii) subsequent to (c), or (iii) both (i) and (ii).

In some embodiments, the method further comprises, subsequent to (c), bringing the plurality of nucleic acid molecules in contact with a third reaction mixture comprising a third plurality of nucleotides of the same canonical base type, under conditions sufficient to incorporate the third plurality of nucleotides into a third plurality of growing strands coupled to a third subset of the plurality of nucleic acid molecules. In some embodiments, the method further comprises, in a second flow cycle, repeating (b)-(c) using a third reaction mixture in place of the first reaction mixture, wherein the third reaction mixture comprises a third plurality of nucleotides of a second same canonical base type different from the same canonical base type, and using a fourth reaction mixture in place of the second reaction mixture, wherein the fourth reaction mixture comprises a fourth plurality of nucleotides of the second same canonical base type. In some embodiments, the method further comprises, in a third flow cycle, repeating (b)-(c) using a fifth reaction mixture in place of the first reaction mixture, wherein the fifth reaction mixture comprises a fifth plurality of nucleotides of a third same canonical base type different from the same canonical base type and the second same canonical base type, and using a sixth reaction mixture in place of the second reaction mixture, wherein the sixth reaction mixture comprises a sixth plurality of nucleotides of the third same canonical base type. In some embodiments, the method further comprises, in a fourth flow cycle, repeating (b)-(c) using a seventh reaction mixture in place of the first reaction mixture, wherein the seventh reaction mixture comprises a seventh plurality of nucleotides of a fourth same canonical base type different from the same canonical base type, the second same canonical base type, and the third same canonical base type, and using an eighth reaction mixture in place of the second reaction mixture, wherein the eighth reaction mixture comprises an eighth plurality of nucleotides of the fourth same canonical base type. In some embodiments, the method further comprises, prior to the second flow cycle, bringing the plurality of nucleic acid molecules in contact with a washing solution. In some embodiments, the first plurality of nucleotides comprises labeled nucleotides, and further comprising, prior to the second flow cycle, bringing the plurality of nucleic acid molecules in contact with a cleaving solution to cleave labels from the labeled nucleotides. In some embodiments, the method further comprises, subsequent to (b) or subsequent to (c), detecting one or more signals indicative of incorporation of the first plurality of nucleotides.

In some embodiments, (c) is performed prior to or in absence of detecting one or more signals indicative of incorporation of the first plurality of nucleotides.

In another aspect, the present disclosure provides a method for sequencing, comprising: (a) providing a plurality of nucleic acid molecules, wherein the plurality of nucleic acid molecules have sequence identity with respect to one another; (b) bringing the plurality of nucleic acid molecules in contact with a first reaction mixture comprising a first plurality of nucleotides of a same canonical base type, under conditions sufficient to incorporate the first plurality of nucleotides into a first plurality of growing strands coupled to a first subset of the plurality of nucleic acid molecules; and (c) subsequent to (b), bringing the plurality of nucleic acid molecules in contact with a second reaction mixture comprising a second plurality of nucleotides of the same canonical base type, under conditions sufficient to incorporate the second plurality of nucleotides into a second plurality of growing strands coupled to a second subset of the plurality of nucleic acid molecules, wherein (c) is performed prior to or in absence of detecting one or more signals indicative of incorporation of the first plurality of nucleotides.

In some embodiments, the first reaction mixture is brought into contact with the plurality of nucleic acid molecules in (b) under a first set of reaction conditions and wherein the second reaction mixture is brought into contact with the plurality of nucleic acid molecules in (c) under a second set of reaction conditions different from the first set of reaction conditions. In some embodiments, the first set of reaction conditions and the second set of reaction conditions have one or more different conditions selected from the group consisting of temperature, pH level, salt concentration, magnesium concentration, manganese concentration, strontium concentration, nucleotide concentration, incubation time, reaction mixture volume, reaction mixture dispense velocity to the plurality of nucleic acid molecules, and crowding or viscosity reagent concentration.

In some embodiments, the first plurality of nucleotides comprises labeled nucleotides. In some embodiments, at least 5% of the first plurality of nucleotides are labeled nucleotides. In some embodiments, at least 10% of the first plurality of nucleotides are labeled nucleotides. In some embodiments, at least 20% of the first plurality of nucleotides are labeled nucleotides. In some embodiments, at least 30% of the first plurality of nucleotides are labeled nucleotides. In some embodiments, the first plurality of nucleotides comprises unlabeled nucleotides. In some embodiments, the first plurality of nucleotides comprises labeled and unlabeled nucleotides. In some embodiments, the second plurality of nucleotides comprises unlabeled nucleotides. In some embodiments, substantially 100% of the second plurality of nucleotides are unlabeled nucleotides. the second plurality of nucleotides comprises labeled nucleotides. In some embodiments, the second plurality of nucleotides comprises labeled and unlabeled nucleotides. In some embodiments, substantially 100% of nucleotides in the first reaction mixture are of the same canonical base type. In some embodiments, substantially 100% of nucleotides in the second reaction mixture are of the same canonical base type.

In some embodiments, the first plurality of nucleotides is non-terminated. In some embodiments, the second plurality of nucleotides is non-terminated. In some embodiments, the first plurality of nucleotides and the second plurality of nucleotides are non-terminated.

In some embodiments, a subset of the first plurality of nucleotides are incorporated into a growing strand of the first plurality of growing strands into nucleotide positions in the growing strand corresponding to a homopolymer sequence. In some embodiments, a subset of the second plurality of nucleotides are incorporated into a growing strand of the second plurality of growing strands into nucleotides positions in the growing strand corresponding to a homopolymer sequence. In some embodiments, the first plurality of growing strands and the second plurality of growing strands are mutually exclusive in the plurality of nucleic acid molecules. In some embodiments, the first plurality of growing strands and the second plurality of growing strands share at least one common growing strand. In some embodiments, a common growing strand of the at least one common growing strand incorporates a first nucleotide of the first plurality of nucleotides and a second nucleotide of the second plurality of nucleotides.

In some embodiments, the method further comprises bringing the plurality of nucleic acid molecules in contact with a washing solution: (i) subsequent to (b) and prior to (c), (ii) subsequent to (c), or (iii) both (i) and (ii).

In some embodiments, the first plurality of nucleotides comprises labeled nucleotides, and further comprising bringing the plurality of nucleic acid molecules in contact with a cleaving solution to cleave labels from the labeled nucleotides: (i) subsequent to (b) and prior to (c), (ii) subsequent to (c), or (iii) both (i) and (ii).

In some embodiments, the method further comprises, subsequent to (c), bringing the plurality of nucleic acid molecules in contact with a third reaction mixture comprising a third plurality of nucleotides of the same canonical base type, under conditions sufficient to incorporate the third plurality of nucleotides into a third plurality of growing strands coupled to a third subset of the plurality of nucleic acid molecules. In some embodiments, the method further comprises, in a second flow cycle, repeating (b)-(c) using a third reaction mixture in place of the first reaction mixture, wherein the third reaction mixture comprises a third plurality of nucleotides of a second same canonical base type different from the same canonical base type, and using a fourth reaction mixture in place of the second reaction mixture, wherein the fourth reaction mixture comprises a fourth plurality of nucleotides of the second same canonical base type. In some embodiments, the method further comprises, in a third flow cycle, repeating (b)-(c) using a fifth reaction mixture in place of the first reaction mixture, wherein the fifth reaction mixture comprises a fifth plurality of nucleotides of a third same canonical base type different from the same canonical base type and the second same canonical base type, and using a sixth reaction mixture in place of the second reaction mixture, wherein the sixth reaction mixture comprises a sixth plurality of nucleotides of the third same canonical base type. In some embodiments, the method further comprises, in a fourth flow cycle, repeating (b)-(c) using a seventh reaction mixture in place of the first reaction mixture, wherein the seventh reaction mixture comprises a seventh plurality of nucleotides of a fourth same canonical base type different from the same canonical base type, the second same canonical base type, and the third same canonical base type, and using an eighth reaction mixture in place of the second reaction mixture, wherein the eighth reaction mixture comprises an eighth plurality of nucleotides of the fourth same canonical base type. In some embodiments, the method further comprises, prior to the second flow cycle, bringing the plurality of nucleic acid molecules in contact with a washing solution. In some embodiments, the first plurality of nucleotides comprise labeled nucleotides, and further comprising, prior to the second flow cycle, bringing the plurality of nucleic acid molecules in contact with a cleaving solution to cleave labels from the labeled nucleotides.

In some embodiments, the method further comprises, subsequent to (c), detecting one or more signals indicative of incorporation of the first plurality of nucleotides or the second plurality of nucleotides.

In a further aspect, the present disclosure provides a method for sequencing, comprising (a) providing a plurality of nucleic acid molecules immobilized at a detection area, wherein the plurality of nucleic acid molecules have sequence homology with a template nucleic acid molecule comprising a template sequence, wherein the plurality of nucleic molecules comprises a first subset of the plurality of nucleic acid molecules coupled to first sequences and a second subset of the plurality of nucleic acid molecules coupled to second sequences; (b) bringing the plurality of nucleic acid molecules in contact with a first reaction mixture comprising a first plurality of nucleotides of a same canonical base type, under conditions sufficient to incorporate first nucleotides of the first plurality of nucleotides into the first sequences at a given open position of the template sequence across the first subset of the plurality of nucleic acid molecules; and (c) subsequent to (b), bringing the plurality of nucleic acid molecules in contact with a second reaction mixture comprising a second plurality of nucleotides of the same canonical base type, under conditions sufficient to incorporate second nucleotides from the second plurality of nucleotides into the second sequences at the given open position of the template sequence across the second subset of the plurality of nucleic acid molecules.

In some embodiments, the first reaction mixture is brought into contact with the plurality of nucleic acid molecules in (b) under a first set of reaction conditions and wherein the second reaction mixture is brought into contact with the plurality of nucleic acid molecules in (c) under a second set of reaction conditions different from the first set of reaction conditions.

In some embodiments, the first set of reaction conditions and the second set of reaction conditions have one or more different conditions selected from the group consisting of temperature, pH level, salt concentration, magnesium concentration, manganese concentration, strontium concentration, nucleotide concentration, incubation time, reaction mixture volume, reaction mixture dispense velocity to the plurality of nucleic acid molecules, and crowding or viscosity reagent concentration.

In some embodiments, the first plurality of nucleotides comprises labeled nucleotides. In some embodiments, the first plurality of nucleotides comprises labeled nucleotides. In some embodiments, at least 5% of the first plurality of nucleotides are labeled nucleotides. In some embodiments, at least 10% of the first plurality of nucleotides are labeled nucleotides. In some embodiments, at least 20% of the first plurality of nucleotides are labeled nucleotides. In some embodiments, at least 30% of the first plurality of nucleotides are labeled nucleotides. In some embodiments, the first plurality of nucleotides comprises unlabeled nucleotides. In some embodiments, the first plurality of nucleotides comprises labeled and unlabeled nucleotides. In some embodiments, the second plurality of nucleotides comprises unlabeled nucleotides. In some embodiments, substantially 100% of the second plurality of nucleotides are unlabeled nucleotides. In some embodiments, the second plurality of nucleotides comprises labeled nucleotides. In some embodiments, the second plurality of nucleotides comprises labeled and unlabeled nucleotides. In some embodiments, substantially 100% of nucleotides in the first reaction mixture are of the same canonical base type. In some embodiments, substantially 100% of nucleotides in the second reaction mixture are of the same canonical base type.

In some embodiments, the first plurality of nucleotides is non-terminated. In some embodiments, the second plurality of nucleotides is non-terminated. In some embodiments, the first plurality of nucleotides and the second plurality of nucleotides are non-terminated.

In some embodiments, a subset of the first plurality of nucleotides are incorporated into sequences of the first sequences coupled to the first subset of the plurality of nucleic acid molecules into nucleotide positions in the first sequences corresponding to a homopolymer sequence. In some embodiments, a subset of the second plurality of nucleotides are incorporated into sequences of the first sequences coupled to the first subset of the plurality of nucleic acid molecules into nucleotides positions in the growing strand corresponding to a homopolymer sequence. In some embodiments, the first subset of the plurality of nucleic acid molecules and the second subset of the plurality of nucleic acid molecules are mutually exclusive in the plurality of nucleic acid molecules. In some embodiments, the first subset of the plurality of nucleic acid molecules and the second subset of the plurality of nucleic acid molecules share at least one common nucleic acid molecule. In some embodiments, a common nucleic acid molecule of the at least one common nucleic acid molecules incorporates a first nucleotide of the first plurality of nucleotides and a second nucleotide of the second plurality of nucleotides.

In some embodiments, the method further comprises bringing the plurality of nucleic acid molecules in contact with a washing solution: (i) subsequent to (b) and prior to (c), (ii) subsequent to (c), or (iii) both (i) and (ii).

In some embodiments, the first plurality of nucleotides comprises labeled nucleotides, and further comprising bringing the plurality of nucleic acid molecules in contact with a cleaving solution to cleave labels from the labeled nucleotides: (i) subsequent to (b) and prior to (c), (ii) subsequent to (c), or (iii) both (i) and (ii).

In some embodiments, the method further comprises, subsequent to (c), bringing the plurality of nucleic acid molecules in contact with a third reaction mixture comprising a third plurality of nucleotides of the same canonical base type, under conditions sufficient to incorporate the third plurality of nucleotides into third sequences coupled to a third subset of the plurality of nucleic acid molecules. In some embodiments, the method further comprises, in a second flow cycle, repeating (b)-(c) using a third reaction mixture in place of the first reaction mixture, wherein the third reaction mixture comprises a third plurality of nucleotides of a second same canonical base type different from the same canonical base type, and using a fourth reaction mixture in place of the second reaction mixture, wherein the fourth reaction mixture comprises a fourth plurality of nucleotides of the second same canonical base type. In some embodiments, the method further comprises, in a third flow cycle, repeating (b)-(c) using a fifth reaction mixture in place of the first reaction mixture, wherein the fifth reaction mixture comprises a fifth plurality of nucleotides of a third same canonical base type different from the same canonical base type and the second same canonical base type, and using a sixth reaction mixture in place of the second reaction mixture, wherein the sixth reaction mixture comprises a sixth plurality of nucleotides of the third same canonical base type. In some embodiments, the method further comprises, in a fourth flow cycle, repeating (b)-(c) using a seventh reaction mixture in place of the first reaction mixture, wherein the seventh reaction mixture comprises a seventh plurality of nucleotides of a fourth same canonical base type different from the same canonical base type, the second same canonical base type, and the third same canonical base type, and using an eighth reaction mixture in place of the second reaction mixture, wherein the eighth reaction mixture comprises an eighth plurality of nucleotides of the fourth same canonical base type. In some embodiments, the method further comprises, prior to the second flow cycle, bringing the plurality of nucleic acid molecules in contact with a washing solution. In some embodiments, the first plurality of nucleotides comprise labeled nucleotides, and further comprising, prior to the second flow cycle, bringing the plurality of nucleic acid molecules in contact with a cleaving solution to cleave labels from the labeled nucleotides.

In some embodiments, the method further comprises, subsequent to (c), detecting one or more signals indicative of incorporation of the first plurality of nucleotides or the second plurality of nucleotides.

In a further aspect, the present disclosure provides a method for sequencing, comprising: (a) providing a plurality of nucleic acid molecules, wherein the plurality of nucleic acid molecules have sequence identity with respect to one another; (b) bringing the plurality of nucleic acid molecules in contact with a first reaction mixture comprising a first plurality of nucleotides of a same canonical base type, under conditions sufficient to incorporate the first plurality of nucleotides into a first plurality of growing strands coupled to a first subset of the plurality of nucleic acid molecules; and (c) subsequent to (b), bringing the plurality of nucleic acid molecules in contact with a second reaction mixture comprising a second plurality of nucleotides of the same canonical base type, under conditions sufficient to incorporate the second plurality of nucleotides into a second plurality of growing strands coupled to a second subset of the plurality of nucleic acid molecules, wherein, in the first reaction mixture or the second reaction mixture, nucleotides of the same canonical base type are at a greater concentration than nucleotides of another canonical base type.

In some embodiments, the first reaction mixture is brought into contact with the plurality of nucleic acid molecules in (b) under a first set of reaction conditions and wherein the second reaction mixture is brought into contact with the plurality of nucleic acid molecules in (c) under a second set of reaction conditions different from the first set of reaction conditions. In some embodiments, the first set of reaction conditions and the second set of reaction conditions have one or more different conditions selected from the group consisting of temperature, pH level, salt concentration, magnesium concentration, manganese concentration, strontium concentration, nucleotide concentration, incubation time, reaction mixture volume, reaction mixture dispense velocity to the plurality of nucleic acid molecules, and crowding or viscosity reagent concentration.

In some embodiments, the first plurality of nucleotides comprises labeled nucleotides. In some embodiments, at least 5% of the first plurality of nucleotides are labeled nucleotides. In some embodiments, at least 10% of the first plurality of nucleotides are labeled nucleotides. In some embodiments, at least 20% of the first plurality of nucleotides are labeled nucleotides. In some embodiments, at least 30% of the first plurality of nucleotides are labeled nucleotides. In some embodiments, the first plurality of nucleotides comprises unlabeled nucleotides. In some embodiments, the first plurality of nucleotides comprises labeled and unlabeled nucleotides. In some embodiments, the second plurality of nucleotides comprises unlabeled nucleotides. In some embodiments, substantially 100% of the second plurality of nucleotides are unlabeled nucleotides. In some embodiments, the second plurality of nucleotides comprises labeled nucleotides. In some embodiments, the second plurality of nucleotides comprises labeled and unlabeled nucleotides. In some embodiments, substantially 100% of nucleotides in the first reaction mixture are of the same canonical base type. In some embodiments, substantially 100% of nucleotides in the second reaction mixture are of the same canonical base type.

In some embodiments, the first plurality of nucleotides is non-terminated. In some embodiments, the second plurality of nucleotides is non-terminated. In some embodiments, the first plurality of nucleotides and the second plurality of nucleotides are non-terminated.

In some embodiments, a subset of the first plurality of nucleotides are incorporated into a growing strand of the first plurality of growing strands into nucleotide positions in the growing strand corresponding to a homopolymer sequence. In some embodiments, a subset of the second plurality of nucleotides are incorporated into a growing strand of the second plurality of growing strands into nucleotides positions in the growing strand corresponding to a homopolymer sequence. In some embodiments, the first plurality of growing strands and the second plurality of growing strands are mutually exclusive in the plurality of nucleic acid molecules. In some embodiments, the first plurality of growing strands and the second plurality of growing strands share at least one common growing strand. In some embodiments, a common growing strand of the at least one common growing strand incorporates a first nucleotide of the first plurality of nucleotides and a second nucleotide of the second plurality of nucleotides.

In some embodiments, the method further comprises bringing the plurality of nucleic acid molecules in contact with a washing solution: (i) subsequent to (b) and prior to (c), (ii) subsequent to (c), or (iii) both (i) and (ii).

In some embodiments, the first plurality of nucleotides comprise labeled nucleotides, and further comprising bringing the plurality of nucleic acid molecules in contact with a cleaving solution to cleave labels from the labeled nucleotides: (i) subsequent to (b) and prior to (c), (ii) subsequent to (c), or (iii) both (i) and (ii).

In some embodiments, the method further comprises, subsequent to (c), bringing the plurality of nucleic acid molecules in contact with a third reaction mixture comprising a third plurality of nucleotides of the same canonical base type, under conditions sufficient to incorporate the third plurality of nucleotides into a third plurality of growing strands coupled to a third subset of the plurality of nucleic acid molecules.

In some embodiments, the method further comprises, in a second flow cycle, repeating (b)-(c) using a third reaction mixture in place of the first reaction mixture, wherein the third reaction mixture comprises a third plurality of nucleotides of a second same canonical base type different from the same canonical base type, and using a fourth reaction mixture in place of the second reaction mixture, wherein the fourth reaction mixture comprises a fourth plurality of nucleotides of the second same canonical base type. In some embodiments, the method further comprises, in a third flow cycle, repeating (b)-(c) using a fifth reaction mixture in place of the first reaction mixture, wherein the fifth reaction mixture comprises a fifth plurality of nucleotides of a third same canonical base type different from the same canonical base type and the second same canonical base type, and using a sixth reaction mixture in place of the second reaction mixture, wherein the sixth reaction mixture comprises a sixth plurality of nucleotides of the third same canonical base type. In some embodiments, the method further comprises, in a fourth flow cycle, repeating (b)-(c) using a seventh reaction mixture in place of the first reaction mixture, wherein the seventh reaction mixture comprises a seventh plurality of nucleotides of a fourth same canonical base type different from the same canonical base type, the second same canonical base type, and the third same canonical base type, and using an eighth reaction mixture in place of the second reaction mixture, wherein the eighth reaction mixture comprises an eighth plurality of nucleotides of the fourth same canonical base type. In some embodiments, the method further comprises, prior to the second flow cycle, bringing the plurality of nucleic acid molecules in contact with a washing solution. In some embodiments, the first plurality of nucleotides comprises labeled nucleotides, and further comprising, prior to the second flow cycle, bringing the plurality of nucleic acid molecules in contact with a cleaving solution to cleave labels from the labeled nucleotides.

In some embodiments, the method further comprises, subsequent to (b) or subsequent to (c), detecting one or more signals indicative of incorporation of the first plurality of nucleotides. In some embodiments, (c) is performed prior to or in absence of detecting one or more signals indicative of incorporation of the first plurality of nucleotides.

In some embodiments, in the first reaction mixture and the second reaction mixture, nucleotides of the same canonical base type are at a greater concentration than nucleotides of another canonical base type. In some embodiments, in the first reaction mixture or the second reaction mixture, nucleotides of the same canonical base type are at a greater concentration than nucleotides of each other canonical base type.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 2A shows the extent of incorporation of a given nucleotide at various ion concentrations, while

DETAILED DESCRIPTION

Figure 1:
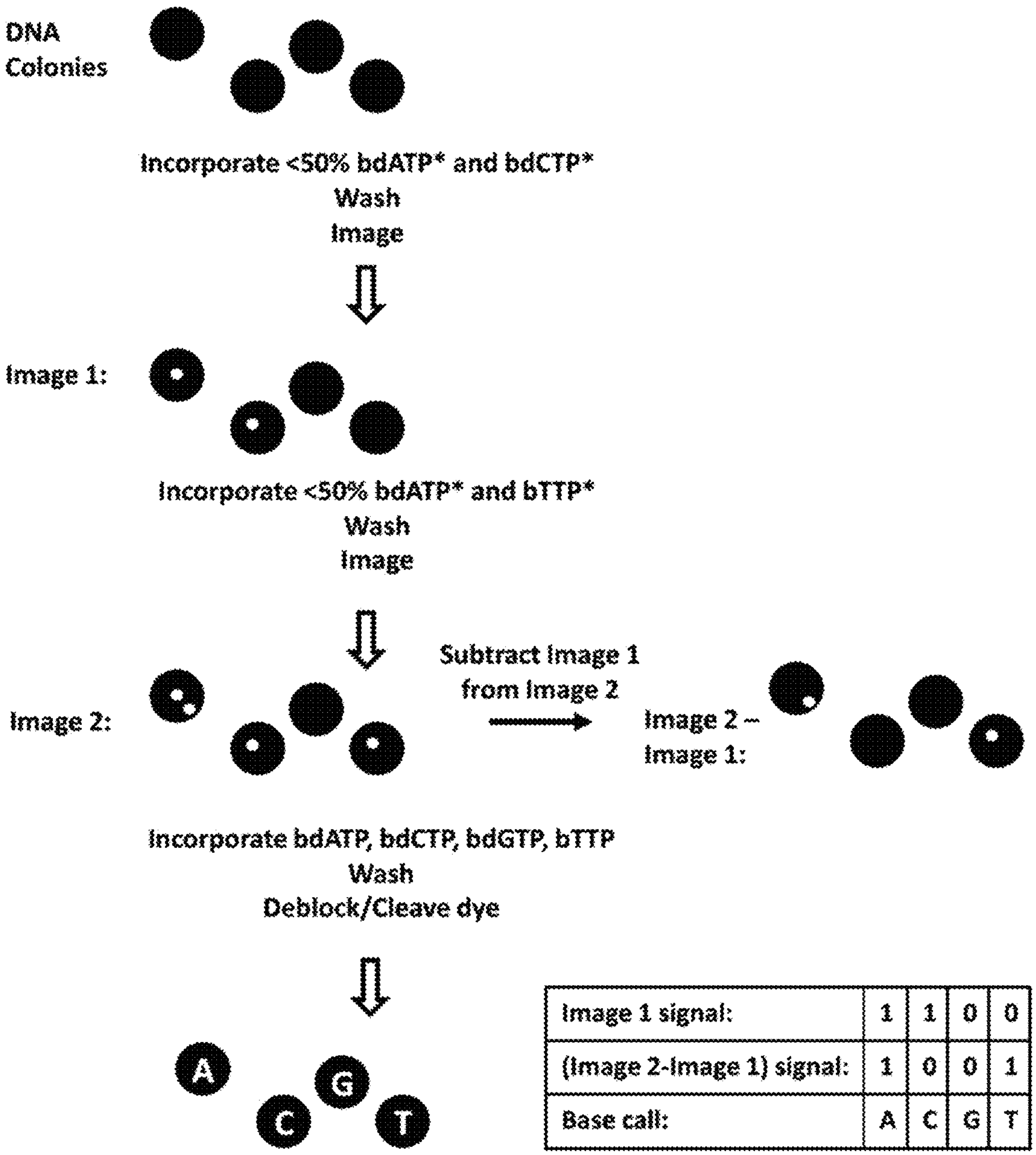
FIG. 1 schematically illustrates a multi-flow monochrome imaging method, where "b" denotes a 3'-blocking group and "*" denotes a fluorescent dye.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "amplification," as used herein, generally refers to the production of copies of a nucleic acid molecule. An amplicon may be a single-stranded or double-stranded nucleic acid molecule that is generated by an amplification procedure from a starting template nucleic acid molecule. The amplicon may comprise a nucleic acid strand, of which at least a portion is substantially identical or substantially complementary to at least a portion of the starting template. Where the starting template is a double-stranded nucleic acid molecule, an amplicon may comprise a nucleic acid strand that is substantially identical to at least a portion of one strand and is substantially complementary to at least a portion of either strand. The amplicon can be single-stranded or double-stranded irrespective of whether the initial template is single-stranded or double-stranded. Amplification of a nucleic acid may be linear, exponential, or a combination thereof. Amplification may be emulsion based or may be non-emulsion based. Non-limiting examples of nucleic acid amplification methods include reverse transcription, primer extension, polymerase chain reaction (PCR), ligase chain reaction (LCR), helicase-dependent amplification, asymmetric amplification, rolling circle amplification, and multiple displacement amplification (MDA). Where PCR is used, any form of PCR may be used, with non-limiting examples that include real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR and touchdown PCR. For example, an amplification reaction may be a polymerase chain reaction (PCR), such as an emulsion polymerase chain reaction (emPCR; e.g., PCR carried out within a microreactor such as a well or droplet). Moreover, amplification can be conducted in a reaction mixture comprising various components (e.g., a primer(s), template, nucleotides, a polymerase, buffer components, co-factors, etc.) that participate or facilitate amplification. In some cases, the reaction mixture comprises a buffer that permits context independent incorporation of nucleotides. Non-limiting examples include magnesium-ion, manganese-ion and isocitrate buffers. Additional examples of such buffers are described in Tabor, S. et al. C. C. PNAS, 1989, 86, 4076-4080 and U.S. Pat. Nos. 5,409,811 and 5,674,716, each of which is herein incorporated by reference in its entirety.

The term "denaturation," as used herein, generally refers to separation of a double-stranded molecule (e.g., DNA) into single-stranded molecules. Denaturation may be complete or partial denaturation. In partial denaturation, a single-stranded region may form in a double-stranded molecule by denaturation of the two deoxyribonucleic acid (DNA) strands flanked by double-stranded regions in DNA.

The terms "colony" or "clonal," as used herein, generally refers to a population of nucleic acid molecules for which a substantial portion of its members have substantially identical sequences. Members of a clonal population of nucleic acid molecules may have sequence homology to one another. Members of a clonal population of nucleic acid molecules need not be 100% identical or complementary, e.g., "errors" may occur during the course of synthesis such that a minority of a given population may not have sequence homology with a majority of the population. For example, at least 50% of the members of a population may be substantially identical to each other or to a reference nucleic acid molecule (i.e., a molecule of defined sequence used as a basis for a sequence comparison). At least 60%, at least 70%, at least 80%, at least 90%, at least 95%, at least 99%, or more of the members of a population may be substantially identical to each other or to the reference nucleic acid molecule. Alternatively, at least 50%, 60%, 70%, 80%, 90%, 95%, 99% or more of the members of a clonal population may be substantially complementary to the reference nucleic acid molecule (but substantially identical amongst each other). Two molecules may be considered substantially identical (or homologous) if the percent identity between the two molecules is at least 75%, 80%, 85%, 90%, 95%, 98%, 99%, 99.9% or greater. A low or insubstantial level of mixing of non-homologous nucleic acid molecules may occur during methods described herein, and thus a clonal population may contain a minority of diverse nucleic acids (e.g., less than 30%, less than 10%, less than 5%, etc.). A clonal population may be prepared using a clonal amplification method. Examples of clonal amplification methods include, but are not limited to, bridge amplification, recombinase polymerase amplification, and wildfire amplification. Clonal amplification methods may involve attaching a nucleic acid template to an adapter immobilized to a support and generating a plurality of copies of the nucleic acid template and, in some cases, complements thereof.

The terms "% sequence homology" or "percent sequence homology" or "percent sequence identity" may be used interchangeably herein with the terms "% homology," "% sequence identity," or "% identity" and may refer to the level of nucleotide sequence homology between two or more nucleotide sequences, when aligned using a sequence alignment program. For example, as used herein, 80% homology may be the same thing as 80% sequence homology determined by a defined algorithm, and accordingly a homologue of a given sequence has greater than 80% sequence homology over a length of the given sequence. The % homology may be selected from, e.g., at least 60%, at least 65%, at least 70%, at least 75%, at least 80%, at least 85%, at least 90%, at least 95%, or at least 99% or more sequence homology to a given sequence. The % homology may be in the range of, e.g., about 60% to about 70%, about 70% to about 80%, about 80% to about 85%, about 85% to about 90%, about 90% to about 95%, or about 95% to about 99%.

The term "complementary sequence," as used herein, generally refers to a sequence that hybridizes substantially and specifically under defined conditions to another sequence. Substantial hybridization may mean, for example, that more than 5%, 10%, 30%, 50% or 80% of the complementary sequence of a nucleic acid molecule hybridizes to the other sequence of another nucleic acid molecule. Hybridization between two single-stranded nucleic acid molecules may involve the formation of a double-stranded structure that is stable under defined conditions. Two single-stranded polynucleotides may be considered to be hybridized if they are bonded to each other by two or more sequentially adjacent base pairings. A substantial proportion of nucleotides in one strand of a double-stranded structure may undergo Watson-Crick base-pairing with a nucleoside on the other strand. Hybridization may also include the pairing of nucleoside analogs, such as deoxyinosine, nucleosides with 2-aminopurine bases, and the like, that may be employed to reduce the degeneracy of probes, whether or not such pairing involves formation of hydrogen bonds.

The term "immobilization," as used herein, generally refers to a substantially stable attachment, e.g., of a nucleic acid molecule to a support under defined conditions. The attachment can be by any mechanism, including, but not limited to, non-covalent bonding, ionic interactions, and covalent linkage. If a first nucleic acid molecule is hybridized to a second nucleic acid molecule immobilized on a support, then the first nucleic acid molecule may also be considered to be immobilized to the support during amplification, if amplification conditions are such that substantial amounts of the first and second nucleic acid molecules are associated or connected with each other at any or all times during amplification. For example, first and second nucleic acid molecules may be associated together by hybridization involving Watson-Crick base pairing or hydrogen bonding. In an example, amplification conditions may allow at least 50%, 80%, 90%, 95% or 99% of a first nucleic acid molecule to remain hybridized with a second nucleic acid molecule, or vice versa. A nucleic acid molecule may be considered un-immobilized or non-immobilized if it is not directly or indirectly attached to or associated with a support. In some cases, a plurality of nucleic acid molecules may be immobilized to a support and/or detection area via a plurality of primers. For example, primers may be immobilized to the support and/or detection area via, for example, non-covalent bonding, ionic interactions, and covalent linkage and the plurality of nucleic acid molecules may be hybridized or ligated to the plurality of primers.

The terms "support" or "substrate," as used herein, generally refers to any solid or semi-solid article on which reagents such as nucleic acid molecules may be immobilized. Nucleic acid molecules may be synthesized, attached, ligated, or otherwise immobilized to supports. Nucleic acid molecules may be immobilized on a substrate by any method including, but not limited to, physical adsorption, by ionic or covalent bond formation, or combinations thereof. A substrate may be 2-dimensional (e.g., a planar 2D substrate) or 3-dimensional. In some cases, a substrate may be a component of a flow cell and/or may be included within or adapted to be received by a sequencing instrument. A substrate may include a polymer, a glass, or a metallic material. Examples of substrates (or supports) include a membrane, a planar substrate, a microtiter plate, a bead (e.g., a magnetic bead), a filter, a test strip, a slide, a cover slip, and a test tube. A substrate may comprise organic polymers such as polystyrene, polyethylene, polypropylene, polyfluoroethylene, polyethyleneoxy, and polyacrylamide (e.g., polyacrylamide gel), as well as co-polymers and grafts thereof. A substrate may comprise latex or dextran. A substrate may also be inorganic, such as glass, silica, gold, controlled-pore-glass (CPG), or reverse-phase silica. The configuration of a support may be, for example, in the form of beads, spheres, particles, granules, a gel, a porous matrix, or a substrate. In some cases, a substrate may be a single solid or semi-solid article (e.g., a single particle), while in other cases a substrate may comprise a plurality of solid or semi-solid articles (e.g., a collection of particles). Substrates may be planar, substantially planar, or non-planar. Substrates may be porous or non-porous, and may have swelling or non-swelling characteristics. A substrate may be shaped to comprise one or more wells, depressions, or other containers, vessels, features, or locations. A plurality of substrates may be configured in an array at various locations. An amplification substrate (e.g., a bead) can be placed within or on another substrate (e.g., within a well of a second support). A substrate may be addressable by a robotic element (e.g., for robotic delivery of reagents or detection or one or more elements thereon), or by detection approaches, such as scanning by laser illumination and confocal or deflective light gathering. For example, a substrate may be in optical and/or physical communication with a detector. Alternatively, a substrate may be physically separated from a detector by a distance. An amplification substrate (e.g., a bead) can be placed within or on another substrate (e.g., within a well of a second support, attached to a planar substrate, etc.).

The term "detection area," as used herein, generally refers to an area of a substrate that may be addressed by detection methods. In some cases, a detection area may include the entirety of the substrate (e.g., an entire planar array, such as a planar array of a flow cell). In other cases, a detection area may include a portion of the substrate. A substrate may include multiple detection areas. In some cases, multiple detection areas may be addressable by the same detector. For example, a detector may be scanned across a substrate to address different detection areas. Different detection areas of the same substrate may have the same or different geometry, size, and other properties. A detection area may correspond to an area configured to be imaged or otherwise interrogated by an optical detection method. For example, the detection area of a substrate may correspond to an area that is irradiated with light and subsequently imaged (e.g., to detect emission of light by elements thereon). A detection area may have any useful size or geometry. In some cases, a detection area may be circular. In other cases, a detection area may be rectangular. A detection area may include areas where a detector configured to interrogate the area may have differing sensitivities. Accordingly, in some cases a detection area may be calibrated for dark spots and areas of variable sensitivity.

The term "primer" or "primer molecule," as used herein, generally refers to a nucleic acid molecule (e.g., polynucleotide) which is complementary to a portion of a template nucleic acid molecule. For example, a primer may be complementary to a portion of a strand of a template nucleic acid molecule. A primer may exhibit sequence identity or homology or complementarity to a template nucleic acid molecule. The complementarity or homology or sequence identity between the primer and the template nucleic acid molecule may be limited. The homology or sequence identity or complementarity between the primer and a template nucleic acid molecule may be based on the length of the primer. For example, if the primer length is about 20 nucleotide bases, it may contain 10 or more contiguous nucleotide bases complementary to the template nucleic acid molecule. The length of the primer may be, for example, between 8 and 50 nucleotide bases. In some cases, the length of a primer may be more than 2 nucleotide bases, such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 42, 44, 46, 48, 50, or more nucleotide bases. In some cases, the length of a primer may be less than 50 nucleotide bases, such as no more than 48, 46, 44, 42, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, or 3 nucleotide bases. The primer may be a strand of nucleic acid that serves as a starting point for nucleic acid synthesis, such as a primer extension reaction which may be a component of a nucleic acid reaction (e.g., nucleic acid amplification reaction such as PCR). A primer may hybridize to a template strand and nucleotides (e.g., canonical nucleotides or nucleotide analogs) may then be added to the end(s) of a primer, sometimes with the aid of a polymerizing enzyme such as a polymerase. Thus, during replication of a DNA sample, an enzyme that catalyzes replication may start replication at the 3'-end of a primer attached to the DNA sample and copy the opposite strand. A primer (e.g., oligonucleotide) may have one or more functional groups that may be used to couple the primer to a support and/or detection area (e.g., as described herein).

The term "primer extension reaction," as used herein, generally refers to binding of a primer to a strand of a template nucleic acid molecule, followed by elongation of the primer. It may also include denaturing of a double-stranded nucleic acid molecule and the binding of a primer to either one or both denatured strands of the double-stranded nucleic acid molecule, followed by elongation of one or more primers. Primer extension reactions may be used to incorporate nucleotides or nucleotide analogs to a primer in template-directed fashion by using enzymes (e.g., polymerizing enzymes).

The term "polymerizing enzyme," "polymerase," or "polymerization enzyme," as used herein, generally refers to a substance catalyzing a polymerization reaction. A polymerizing enzyme may be used to extend a nucleic acid primer paired with a template strand by incorporation of nucleotides or nucleotide analogs. A polymerizing enzyme may add a new strand of DNA by extending the 3' end of an existing nucleotide chain, adding new nucleotides matched to the template strand one at a time via the creation of phosphodiester bonds. A polymerizing enzyme may be a polymerase such as a nucleic acid polymerase. A polymerase may be naturally occurring or synthesized. A polymerase may have relatively high processivity, namely the capability of the polymerase to consecutively incorporate nucleotides into a nucleic acid template without releasing the nucleic acid template. A polymerizing enzyme may be a transcriptase. Examples of polymerases include, but are not limited to, a DNA polymerase, an RNA polymerase, a thermostable polymerase, a wild-type polymerase, a modified polymerase, *E. coli* DNA polymerase I, T7 DNA polymerase, bacteriophage T4 DNA polymerase, Φ29 (phi29) DNA polymerase, Taq polymerase, Tth polymerase, Tli polymerase, Pfu polymerase, Pwo polymerase, VENT polymerase, DEEPVENT polymerase, EXTaq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. A polymerase may be a single subunit polymerase.

The term "nucleotide," as used herein, generally refers to a substance including a base (e.g., a nucleobase), sugar moiety, and phosphate moiety. A nucleotide may comprise a free base with attached phosphate groups. A substance including a base with three attached phosphate groups may be referred to as a nucleoside triphosphate. When a nucleotide is being added to a growing nucleic acid molecule strand, the formation of a phosphodiester bond between the proximal phosphate of the nucleotide to the growing chain may be accompanied by hydrolysis of a high-energy phosphate bond with release of the two distal phosphates as a pyrophosphate. A nucleotide may be a standard (e.g., canonical) nucleotide, or a nucleotide analog (e.g., modified or engineered nucleotide, or a non-canonical nucleotide). A nucleotide may be naturally occurring or non-naturally occurring (e.g., a modified or engineered nucleotide).

A nucleotide analog may be a nonstandard or non-canonical nucleotide. A nucleotide analog may be a modified or engineered nucleotide (e.g., a nucleotide having a fluorophore). A nucleotide analog may be a naturally occurring nucleotide or a non-naturally occurring nucleotide. For example, a nucleotide analog is derived from and/or include structural similarities to a canonical nucleotide such as adenine (A), thymine (T), cytosine (C), uracil (U), or guanine (G). A nucleotide analog may comprise one or more differences or modifications relative to a natural nucleotide. Examples of nucleotide analogs include inosine, diaminopurine, 5-fluorouracil, 5-bromouracil, 5-chlorouracil, 5-iodouracil, hypoxanthine, xanthine, deazaxanthine, deazaguanine, isocytosine, isoguanine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine, ethynyl nucleotide bases, 1-propynyl nucleotide bases, azido nucleotide bases, phosphoroselenoate nucleic acids, and modified versions thereof (e.g., by oxidation, reduction, and/or addition of a substituent such as an alkyl, hydroxyalkyl, hydroxyl, or halogen moiety). Nucleic acid molecules (e.g., polynucleotides, double-stranded nucleic acid molecules, single-stranded nucleic acid molecules, primers, adapters, etc.) may be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety, or phosphate backbone. In some cases, a nucleotide may include a modification in its phosphate moiety, including a modification to a triphosphate moiety. Additional, non-limiting examples of modifications include phosphate chains of greater length (e.g., a phosphate chain having, 4, 5, 6, 7, 8, 9, 10 or more phosphate moieties), modifications with thiol moieties (e.g., alpha-thio triphosphate and beta-thiotriphosphates), and modifications with selenium moieties (e.g., phosphoroselenoate nucleic acids). A nucleotide or nucleotide analog may comprise a sugar selected from the group consisting of ribose, deoxyribose, and modified versions thereof (e.g., by oxidation, reduction, and/or addition of a substituent such as an alkyl, hydroxyalkyl, hydroxyl, or halogen moiety). A nucleotide analog may also comprise a modified linker moiety (e.g., in lieu of a phosphate moiety). Nucleotide analogs may also contain amine-modified groups, such as aminoallyl-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure may provide, for example, higher density in bits per cubic mm, higher safety (resistant to accidental or purposeful synthesis of natural toxins), easier discrimination in photo-programmed polymerases, and/or lower secondary structure. Nucleotide analogs may be capable of reacting or bonding with detectable moieties for nucleotide detection. In some cases, a nucleotide analog may comprise a reversible terminator and/or a fluorescent label.

The terms "free nucleotide" or "free nucleotide analog," as used herein, generally refer to a nucleotide analog that is not coupled to an additional nucleotide or nucleotide analog. Free nucleotide analogs may be incorporated into growing nucleic acid chains by primer extension reactions (e.g., as described herein).

The term "reversible terminator," as used herein, generally refers to a moiety of a nucleotide analog that is capable of terminating primer extension reversibly. Nucleotide analogs comprising reversible terminators are accepted by polymerases and incorporated into growing nucleic acid sequences analogously to non-reversibly terminated nucleotides and nucleotide analogs. Following incorporation of a nucleotide analog comprising a reversible terminator into a nucleic acid strand, the reversible terminator may be removed to permit further extension of the nucleic acid strand. A reversible terminator may comprise a blocking or capping group that is attached to the 3'-oxygen atom of a sugar moiety (e.g., a pentose) of a nucleotide or nucleotide analog. Such moieties are referred to as 3'-O-blocked reversible terminators. Examples of 3'-O-blocked reversible terminators include, for example, 3'-$ONH_2$ reversible terminators, 3'-O-allyl reversible terminators, and 3'-O-azidomethyl reversible terminators. Alternatively, a reversible terminator may comprise a blocking group in a linker (e.g., a cleavable linker) and/or dye moiety of a nucleotide analog. Such moieties are referred to as 3'-unblocked reversible terminators. 3'-unblocked reversible terminators may be attached to both the base of the nucleotide analog as well as a fluorescing group (e.g., label, as described herein). Examples of 3'-unblocked reversible terminators include, for example, the "virtual terminator" developed by Helicos BioSciences Corp. and the "lightning terminator" developed by Michael L. Metzker and co-workers. Cleavage of a reversible terminator may be achieved by, for example, irradiating a nucleic acid molecule including the reversible terminator.

The term "label," as used herein, generally refers to a moiety that is capable of coupling with a species, such as, for example a nucleotide analog. A label may include an affinity moiety. In some cases, a label may be a detectable label that emits a signal (or reduces an already emitted signal) that can be detected. In some cases, such a signal may be indicative of incorporation of one or more nucleotides or nucleotide analogs. In some cases, a label may be coupled to a nucleotide or nucleotide analog, which nucleotide or nucleotide analog may be used in a primer extension reaction. In some cases, the label may be coupled to a nucleotide analog after a primer extension reaction. The label, in some cases, may be reactive specifically with a nucleotide or nucleotide analog. Coupling may be covalent or non-covalent (e.g., via ionic interactions, Van der Waals forces, etc.). In some cases, coupling may be via a linker, which may be cleavable, such as photo-cleavable (e.g., cleavable under ultra-violet light), chemically-cleavable (e.g., via a reducing agent, such as dithiothreitol (DTT), tris(2-carboxyethyl)phosphine (TCEP), tris(hydroxypropyl)phosphine (THP) or enzymatically cleavable (e.g., via an esterase, lipase, peptidase or protease). In some cases, the label may be luminescent; that is, fluorescent or phosphorescent. Labels may be quencher molecules. The term "quencher," as used herein refers to a molecule that can reduce an emitted signal. For example, a template nucleic acid molecule may be designed to emit a detectable signal. Incorporation of a nucleotide or nucleotide analog comprising a quencher can reduce or eliminate the signal, which reduction or elimination is then detected. In some cases, as described elsewhere herein, labelling with a quencher can occur after nucleotide or nucleotide analog incorporation. Non-limiting examples of dyes include SYBR green, SYBR blue, DAPI, propidium iodine, Hoechst, SYBR gold, ethidium bromide, acridine, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), VIC, 5- (or 6-) iodoacetamidofluorescein, 5-{[2(and 3)-5-(Acetylmercapto)-succinyl]amino} fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores, Black Hole Quencher Dyes (Biosearch Technologies) such as BH1-0, BHQ-1, BHQ-3, BHQ-10); QSY Dye fluorescent quenchers (from Molecular Probes/Invitrogen) such QSY7, QSY9, QSY21, QSY35, and other quenchers such as Dabcyl and Dabsyl; Cy5Q and Cy7Q and Dark Cyanine dyes (GE Healthcare); Dy-Quenchers (Dyomics), such as DYQ-660 and DYQ-661; and ATTO fluorescent quenchers (ATTO-TEC GmbH), such as ATTO 540Q, 580Q, 612Q. In some cases, the label may be a type that does not self-quench or exhibit proximity quenching. Non-limiting examples of a label type that does not self-quench or exhibit proximity quenching include Bimane derivatives such as Monobromobimane.

The term "proximity quenching," as used herein, generally refers to a phenomenon where one or more dyes near each other may exhibit lower fluorescence as compared to the fluorescence they exhibit individually. In some cases, the dye may be subject to proximity quenching wherein the donor dye and acceptor dye are within 1 nanometer (nm) to 50 nm of each other.

The term "detector," as used herein, generally refers to a device that is capable of detecting a signal, such as a signal indicative of the presence or absence of an incorporated nucleotide or nucleotide analog. A detector may include optical and/or electronic components that may detect signals. Non-limiting examples of detection methods involving a detector include optical detection, spectroscopic detection, electrostatic detection, and electrochemical detection. Optical detection methods include, but are not limited to, fluorimetry and UV-vis light absorbance. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis. Electrochemical detection methods include, but are not limited to, electrochemical detection of amplified product after high-performance liquid chromatography separation of the amplified products.

The term "sequencing," as used herein, generally refers to a process for generating or identifying a sequence of a biological molecule, such as a nucleic acid molecule or a polypeptide. Such a sequence may be a nucleic acid sequence, which may include a sequence of nucleic acid bases (e.g., nucleobases). Sequencing may be, for example, single molecule sequencing, sequencing by synthesis, sequencing by hybridization, or sequencing by ligation. Sequencing may be performed using template nucleic acid molecules immobilized on a support, such as a flow cell or one or more beads (e.g., as described herein). A sequencing assay may yield one or more sequencing reads corresponding to one or more template nucleic acid molecules.

The term "read," as used herein, generally refers to a nucleic acid sequence, such as a sequencing read. A sequencing read may be an inferred sequence of nucleic acid bases (e.g., nucleotides) or base pairs obtained via a nucleic acid sequencing assay. A sequencing read may be generated by a nucleic acid sequencer, such as a massively parallel array sequencer (e.g., Illumina or Pacific Biosciences of California). A sequencing read may correspond to a portion, or in some cases all, of a genome of a subject. A sequencing read may be part of a collection of sequencing reads, which may be combined through, for example, alignment (e.g., to a reference genome), to yield a sequence of a genome of a subject.

Methods of Analyzing Nucleic Acid Sequences

The present disclosure provides methods, systems, and kits for analyzing nucleic acid sequences. A method for nucleic acid sequence identification may comprise providing a substrate comprising a plurality of nucleic acid molecules immobilized at or adjacent to a detection area. The plurality of nucleic acid molecules may have sequence homology with a template (e.g., target) nucleic acid molecule. The plurality of nucleic acid molecules may be brought into contact with a first reaction mixture and, subsequently, a second reaction mixture. The first and second reaction mixtures may comprise various combinations of labeled and unlabeled nucleotides (e.g., as described herein). Signals detected from the detection area may correspond to nucleotides of the first and/or second reaction mixtures. Such signals may be used to identify one or more nucleic acid bases of the plurality of nucleic acid molecules. In some cases, signals may be detected after bringing the plurality of nucleic acid molecules in contact with the first reaction mixture (e.g., before or after a wash flow and/or cleavage flow, as described herein). In some cases, signals may also or alternatively be detected after bringing the plurality of nucleic acid molecules in contact with the second reaction mixture (e.g., before or after a wash flow and/or cleavage flow, as described herein). Additional reaction mixtures comprising various combinations of labeled and unlabeled nucleotides may also be used. Signals that correspond to nucleotides from the first reaction mixture and signals that correspond to nucleotides from the second reaction mixture (and also optionally signals that correspond to nucleotides from additional reaction mixtures) may each correspond to the same base position(s) in a sequence of the template nucleic acid molecule. In some instances, a combination of signals that correspond to nucleotides from the first reaction mixture and signals that correspond to nucleotides from the second reaction mixture (and also optionally signals that correspond to nucleotides from additional reaction mixtures) may be used to identify nucleic acid base(s) at such same base position(s) in the sequence of the template nucleic acid molecule.

Sequencing schemes or approaches of the present disclosure may employ multiple flows per sequencing read cycle. A given flow may comprise, for example, a reaction mixture comprising a plurality of nucleotides, such as a plurality of labeled nucleotides. The plurality of nucleotides may comprise one or more different canonical types of nucleotides, at least a subset of which may comprise labels (e.g., as described herein). For example, a given flow may comprise a reaction mixture comprising a first plurality of nucleotides and a second plurality of nucleotides. The first plurality of nucleotides and the second plurality of nucleotides may be of the same or a different canonical type. The first and/or second plurality of nucleotides may be labeled (e.g., with fluorescent labels). Alternatively, the first and/or second plurality of nucleotides may be unlabeled. (e.g., without fluorescent labels) The first and/or second plurality of nucleotides may also or alternatively be reversibly terminated (e.g., as described herein). The plurality of nucleotides of a given flow can be contacted with a plurality of nucleic acid molecules (e.g., a plurality of target nucleic acid molecules immobilized to a substrate, such as at a detection area) under conditions sufficient for at least a subset of the plurality of nucleotides to become incorporated into sequences coupled to the plurality of nucleic acid molecules (e.g., growing strands). The sequences coupled to the plurality of nucleic acid molecules may be at least partially complementary sequences. Additional flows may also be employed. For example, a wash flow (e.g., a solution comprising a buffer) may be used to remove nucleotides of a plurality of nucleotides of a reaction mixture of a reaction mixture flow that are not incorporated (e.g., as described herein). A wash flow may comprise one or more reagents, such as a cleavage reagent that may be used to remove a label and/or reversible terminator from an incorporated nucleotide. Alternatively or in addition, a cleavage flow (e.g., a solution comprising a cleavage reagent) may be used to remove a label and/or reversible terminator from an incorporated nucleotide. In some cases, multiple different cleavage reagents may be used (e.g., to remove one or more different components, such as one or more different labels).

A cycle may comprise a plurality of flows. A cycle may be a process in which at least a reaction mixture (e.g., nucleotide) flow and a wash flow are provided to a plurality of nucleic acid molecules (e.g., a plurality of target nucleic acid molecules immobilized to a substrate, such as a detection area). A cycle may also comprise one or more cleavage flows. A cycle may comprise one or more reaction mixture flows, each of which may be followed by a wash flow. For example, a cycle may comprise a first reaction mixture flow, a first wash flow, a second reaction mixture flow, and a second wash flow.

In an example, the first reaction mixture flow may comprise at least a first plurality of nucleotides and a second plurality of nucleotides, and the second reaction mixture may comprise at least a third plurality of nucleotides and a fourth plurality of nucleotides, where the first plurality of nucleotides, second plurality of nucleotides, third plurality of nucleotides, and fourth plurality of nucleotides are of different canonical types. In another example, the first reaction mixture flow may comprise at least a first plurality of nucleotides, a second plurality of nucleotides, and a third plurality of nucleotides, and the second reaction mixture flow may comprise a fourth plurality of nucleotides, where the first plurality of nucleotides, second plurality of nucleotides, third plurality of nucleotides, and fourth plurality of nucleotides are of different canonical types. In another example, the first reaction mixture flow may comprise at least a first plurality of nucleotides, and the second reaction mixture flow may comprise a second plurality of nucleotides, a third plurality of nucleotides, and a fourth plurality of nucleotides, where the first plurality of nucleotides, second plurality of nucleotides, third plurality of nucleotides, and fourth plurality of nucleotides are of different canonical types.

Nucleotides of a given reaction mixture flow may be labeled or unlabeled. Accordingly, in any of the preceding examples, at least a subset of a plurality of nucleotides may be labeled. Accordingly, in some instances, at least a subset of a plurality of nucleotides may be unlabeled.

In an example, the first reaction mixture flow may comprise at least a first plurality of nucleotides and a second plurality of nucleotides, where the first plurality of nucleotides comprises labeled nucleotides of a canonical base type and the second plurality of nucleotides comprises unlabeled nucleotides of the same canonical base type, and the second reaction mixture may comprise at least a third plurality of nucleotides, where the third plurality of nucleotides comprises nucleotides of the same canonical base type, which may be labeled or unlabeled. In some cases, the second reaction mixture may comprise at least a third plurality of nucleotides and a fourth plurality of nucleotides, wherein the third plurality of nucleotides comprises labeled nucleotides of the same canonical base type and the fourth plurality of nucleotides comprises unlabeled nucleotides of the same canonical base type.

In another example, the first reaction mixture flow may comprise at least a first plurality of nucleotides and a second plurality of nucleotides, and the second reaction mixture may comprise at least a third plurality of nucleotides and a fourth plurality of nucleotides, where the first plurality of nucleotides, second plurality of nucleotides, third plurality of nucleotides, and fourth plurality of nucleotides are of different canonical types, and where at least a subset of the first plurality of nucleotides and at least a subset of the second plurality of nucleotides are labeled. In another example, the first reaction mixture flow may comprise at least a first plurality of nucleotides, a second plurality of nucleotides, and a third plurality of nucleotides, and the second reaction mixture flow may comprise a fourth plurality of nucleotides, where the first plurality of nucleotides, second plurality of nucleotides, third plurality of nucleotides, and fourth plurality of nucleotides are of different canonical types, and wherein at least a subset of each of the first plurality of nucleotides, the second plurality of nucleotides, and the third plurality of nucleotides are labeled. In another example, the first reaction mixture flow may comprise at least a first plurality of nucleotides, a second plurality of nucleotides, a third plurality of nucleotides, and a fourth plurality of nucleotides, and the second reaction mixture flow may comprise a fifth plurality of nucleotides, a sixth plurality of nucleotides, a seventh plurality of nucleotides, and an eighth plurality of nucleotides, where the first plurality of nucleotides, second plurality of nucleotides, third plurality of nucleotides, and fourth plurality of nucleotides are of different canonical types; the first plurality of nucleotides is of a same canonical type as the fifth plurality of nucleotides; the second plurality of nucleotides is of a same canonical type as the sixth plurality of nucleotides; the third plurality of nucleotides is of a same canonical type as the seventh plurality of nucleotides; the fourth plurality of nucleotides is of a same canonical type as the eighth plurality of nucleotides; at least a subset of each of the first plurality of nucleotides, the second plurality of nucleotides, the third plurality of nucleotides, and the fourth plurality of nucleotides are labeled; and no nucleotides of the fifth plurality of nucleotides, sixth plurality of nucleotides, seventh plurality of nucleotides, or eighth plurality of nucleotides are labeled. Additional examples are described elsewhere herein.

The plurality of nucleic acid molecules (e.g., target nucleic acid molecules) immobilized to a substrate (e.g., at a detection area) may be coupled to a plurality of sequences. The plurality of sequences may comprise, for example, primer sequences. For example, the plurality of nucleic acid molecules may be hybridized to a plurality of sequences comprising a plurality of primer molecules. The plurality of primer molecules may comprise sequences complementary to sequences of the plurality of nucleic acid molecules. The plurality of sequences coupled to the plurality of nucleic acid molecules may comprise a plurality of incorporation sites (e.g., sites where a nucleotide may be incorporated). For example, a terminus of each sequence of the plurality of sequences coupled to the plurality of nucleic acid molecules may comprise an incorporation site at a given point in time (e.g., prior to bringing the plurality of nucleic acid molecules in contact with a first reaction mixture (e.g., as described herein)). An incorporation site of a sequence of the plurality of sequences coupled to the plurality of nucleic acid molecules may be considered available for incorporation of a nucleotide (e.g., a nucleotide that is complementary to a nucleotide of the nucleic acid molecule of the plurality of nucleic acid molecules to which the sequence is coupled). In some instances, a terminus of a sequence of the plurality of sequences coupled to the plurality of nucleic acid molecules may be blocked. For example, the terminus may comprise a nucleotide comprising a reversible terminator. Such a nucleotide may have become incorporated into the sequence during contact between the plurality of nucleic acid molecules and a reaction mixture (e.g., during a reaction mixture flow). A reversible terminator of a sequence of the plurality of sequences may be completely or partially removed or otherwise inactivated to facilitate incorporation of one or more additional nucleotides into the sequence (e.g., via cleavage of all or a portion of the reversible terminator, such as during a cleavage flow).

Bringing a plurality of nucleic acid molecules (e.g., as described herein) in contact with a first reaction mixture comprising a plurality of nucleotides may or may not result in incorporation of nucleotides of the plurality of nucleotides at 100% of the available incorporation sites. For example, the plurality of nucleotides may comprise nucleotides of limited types such that the first reaction mixture does not provide a nucleotide of an appropriate type for incorporation at a given incorporation site. Alternatively or in addition, the rate of the incorporation reaction for a given nucleotide of the plurality of nucleotides may be such that 100% incorporation is not achieved in a given time frame (e.g., the duration of contact between the plurality of nucleic acid molecules and the first reaction mixture). For example, after a first flow in a sequencing read cycle (e.g., bringing a plurality of nucleic acid molecules in contact with a first reaction mixture), the available incorporation sites may have only been fractionally occupied by nucleotides incorporated from the first flow. Such fractional occupancy may be at least about 1%, 5%, 10%, 20%, 30%, 40%, 50%, 60%, 70%, 80%, 90%, 99% or more, but less than full occupancy. The fractional occupancy may apply to the total number of incorporation sites or to the total number of incorporation sites suitable for incorporation of a given nucleotide. For example, the fractional occupancy for incorporation sites suitable for incorporation of a given nucleotide (e.g., dATP, dCTP, dGTP, or dTTP) may be at least about 1%, 5%, 10%, 20%, 30%, 40%, 50%, 60%, 70%, 80%, 90%, 99% or more, but less than full occupancy. A next, or other subsequent, flow (e.g., second flow, third flow, fourth flow, etc.) in the sequencing read cycle may allow at least a subset of the remaining available sites to be occupied by nucleotides from the next, or other subsequent, flow. This may be repeated as necessary to bring all incorporation sites in phase (e.g., to incorporate a single nucleotide at each available incorporation site such that (i) the plurality of sequences coupled to the plurality of nucleic acid molecules grow the same length (e.g., a single nucleotide) over a same time period (e.g., during a reaction cycle) and/or (ii) the next incorporation site can incorporate the appropriate nucleotide during subsequent flow(s)).

For example, a first flow comprising a first reaction mixture may result in a small percentage (for example, less than about 10%, such as about 5%) of all available sites (e.g., total incorporation sites or total incorporation sites suitable for incorporation of a given nucleotide) being occupied by nucleotides of the first reaction mixture, leaving a large percentage (for example, at least about 90%, such as about 95%) unoccupied. A second flow comprising a second reaction mixture after the first flow may occupy a remainder (i.e., about 95%) of the available sites that were not occupied from the first flow. In some cases, the second flow may occupy a subset of the remainder from the first flow (for example, about 20%, leaving about 75% of the site unoccupied by nucleotides). At least a portion of the subset may be occupied by another subsequent flow. This may be repeated until all or substantially all of the sites are occupied by nucleotides. In another example, a first flow comprising a first reaction mixture may result in a large percentage (for example, at least about 90%, such as about 95%) of all available sites (e.g., total incorporation sites or total incorporation sites suitable for incorporation of a given nucleotide) being occupied by nucleotides of the first reaction mixture, leaving a small percentage (for example, less than about 10%, such as about 5%) unoccupied. A second flow comprising a second reaction mixture after the first flow may occupy a remainder (i.e., about 5%) of the available sites that were not occupied from the first flow. In some cases, the second flow may occupy a subset of the remainder from the first flow (for example, about 4%, leaving about 1% of the site unoccupied by nucleotides). At least a portion of the subset may be occupied by another subsequent flow. This may be repeated until all or substantially all of the sites are occupied by nucleotides.

A method of identifying a nucleic acid sequence may comprise providing a plurality of nucleic acid molecules (e.g., as described herein). The plurality of nucleic acid molecules may be a colony or clonal population, or part of a colony or clonal population, having sequence homology to a template nucleic acid molecule. The plurality of nucleic acid molecules may be a plurality of colonies or clonal populations, where each colony has sequence homology to a distinct template nucleic acid molecule (which may be the same or different across distinct colonies). The plurality of nucleic acid molecules may be immobilized at or adjacent to a detection area (e.g., in a flow cell). For example, the plurality of nucleic acid molecules may be immobilized by a plurality of primers. One or more colonies may be immobilized to one or more supports.

The plurality of nucleic acid molecules, or a subset thereof, may be brought into contact with a first reaction mixture comprising a first plurality of nucleotides (e.g., free nucleotides) under conditions sufficient to incorporate first nucleotides of the first plurality of nucleotides into first sequences coupled (e.g., hybridized) to a first subset of the plurality of nucleic acid molecules. The first subset may be less than all of the plurality of nucleic acid molecules. For example, the first subset may be at most about 99%, 98%, 97%, 96%, 95%, 94%, 93%, 92%, 91%, 90%, 85%, 80%, 75%, 70%, 65%, 60%, 55%, 50%, 40%, 30%, 25%, 20%, 15%, 10%, 5% or less of the plurality of nucleic acid molecules. Alternatively or in addition, the first subset may be at least about 5%, 10%, 15%, 20%, 25%, 30%, 40%, 50%, 55%, 60%, 65%, 70%, 75%, 80%, 85%, 90%, 91%, 92%, 93%, 94%, 95%, 96%, 97%, 98%, 99% or more but less than 100% of the plurality of nucleic acid molecules. The first plurality of nucleotides may be incorporated into the first sequences at a given open position (e.g., incorporation site) across the first subset of the plurality of nucleic acid molecules. The first plurality of nucleotides may be labeled (e.g., as described herein). Alternatively or in addition, the first plurality of nucleotides may be unlabeled. The first plurality of nucleotides may be reversibly terminated (e.g., as described herein). Alternatively or in addition, the first plurality of nucleotide may not be terminated. At the end of this operation (e.g., after the duration of contact between the plurality of nucleic acid molecules and the first reaction mixture), the plurality of nucleic acid molecules may comprise (i) the first subset of the plurality of nucleic acid molecules, in which the first nucleotides of the first plurality of nucleotides have been incorporated at the given open positions, and (ii) a second subset of the plurality of nucleic acid molecules, different from the first subset, for which incorporation sites remain open for incorporation. That is, subsequent to a first flow of the first reaction mixture, only a fraction of the available incorporation sites may have incorporated nucleotides from the first reaction mixture. The given open position of a nucleic acid molecule in a colony, whether in the first subset or second subset of the plurality of nucleic acid molecules, may be configured to incorporate the same or different canonical base type nucleotide.

The plurality of nucleic acid molecules, or a subset thereof, may then be brought into contact with a second reaction mixture comprising a second plurality of nucleotides under conditions sufficient to incorporate second nucleotides of the second plurality of nucleotides into second sequences coupled (e.g., hybridized) to the second subset of the plurality of nucleic acid molecules. The second nucleotides of the second plurality of nucleotides may be incorporated into the second sequences at a given open position across the second subset of the plurality of nucleic acid molecules. In some cases, the second plurality of nucleotides may be unlabeled. In other cases, the second plurality of nucleotides may be labeled. In yet other cases, the second plurality of nucleotides may be a mixture of labeled and unlabeled nucleotides. The second plurality of nucleotides may be reversibly terminated (e.g., as described herein). Alternatively or in addition, the second plurality of nucleotide may not be terminated. At the end of this operation (e.g., after the duration of contact between the plurality of nucleic acid molecules and the second reaction mixture), the plurality of nucleic acid molecules may comprise (i) the first subset of the plurality of nucleic acid molecules, in which the first nucleotides (e.g., labeled, unlabeled, or mixed) of the first plurality of nucleotides have been incorporated at the given open position of the first subset of the plurality of nucleic acid molecules, and (ii) the second subset of the plurality of nucleic acid molecules in which the second nucleotides of the second plurality of nucleotides (e.g., labeled, unlabeled, or mixed) have been incorporated at the given open position of the second subset of the plurality of nucleic acid molecules. In some instances, subsequent to a second flow of the second reaction mixture, each nucleic acid molecule of the first and second subsets of the plurality of nucleic acid molecules may have incorporated a nucleotide at an incorporation site, whether in the first subset (labeled or unlabeled) or the second subset (labeled or unlabeled). That is, subsequent to the second flow, all of the available incorporation sites of the first and second subsets of the plurality of nucleic acid molecules may have incorporated nucleotides from either the first reaction mixture or the second reaction mixture, such that the nucleic acid molecules of the first and second subsets of the plurality of nucleic acid molecules are in phase. In some cases, the plurality of nucleic acid molecules consists of the first subset of the plurality of nucleic acid molecules and the second subset of the plurality of nucleic acid molecules such that, subsequent to a second flow of the second reaction mixture, each nucleic acid molecule of the plurality of nucleic acid molecules may have incorporated a nucleotide at an incorporation site. Alternatively, in some instances, at the end of this operation (e.g., after the duration of contact between the plurality of nucleic acid molecules and the second reaction mixture), the plurality of nucleic acid molecules may further comprise (iii) a third subset of the plurality of nucleic acid molecules, different from the first and second subsets, in which the incorporation site remains open for incorporation. That is, subsequent to the second flow, only a fraction of the available incorporation sites of the plurality of sequences of the plurality of nucleic acid molecules may have incorporated first nucleotides of the first plurality of nucleotides of the first reaction mixture and only a fraction of the available incorporation sites may have incorporated second nucleotides of the second plurality of nucleotides of the second reaction mixture, leaving another fraction of the available incorporation sites open for incorporation. In this example, a third reaction mixture comprising a third plurality of nucleotides of any type (e.g., labeled, unlabeled, unterminated, reversibly terminated nucleotides, or a combination thereof, etc.) may be brought into contact with the plurality of nucleic acid molecules under conditions sufficient to incorporate third nucleotides of the third plurality of nucleotides into third sequences coupled (e.g., hybridized) to the third subset of the plurality of nucleic acid molecules. Such flows of fractional incorporation of nucleotides may be repeated until all available incorporation sites have incorporated a nucleotide, and the plurality of nucleic acid molecules are in phase. In some instances, when all available incorporation sites have incorporated nucleotides such that the plurality of nucleic acid molecules are in phase, a majority of the incorporation sites may have incorporated an unlabeled nucleotide and a minority of the incorporation sites may have incorporated a labeled nucleotide. For example, at least about 50%, 55%, 60%, 65%, 70%, 75%, 80%, 85%, 90%, 95% or more of the available incorporation sites may have incorporated an unlabeled nucleotide. In some cases, all of the incorporation sites incorporate nucleotides that are reversibly terminated. In some cases, all of the incorporation sites incorporate nucleotides that are non-terminated.

Signals detected (e.g., from a detection area) that correspond to the first nucleotides of the first plurality of nucleotides incorporated into the first sequences coupled to the first subset of the plurality of nucleic acid molecules may be used to identify one or more nucleic acid bases of the plurality of nucleic acid molecules. Alternatively or in addition, signals detected that correspond to the second nucleotides of the second plurality of nucleotides incorporated into the second sequences coupled to the second subset of the plurality of nucleic acid molecules may be used to identify one or more nucleic acid bases of the plurality of nucleic acid molecules. Alternatively or in addition, signals detected that correspond to the third nucleotides of the third plurality of nucleotides incorporated into the third sequences coupled to the third subset of the plurality of nucleic acid molecules may be used to identify one or more nucleic acid bases of the plurality of nucleic acid molecules, and so on. Signals may be detected after a given flow (e.g., after bringing the plurality of nucleic acid molecules into contact with a given reaction mixture). In other words, signals may be detected after incorporation of the first plurality of nucleotides, and/or after incorporation of the second plurality of nucleotides, etc. In some instances, signals may be detected prior to, during, or subsequent to, any flow (e.g., first flow, second flow, third flow, fourth flow, etc.). In some cases, signals may be detected subsequent to a wash flow and/or cleavage flow.

After signal detection (e.g., final signal detection in a given sequencing read cycle), reversibly terminated, incorporated nucleotides, if any, may be unblocked. Alternatively or in addition, after signal detection, labeled, incorporated nucleotides, if any, may be subject to unlabelling reactions to remove or otherwise inactivate label moieties. In some cases, unblocking may comprise removing all or a portion of a reversible terminator and/or label moiety (e.g., fluorescent dye). Unblocking or unlabelling may be achieved using, for example, a cleavage reagent (e.g., in a wash or cleavage flow, as described herein). In some cases, a cleaving, unlabelling, and/or unblocking process may leave behind a scar (e.g., a chemical residue, as described herein), which scar may affect incorporation of subsequent nucleotides in a given growing strand coupled to a nucleic acid molecule coupled to a plurality of nucleic acid molecules. A scar may comprise, for example, a hydroxyl moiety. By unblocking incorporated, terminated nucleotides, new incorporation sites may be provided such that the method may be repeated and an additional cycle or portion thereof may be performed.

The method may be repeated to identify a subsequent base in the sequence. The method may be repeated multiple times to identify subsequent bases, one base at a time, such as at least 2, 3, 4, 5, 6, 7, 8, 9, 10, 15, 20, 25, 30, 35, 40, 45, 50, 100 or more times. Each repetition of the method may comprise performing a cycle (e.g., as described herein), such as a cycle in which nucleotides comprising each canonical nucleobase is brought into contact with the plurality of nucleic acid molecules coupled to a substrate (e.g., to a detection area thereof) using one or more reaction mixture flows. Different cycles may comprise the same or different flows or combinations of flows. For example, a first cycle may involve a first reaction mixture flow and a second reaction mixture flow, and a second cycle may involve a third reaction mixture flow and a fourth reaction mixture flow, which third and fourth reaction mixture flows include different combinations of nucleotides than the first and second reaction mixture flows.

The first-flow-deficient, multiple flow schemes described herein may describe flow schemes in which subsequent to the first flow, less than 100% of all available incorporation sites have incorporated a nucleotide. Beneficially, subsequent flows may result in approximately 100% of all available incorporation sites having incorporated a nucleotide (e.g., a labeled or unlabeled nucleotide) such that the plurality of nucleic acid molecules are in phase. Beneficially, these flow schemes can minimize the percentage of, and facilitates distribution of, nucleic acid molecules in the plurality of nucleic acid molecules (e.g., in a colony) that have growing strands that may carry a "scar" (e.g., chemical residue), which scars may be created as a result of cleaving labels (e.g., dye moiety) and/or reversible terminators from labeled nucleotides in between cycles. As only a fraction of the plurality of nucleic acid molecules incorporates labeled nucleotides, and the small fraction that does incorporate labeled nucleotides may be distributed across all of the plurality of nucleic acid molecules such that it is less likely that any eventual scars will be adjacent to one other, it less likely that such scars will interfere with subsequent incorporations.

The methods described herein may be used to analyze a plurality of nucleic acid molecules. The plurality of nucleic acid molecules may be distributed on a support in distinct colonies (e.g., as described herein). For example, a support may include a collection of colonies, each of which may correspond to a different target nucleic acid molecule. A colony may include a plurality of copies of the target nucleic acid molecule or, in some cases, its complement. In some cases, nucleic acid strands corresponding to a complement of a target nucleic acid molecule may be denatured to remove complementary strands and enrich the target nucleic acid molecule and its copies within a given colony. Selective denaturation of complementary strands may be achieved by, for example, detaching a given adapter from a support and/or altering temperature, pH, or chemical conditions.

A method of analyzing nucleic acid sequences may comprise bringing a plurality of nucleic acid molecules in contact with a reaction mixture. The reaction mixture may include a plurality of nucleotides (e.g., nucleotides and nucleotide analogs). A reaction mixture may include any useful combination of nucleotides. For example, a reaction mixture may include one or more nucleotides selected from the group consisting of adenine-, guanine-, cytosine-, and thymine-containing nucleotides. In some cases, a reaction mixture may include nucleotides comprising a single canonical nucleobase type (e.g., a single canonical nucleotide type). In other cases, a reaction mixture may include nucleotides comprising two canonical nucleobase types (e.g., adenine- and cytosine-containing nucleotides). In some cases, a reaction mixture may include nucleotides comprising three or more canonical nucleobase types (e.g., three or more canonical nucleotide types). For example, a reaction mixture may include nucleotides comprising four canonical nucleobase types (e.g., adenine-, cytosine-, guanine-, and thymine-containing nucleotides). Nucleotides included in a reaction mixture may be present at any desired relative concentration. For example, a reaction mixture may include equal concentrations of a first nucleotide type and a second nucleotide type. In an example, a reaction mixture may include equal concentrations of four different nucleotides (e.g., adenine-, cytosine-, guanine-, and thymine-containing nucleotides). Alternatively, a reaction mixture may include unequal concentrations of nucleotides. For example, a reaction mixture may include more of a first nucleotide type than of a second nucleotide type, such as at least 1%, 2%, 5%, 10%, 15%, 20%, 25%, 30%, 35%, 40%, 45%, 50%, 55%, 60%, 65%, 70%, 75%, 80%, 85%, 90%, 95%, 100%, or a greater concentration of a first nucleotide type relative to a second nucleotide type. In some cases, a reaction mixture may include at least two times, three times, four times, five times, or ten times more of a first nucleotide type relative to a second nucleotide type. In an example, a reaction mixture includes four different nucleotide types comprising four different canonical nucleobase types, each of which is present in a different concentration (e.g., a first type at 50%, a second type at 25%, a third type at 20%, and a fourth type at 5%). The composition of the reaction mixture (e.g., relative concentration and/or relative identities of each canonical base) may be known.

Nucleotides of a reaction mixture may be reversibly terminated (e.g., as described herein). For example, a reaction mixture may include reversibly terminated nucleotides including one or more of adenine, guanine, cytosine, and thymine. In a particular example, a reaction mixture may include reversibly terminated nucleotides including adenine, guanine, cytosine, and thymine. In some cases, each nucleotide of a reaction mixture may be reversibly terminated. In some cases, different nucleotides of a reaction mixture may comprise different reversible terminators. Nucleotides of a reaction mixture may include any useful reversible terminator. In some cases, irradiation may be used to cleave a reversible terminator from a nucleotide. In other cases, a cleavage reagent may be used to cleave a reversible terminator from a nucleotide. Following removal of a reversible terminator, its blocking effect may be nullified. Accordingly, removal of a reversible terminator may provide an incorporation site for incorporation of an additional nucleotide (e.g., in a subsequent reaction mixture flow). Unblocking may be performed after completion of a reaction mixture flow. In some cases, unblocking may also be performed before a wash flow. In some cases, unblocking may be followed by a wash flow. For example, performing a portion of a cycle may comprise providing a reaction mixture flow, providing a first wash flow (e.g., to remove unincorporated nucleotides of the reaction mixture), unblocking the incorporated nucleotides (e.g., via providing a cleavage reagent or irradiation), and providing a second wash flow (e.g., to remove cleaved reversible terminators).

All or a portion of the nucleotides of a reaction mixture, such as the first reaction mixture, may be labeled with a fluorescent moiety (e.g., as described herein). In some cases, a reaction mixture may include fluorescently labeled, reversibly terminated nucleotides. For example, a reaction mixture may include two different nucleotide types comprising two different canonical nucleobase types (e.g., adenine- and cytosine-containing nucleotides or adenine- and thymine-containing nucleotides) that are each both fluorescently labeled and reversibly terminated. In some cases, nucleotides of different types may be labeled with different labels. In some cases, nucleotides of different types may be labeled with the same label. In some cases, nucleotides of different types may comprise the same reversible terminators. In other cases, nucleotides of different types may comprise different reversible terminators. In another example, a reaction mixture may include four different nucleotide types comprising four different canonical nucleobase types (e.g., adenine-, cytosine-, guanine-, and thymine-containing nucleotides) that are each both fluorescently labeled and reversibly terminated. In some cases, all or a portion of the nucleotides of a reaction mixture may be unlabeled. In a further example, a reaction mixture, such as a second reaction mixture, may include four different nucleotide types comprising four different canonical nucleobase types (e.g., adenine-, cytosine-, guanine-, and thymine-containing nucleotides) that are reversibly terminated and are not fluorescently labeled. In some cases, a reaction mixture may comprise a mixture of labeled and unlabeled nucleotides. For example, the reaction mixture may comprise a mixture of labeled and unlabeled nucleotides for a canonical base type (e.g., labeled C-base, unlabeled C-base). In another example, the reaction mixture may comprise a mixture of labeled nucleotides for a first canonical base type (e.g., labeled A-base), unlabeled nucleotides for a second canonical base type (e.g., unlabeled G-base), and a mixture of labeled and unlabeled nucleotides for a third canonical base type (e.g., T-base). In an example, a portion of the first nucleotides of a first nucleotide type of a first reaction mixture may be labeled and a portion of the first nucleotides of the first nucleotide type of the first reaction mixture may be unlabeled. For example, less than about 90%, 80%, 70%, 60%, 50%, 40%, 30%, 20%, 10%, 5%, or 1% of first nucleotides of a first nucleotide type of a first reaction mixture may be labeled. In some cases, at least about 90%, 80%, 70%, 60%, 50%, 40%, 30%, 20%, 10%, 5%, or 1% of first nucleotides of a first nucleotide type of a first reaction mixture may be labeled.

Nucleotides of a reaction mixture that are fluorescently labeled may include the same or different labels. For example, a fluorescently labeled adenine-containing nucleotide and a fluorescently labeled cytosine-containing nucleotide in the same reaction mixture may include the same or different fluorescent labels. A reaction mixture may include two or more nucleotides having different bases and the same fluorescent labels. Alternatively, a reaction mixture may include two or more nucleotides having different bases and different fluorescent labels. Different fluorescent labels may have different excitation and/or emission wavelengths. In some cases, different fluorescent labels may fluoresce in similar regions of the electromagnetic spectrum. For example, a first fluorescent label may fluoresce green (e.g., between about 500 and 550 nm) and a second fluorescent label may fluoresce yellow (e.g., between about 550 nm and about 625 nm). Alternatively, different fluorescent labels may fluoresce in different regions of the electromagnetic spectrum. For example, a first fluorescent label may fluoresce green (e.g., between about 500 and 550 nm) and a second fluorescent label may fluoresce red (e.g., between about 650 nm and 750 nm). In some cases, the same label attached to different nucleotides (e.g., nucleotides including different base types) may fluoresce at a slightly different wavelength. For example, a first labeled nucleotide may fluoresce at a first wavelength, and a second labeled nucleotide including the same label as the first labeled nucleotide may fluoresce at a second wavelength that is shifted (e.g., upshifted or downshifted) somewhat relative to the first wavelength based on other features of the nucleotide. In some cases, the same label attached to different nucleotides (e.g., nucleotides including different base types) may be optically detected at substantially the same, or otherwise indistinguishable (e.g., due to the proximity of the wavelengths and/or to the detection limits of the detector), wavelength. As used herein, the term "monochrome" or "monochromatic" may be applied to describe systems in which multiple nucleotide types comprising multiple canonical nucleobase types include the same fluorescent label, regardless of whether the label fluoresces at precisely the same wavelength or with the same efficiency.

The methods described herein provide a first type of reaction, in which the effective incorporation percentage in a plurality of nucleic acid molecules (e.g., a colony) from exposure to a reaction mixture is less than 100%. The effective incorporation percentage may refer to, in a population of nucleic acid molecules, the ratio of a number of available incorporation sites for incorporation of a canonical base type that have incorporated a nucleotide of the canonical base type to the total number of available incorporation sites for the canonical base type. That is, at the end of the first type of reaction, fewer than the total number of available incorporation sites in the plurality of nucleic acid molecules (e.g., a colony) may have incorporated a nucleotide (e.g., a labeled nucleotide). For example, the effective incorporation percentage for the first type of reaction may be at most about 99%, 98%, 97%, 96%, 95%, 94%, 93%, 92%, 91%, 90%, 85%, 80%, 75%, 70%, 65%, 60%, 55%, 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, or 1%. In some instances, the effective incorporation percentage for the first type of reaction may be at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or greater. In some instances, the effective incorporation percentage for the first type of reaction may be at least a ratio sufficient to yield a detectable signal from the plurality of nucleic acid molecules, where at least a subset of the incorporated nucleotides are labeled. In some instances, the first type of reaction may be conducted under a first set of conditions and a second type of reaction (described elsewhere herein) may be conducted under a second set of conditions different from the first set of conditions. In some instances, the effective incorporation percentage of less than 100% may be achieved by modulating or optimizing the reaction conditions of the first type of reaction, such as shortening incubation time of the reaction mixture to the plurality of nucleic acid molecules and/or providing rate slowing (or otherwise rate limiting) conditions (e.g., by adjusting magnesium, manganese, and/or strontium levels, enzyme levels, etc.). For example, any combination of divalent cations and/or multivalent cations can be used, and/or relative concentrations thereof adjusted to inhibit incorporation and slow down the effective incorporation rate. In an example, concentrations of cations such as strontium can be increased and/or substituted to replace other ions (e.g., magnesium, manganese, etc.) to reduce the effective incorporation rate. Alternatively or in addition, concentrations of cations such as manganese and/or magnesium can be decreased (or omitted) to reduce the effective incorporation rate. The reverse (e.g., decreasing strontium, increasing manganese or magnesium, etc.) may increase the effective incorporation rate where desired. In some instances, the concentration or relative amounts of different nucleotide types (including labeled nucleotides) in the reaction mixture may be modulated or optimized with respect to the reaction conditions. Reaction conditions may be modulated to decrease or increase incorporation rate by adjusting, for example, incubation time, nucleotide concentration, temperature, pH level, salt concentration, enzyme concentration, magnesium concentration, manganese concentration, strontium concentration, other catalyst concentrations, crowding or viscosity reagents concentration, reaction mixture volume, reaction mixture dispense velocity (to the nucleic acid molecules), and other factors. A reaction condition may refer to a composition of a reaction mixture (e.g., a concentration of an element in the reaction mixture). In some instances, the nucleotides or other reagents in the reaction mixture may be modified to slow down the reaction. In some cases, the effective incorporation rate for a labeled nucleotide of a first type may be different than the effective incorporation rate for an unlabeled nucleotide of the first type. For example, the effective incorporation rate for a labeled nucleotide of the first type may be slower than the effective incorporation rate for the unlabeled nucleotide of the first type (e.g., due to sterics and other kinetic considerations). In some instances, the reaction conditions of the first type of reaction may be modulated to optimize and facilitate incorporation reactions to go to completion, towards a 100% incorporation rate, and yet result in less than 100% incorporation because of reaction kinetics and/or other factors that stagger completion at close to 100% (e.g., at 95%, 96%, 97%, 98%, 99%, 99.1%, 99.2%, 99.3%, 99.4%, 99.5%, 99.6%, 99.7%, 99.8%, 99.9%, etc.). For example, the first type of reaction conditions may comprise providing an excess amount of nucleotides in the reaction mixture, increasing incubation time of the reaction mixture to the plurality of nucleic acid molecules, and/or providing other rate increasing conditions (e.g., by adjusting magnesium, manganese, and/or strontium concentrations, enzyme concentrations, salt concentrations, pH levels, crowding or viscosity reagent concentrations, temperature, etc.).

The methods described herein provide a second type of reaction, in which the effective incorporation percentage is about 100%. That is, at the end of the second type of reaction, substantially all of the total available incorporation sites in the plurality of nucleic acid molecules may have incorporated a nucleotide. In some instances, the effective incorporation percentage of about 100% may be achieved by providing an excess amount of nucleotides in the reaction mixture, increasing incubation time of the reaction mixture to the plurality of nucleic acid molecules, and/or providing other rate increasing conditions (e.g., by adjusting magnesium, manganese, and/or strontium levels, enzyme levels, etc.) for the second type of reaction. Reaction conditions may be modulated by adjusting, for example, incubation time, nucleotide concentration, temperature, pH level, salt concentration, enzyme concentration, magnesium concentration, manganese concentration, strontium concentration, other catalyst concentrations, crowding or viscosity reagents, reaction volume, reaction mixture dispense velocity, and other factors.

A reaction mixture may include any useful concentration or relative amount of nucleotide types (e.g., nucleotides comprising various canonical base types). The concentration or relative amount of a given nucleotide type in a reaction mixture may correlate to a given number of nucleic acid molecules (e.g., nucleic acid molecules attached to a support, such as a detection area of a support; nucleic acid molecules in a colony; etc.). For example, the concentration or relative amount of a given nucleotide type may correspond to about 5% of the total nucleic acid molecules. In some cases, nucleic acid molecules may have primers (e.g., sequencing primers) hybridized thereto, and may be capable of undergoing a primer extension reaction involving incorporation of a nucleotide. Accordingly, the concentration or relative amount of a given nucleotide type in a reaction mixture may correspond to a given number of potential positions at which a nucleotide may be incorporated (e.g., into sequences coupled to the plurality of nucleic acid molecules for which an incorporation site is available). In some cases, a nucleotide type may be present in a reaction mixture at a concentration or relative amount corresponding to less than 100% of the total number of nucleic acid molecules (e.g., nucleic acid molecules coupled to a support, such as a detection area of a support). In certain cases, a nucleotide type may be present in a reaction mixture at a concentration or relative amount corresponding to less than or equal to about 50% of the total number of nucleic acid molecules. For example, a nucleotide type may be present in a reaction mixture at a concentration or relative amount corresponding to less than or equal to about 45%, 40%, 35%, 30%, 25%, 20%, 15%, or 10% of the total number of nucleic acid molecules, such as less than 30% or less than 20% of the total number of nucleic acid molecules. In some cases, the concentration or relative amount of a nucleotide type in a reaction mixture may correspond to less than or equal to 10% of the total number of nucleic acid molecules. For example, the concentration or relative amount of a nucleotide type in a reaction mixture may correspond to less than or equal to about 9%, 8%, 7%, 6%, 5%, 4%, 3%, 2%, 1%, or 0.5% of the total number of nucleic acid molecules. In some cases, the concentration or relative amount of a nucleotide type in a reaction mixture may correspond to less than or equal to about 5% of the total number of nucleic acid molecules. Alternatively, the concentration or relative amount of a nucleotide type in a reaction mixture may correspond to greater than or equal to about 50% of the total number of nucleic acid molecules. For example, the concentration or relative amount of a nucleotide type in a reaction mixture may correspond to greater than or equal to about 55%, 60%, 65%, 70%, 75%, 80%, 85%, 90%, 95%, or 100% of the total number of nucleic acid molecules. In some cases, the concentration or relative amount of a nucleotide type in a reaction mixture may correspond to greater than or equal to about 70% of the total number of nucleic acid molecules. In certain cases, the concentration or relative amount of a nucleotide in a reaction mixture may correspond to greater than or equal to about 100% of the total number of nucleic acid molecules. In some cases, the sum of the relative amounts of a nucleotide type in a first reaction mixture and a second reaction mixture may be at least about 95% of the total number of nucleic acid molecules. Alternatively or in addition to, the sum of the relative amounts of a nucleotide type in a first reaction mixture and a second reaction mixture may be at least about 55%, 60%, 65%, 70%, 75%, 80%, 85%, 90%, 95%, or 100% of the total number of nucleic acid molecules. Alternatively or in addition to, the sum of the relative amounts of a nucleotide type in each reaction mixture introduced to the nucleic acid molecules in a given sequencing cycle may be at least about 95% of the total number of nucleic acid molecules. For example, there may be 1, 2, 3, 4, 5, 6, 7, 8, 9, 10, 20 or more reaction mixtures introduced to the nucleic acid molecules during a given sequencing cycle. Alternatively or in addition to, the sum of the relative amounts of a nucleotide type in each reaction mixture introduced to the nucleic acid molecules in a given sequencing cycle may be at least about 55%, 60%, 65%, 70%, 75%, 80%, 85%, 90%, 95%, or 100% of the total number of nucleic acid molecules.

Accordingly, the concentration or relative amount of a given nucleotide type in a reaction mixture may correspond to a given number of potential positions at which a nucleotide may be incorporated (e.g., into sequences coupled to the plurality of nucleic acid molecules for which an incorporation site is available).

In some cases, a nucleotide type may be present in a reaction mixture at a concentration or relative amount corresponding to less than 100% of the total number of nucleic acid molecules (e.g., nucleic acid molecules coupled to a support, such as a detection area of a support) having a corresponding available incorporation site (e.g., an incorporation site available for the given nucleotide type). In certain cases, a nucleotide type may be present in a reaction mixture at a concentration or relative amount corresponding to less than or equal to about 50% of the total number of nucleic acid molecules having a corresponding available incorporation site. For example, a nucleotide type may be present in a reaction mixture at a concentration or relative amount corresponding to less than or equal to about 45%, 40%, 35%, 30%, 25%, 20%, 15%, or 10% of the total number of nucleic acid molecules having a corresponding available incorporation site, such as less than 30% or less than 20% of the total number of nucleic acid molecules having a corresponding available incorporation site. In some cases, the concentration or relative amount of a nucleotide type in a reaction mixture may correspond to less than or equal to 10% of the total number of nucleic acid molecules having a corresponding available incorporation site. For example, the concentration or relative amount of a nucleotide type in a reaction mixture may correspond to less than or equal to about 9%, 8%, 7%, 6%, 5%, 4%, 3%, 2%, 1%, or 0.5% of the total number of nucleic acid molecules having a corresponding available incorporation site. In some cases, the concentration or relative amount of a nucleotide type in a reaction mixture may correspond to less than or equal to about 5% of the total number of nucleic acid molecules having a corresponding available incorporation site. Alternatively, the concentration or relative amount of a nucleotide type in a reaction mixture may correspond to greater than or equal to about 50% of the total number of nucleic acid molecules having a corresponding available incorporation site. For example, the concentration or relative amount of a nucleotide type in a reaction mixture may correspond to greater than or equal to about 55%, 60%, 65%, 70%, 75%, 80%, 85%, 90%, 95%, or 100% of the total number of nucleic acid molecules having a corresponding available incorporation site. In some cases, the concentration or relative amount of a nucleotide type in a reaction mixture may correspond to greater than or equal to about 70% of the total number of nucleic acid molecules having a corresponding available incorporation site. In certain cases, the concentration or relative amount of a nucleotide in a reaction mixture may correspond to greater than or equal to about 100% of the total number of nucleic acid molecules having a corresponding available incorporation site. In some cases, the sum of the relative amounts of a nucleotide type in a first reaction mixture and a second reaction mixture may be at least about 95% of the total number of nucleic acid molecules having a corresponding available incorporation site. Alternatively or in addition to, the sum of the relative amounts of a nucleotide type in a first reaction mixture and a second reaction mixture may be at least about 55%, 60%, 65%, 70%, 75%, 80%, 85%, 90%, 95%, or 100% of the total number of nucleic acid molecules having a corresponding available incorporation site. Alternatively or in addition to, the sum of the relative amounts of a nucleotide type in each reaction mixture introduced to the nucleic acid molecules in a given sequencing cycle may be at least about 95% of the total number of nucleic acid molecules having a corresponding available incorporation site. For example, there may be 1, 2, 3, 4, 5, 6, 7, 8, 9, 10, 20 or more reaction mixtures introduced to the nucleic acid molecules during a given sequencing cycle. Alternatively or in addition to, the sum of the relative amounts of a nucleotide type in each reaction mixture introduced to the nucleic acid molecules in a given sequencing cycle may be at least about 55%, 60%, 65%, 70%, 75%, 80%, 85%, 90%, 95%, or 100% of the total number of nucleic acid molecules having a corresponding available incorporation site.

The amount of a given nucleotide type in a reaction mixture may correlate to a rate of incorporation of the given nucleotide type. For example, the amount of a given nucleotide type in a reaction mixture may be selected to provide a slow effective incorporation rate of the given nucleotide type. A slow effective incorporation rate may be afforded by providing a number of nucleotides of a given type that is less than the number of available incorporation sites of nucleic acid molecules (e.g., as described herein) such that incorporation does not occur at all available incorporation sites. Similarly, a more rapid effective incorporation rate (and, in some cases, complete incorporation) may be achieved by providing a number of nucleotides of a given type that is similar to or greater than the number of available incorporation sites. A rapid effective incorporation rate may result in the incorporation of the given nucleotide type into more available incorporation sites. In some cases, a rapid effective incorporation rate may not result in the incorporation of the given nucleotide type into all available incorporation sites. In an example, a first reaction mixture includes an amount of a given nucleotide type that provides a slow effective incorporation rate of the given nucleotide type, and a second reaction mixture includes an amount of the given nucleotide type that provides a more rapid effective incorporation rate of the given nucleotide type. The given nucleotide type may thus undergo fractional incorporation into available sites of nucleic acid molecules (e.g., nucleic acid molecules attached to a support).

A reaction mixture may include a variety of components. For example, a reaction mixture may comprise a plurality of nucleotides (e.g., as described herein) as well as a polymerizing enzyme capable of incorporating a nucleotide of the plurality of nucleotides into a nucleic acid strand. A polymerizing enzyme for inclusion in a reaction mixture may be selected to provide a desired incorporation rate of a given nucleotide type into available incorporation sites of nucleic acid molecules (e.g., nucleic acid molecules immobilized to a support). For example, a polymerizing enzyme that affords a slow incorporation rate may be selected such that nucleotides will not be incorporated into all available incorporation sites. A polymerizing enzyme may afford different incorporation rates for different nucleotide types. For example, a polymerizing enzyme may afford a first incorporation rate for a first nucleotide type and a second incorporation rate for a second nucleotide type, where the second incorporation rate may be greater than the first incorporation rate. Similarly, a polymerizing enzyme may afford a first incorporation rate for a nucleotide of a first type that is labeled and a second incorporation rate for a nucleotide of the first type that is unlabeled, where the first incorporation rate may be greater than the second incorporation rate. A reaction mixture may also comprise primers (e.g., priming sequences) having sequence complementarity with the nucleic acid molecules (e.g., nucleic acid molecules attached to a support).

Nucleic acid molecules (e.g., nucleic acid molecules attached to a support) may be sequentially brought into contact with multiple flows of reaction mixtures that may be the same or different. For example, nucleic acid molecules may be brought in contact with a first reaction mixture comprising a first set of nucleotides (e.g., a first plurality of nucleotides) at a first concentration or relative amount. The nucleic acid molecules may subsequently be brought in contact with a second reaction mixture comprising a second set of nucleotides (e.g., a second plurality of nucleotides) at a second concentration or relative amount. In some cases, one or more processing or detecting steps such as washing, imaging, and cleaving reversible terminators and/or fluorescent labels may be performed between exposing nucleic acid molecules to the first and second reaction mixtures. The first and second reaction mixtures may be the same or different. First and second sets of nucleotides of the first and second reaction mixtures, respectively, may include the same or different nucleotide types. For example, both first and second sets of nucleotides may include adenine-, cytosine-, guanine-, and thymine-containing nucleotides. In another example, a first set of nucleotides may include adenine- and cytosine-containing nucleotides, and a second sect of nucleotides may include adenine- and thymine-containing nucleotides. For instance, a first reaction mixture may include a first plurality of nucleotides that are a first nucleotide type and a second plurality of nucleotides that are a second nucleotide type. A second reaction mixture may include a third plurality of nucleotides that are the same or different from the first and second nucleotide types. The relative amounts or concentrations of the nucleotides of first and second reaction mixtures may be the same or different. A first reaction mixture may include a given nucleotide type (e.g., adenine-containing nucleotide) at a first concentration or relative amount and a second reaction mixture may include the given nucleotide type (e.g., adenine-containing nucleotide) at a second concentration or relative amount that is higher or lower than the first concentration or relative amount. For example, a first reaction mixture may include at least two different types of nucleotides, such as two or more of adenine-, cytosine-, guanine-, and thymine-containing nucleotides, at a first concentration or relative amount (e.g., corresponding to less than or equal to 50% of the total number of nucleic acid molecules) and a second reaction mixture may include at least two different types of nucleotides (e.g., two, three, or four different types of nucleotides), such as two or more of adenine-, cytosine-, guanine-, and thymine-containing nucleotides, at a second concentration or relative amount that is greater than the first concentration or relative amount (e.g., corresponding to greater than 50% of the total number of nucleic acid molecules). In some cases, the first and second reaction mixtures may include the same or similar concentrations or relative amounts of given nucleotide types. In such instances, the first reaction mixture may include a first polymerizing enzyme that provides a slow rate of incorporation of a given nucleotide type, while the second reaction mixture may include a second polymerizing enzyme that provides a more rapid rate of incorporation of the given nucleotide type. In some cases, nucleic acid molecules may be brought into contact with a third reaction mixture comprising a third set of nucleotides at a third concentration or relative amount. A third set of nucleotides may include the same or different nucleotides as first and second sets of nucleotides at the same or different concentrations or relative amounts. The third reaction mixture may include a third polymerizing enzyme that may be the same or different from the first and second polymerizing enzymes.

Nucleic acid molecules (e.g., nucleic acid molecules immobilized to a support) may be brought in contact with a reaction mixture including a plurality of nucleotides under conditions sufficient to incorporate nucleotides of the plurality of nucleotides into sequences (e.g., sequences having available incorporation sites) complementary to all or a subset of the nucleic acid molecules. The conditions may comprise specific temperature, pH, and/or salt concentration or ranges thereof. In some cases, the conditions may comprise one or more reagents to regulate a rate of incorporation of a plurality of nucleotides or subset thereof. For example, the conditions may comprise varying concentrations or relative amounts of metal ions (e.g., strontium, manganese, and/or magnesium ions). Different conditions may be used for different reaction mixtures. For example, a first reaction mixture comprising a first plurality of nucleotides may be brought into contact with the nucleic acid molecules under a first set of conditions and a second reaction mixture comprising a second plurality of nucleotides may be brought into contact with the nucleic acid molecules under a second set of conditions that is different than the first set of conditions. For instance, the first set of conditions and the second set of conditions may comprise different temperatures, pH, salt concentrations, and/or reagents. The use of different conditions may facilitate tuning of incorporation rates of nucleotides (e.g., as described herein).

After exposure to a reaction mixture, signals may be detected from nucleic acid molecules (e.g., attached to a detection area of a support). For example, nucleic acid molecules in (e.g., immobilized to) a detection area may be imaged. Signals detected from a detection area may be indicative of incorporation of nucleotides into sequences coupled to the nucleic acid molecules. In some cases, signals may correspond to a change in impedance, charge, or conductivity associated with a plurality of nucleic acid molecules. In other cases, signals may be optical signals, and detection (e.g., imaging) may be performed using an optical detection scheme. In some cases, fluorescently labeled nucleotides are included in a reaction mixture and incorporated into a growing strand of a nucleic acid molecule (e.g., of a sequence coupled to a nucleic acid molecule immobilized to a detection area) by a polymerase in a primer extension reaction. Unincorporated nucleotides may be washed away from the nucleic acid molecules prior to imaging (e.g., as described herein). An optical detection scheme may comprise exposing nucleic acid molecules in a detection area to an excitation source and measuring subsequent emission. Emission (e.g., at a given wavelength or wavelength range) may indicate a presence of a labeled nucleotide that has been incorporated into a sequence coupled to an immobilized nucleic acid molecule. Signals from a detection area indicative of incorporation of different nucleotides (e.g., different types of nucleotides from a reaction mixture) into a sequence may be detected. In some cases, the signals may be binary (e.g., 0, 1) to indicate incorporation (or lack thereof) of any fluorescently labeled base without distinguishing between the labeled canonical base types. Such binary signals may be measured from an intensity (as an alternative to a wavelength) of an optical signal. In other cases, multiple differently fluorescently labeled nucleotides may be incorporated, and imaging may involve exposing nucleic acid molecules to a plurality of different excitation wavelengths and measuring emission for each separate excitation. In other cases, excitation may be provided over a plurality of wavelengths at once and emission from differently fluorescently labeled nucleotides may be measured simultaneously. A camera or other optical detector such as a charge-coupled device or a complementary metal-oxide semiconductor device may be used to detect incorporation of nucleotides into nucleic acid molecules. Where multiple reaction mixtures are brought into contact with nucleic acid molecules, signals may be detected from a detection area including the nucleic acid molecules after exposure of the nucleic acid molecules to one or more reaction mixtures. For example, imaging may be performed following exposure of nucleic acid molecules to a first reaction mixture (e.g., a first reaction mixture comprising labeled nucleotides) but not after exposure to a second reaction mixture (e.g., a second reaction mixture that does not comprise labeled nucleotides). In another example, imaging may be performed following exposure of nucleic acid molecules to a first reaction mixture and a second reaction mixture (e.g., first and second reaction mixtures comprising labeled nucleotides), but not after exposure to a third reaction mixture (e.g., a third reaction mixture that does not comprise labeled nucleotides). Imaging may facilitate a sequencing-by-synthesis analysis.

After exposure to a reaction mixture and incorporation of nucleotides into nucleic acid molecules, reversible terminators, if any, may be removed from incorporated nucleotides. In some cases, irradiation may be used to cleave a reversible terminator from a nucleotide. In other cases, a cleavage reagent may be used (e.g., in a wash or cleavage flow, as described herein). The inclusion of a reversible terminator on a nucleotide ensures that, following incorporation of the nucleotide into a growing nucleic acid strand, other nucleotides are blocked from being incorporated. In this manner, the growth of a nucleic acid strand may be controlled and, in the case of a fluorescently labeled nucleotide, the incorporation of the given nucleotide may be detected. In some cases, nucleotides of both first and second reaction mixtures (and, where used, subsequent reaction mixtures) may be reversibly terminated. In some cases, reversible terminators may be removed after each reaction mixture is brought into contact with immobilized nucleic acid molecules. In other cases, reversible terminators may be removed after two or more reaction mixtures are brought into contact with immobilized nucleic acid molecules, such as after completion of a sequencing cycle (e.g., as described herein). Alternatively, the reaction mixture may comprise non-terminated nucleotides, and cleavage of the blocking group is not needed prior to proceeding to the next incorporation.

Fluorescent labels of nucleotides may also be removed following imaging. In some cases, fluorescent labels and reversible terminators may be removed from incorporated nucleotides at the same time. In some cases, irradiation may be used to cleave a fluorescent label from a nucleotide (e.g., at the same time that a reversible terminator is removed). By removing fluorescent labels of nucleotides following incorporation of the nucleotides, detection of incorporation of subsequent labeled nucleotides may be facilitated.

Sequencing with fluorescently labeled nucleotides may result in the formation of scars after cleavage of fluorescent labels (e.g., dye moieties) from the nucleotides. For example, a chemical residue such as an alkyl or hydroxyl moiety may remain following cleavage of the fluorescent moiety or other detectable label. Scars may negatively impact sequencing by, for example, limiting read lengths. The methods described herein may involve labeling only a small fraction of nucleic acid molecule strands (e.g., DNA strands) in colonies on a detection area with fluorescently labeled nucleotides, leaving a large fraction of the nucleic acid molecules in the detection area unlabeled and thus undamaged by scars. Mixing in a small portion of labeled nucleotides with unlabeled nucleotides may overcome the "scar" problem because statistically the scars (e.g., both in-phase and out-of-phase scars) will be far removed from each other and will thus have a lower impact on sequencing quality. However, the ratio of labeled nucleotides being incorporated may change as a function of the specific sequence. Hence, the detected brightness will change. This phenomenon may be referred to as "context dependence." In some cases, if non-terminated nucleotides are used, context dependence may make it challenging to tell the difference between homopolymers of different lengths. In other cases, one or more trained algorithms may be able to resolve context dependence such that a sequence comprising consecutive bases of the same canonical base type (which can be incorporated in a single flow cycle) can be identified.

In order to overcome the context dependence issue while maintaining the advantages of the small percentage of labeled nucleotides, the labeled nucleotides (e.g., in a first reaction mixture) may be brought into contact with a set of nucleic acid molecules (e.g., nucleic acid molecules attached to a detector) under conditions such that only a small portion of the strands (e.g., strands of a given colony of nucleic acid molecules) may be extended with a fluorescently labeled nucleotide. For example, this may be accomplished by introducing only a small amount of labeled nucleotides to the set of nucleic acid molecules (e.g., in isolation or in a mixture with a majority of unlabeled nucleotides). In another example, reaction conditions may be modulated to allow only a small amount of labeled nucleotides to the set of nucleic acid molecules to be incorporated, such as by changing incubation time of the reaction mixture to the set of nucleic acid molecules and/or changing a concentration of one or more metal ions (e.g., magnesium, strontium, manganese, etc.). Following incorporation of the labeled nucleotides, the primer extension reaction will slow down and/or stop (or be caused to be stopped or slowed down) with the majority of the strands remaining un-extended. In some cases, by using reversibly terminated nucleotides, only a single base may be incorporated into a given strand of the fraction of strands undergoing extension. In other cases, non-terminated nucleotides may be used, and multiple bases may be incorporated into a given strand of the fraction of strands undergoing extension. Colonies may be interrogated (e.g., imaged) to detect the incorporation event (e.g., as described herein). After detection, the remaining un-extended strands (e.g., strands of a given colony of nucleic acid molecules) may be extended with an excess of unlabeled, reversibly terminated nucleotides (e.g., in a second reaction mixture). Labels (e.g., fluorescent labels) may be removed from the incorporated nucleotides after detection (e.g., prior to or subsequent to incorporation of an excess of unlabeled nucleotides). Reversible terminators, if any, may simultaneously or subsequently be removed from incorporated nucleotides, resulting in a large proportion of strands that do not retain a scar from the cleavage event. The process may be repeated one or more times to effect the extension of the strands by one base at a time.

In some cases, the first few cycles of the extension process described above may be used to calibrate an amount of nucleotides to be added or a duration of incubation time to allow the reagents to achieve a desired signal level (e.g., brightness). The signal level may correspond to the fraction of strands incorporating a labeled nucleotide. Calibration may be achieved by flowing low to high concentrations of nucleotides (e.g., labeled nucleotides) and imaging after each flow, or by performing multiple flow processes using very low concentrations. Similarly, several short incorporation steps may be used to determine how much time may be needed for effective incorporation. Such calibration procedures may be particularly useful in the case of strands or nucleic acid molecules including a key sequence of interest.

In some cases, a method for nucleic acid sequence identification may comprise providing a plurality of nucleic acid molecules immobilized at a detection area, wherein the plurality of nucleic acid molecules have sequence homology with a template nucleic acid molecule. The plurality of nucleic acid molecules may then be brought in contact with a first reaction mixture comprising a first plurality of nucleotides, under conditions sufficient to incorporate first nucleotides of the first plurality of nucleotides into first sequences complementary to a first subset of the plurality of nucleic acid molecules, which first nucleotides are incorporated into the first sequences at a given open position across the first subset of the plurality of nucleic acid molecules. The first plurality of nucleotides may be labeled. The conditions may comprise, for example, reagents to regulate a rate of incorporation of the first plurality of nucleotides. For example, the conditions may comprise varying strontium, manganese, and/or magnesium concentrations or relative amounts, and/or varying incubation time of the first reaction mixture to the plurality of nucleic acid molecules. The plurality of nucleic acid molecules may then be brought in contact with a second reaction mixture comprising a second plurality of nucleotides, under conditions sufficient to incorporate second nucleotides of the second plurality of nucleotides into second sequences complementary to a second subset of the plurality of nucleic acid molecules different than the first subset, which second nucleotides are incorporated into the second sequences at the given open position across the second subset of the plurality of nucleic acid molecules. The second plurality of nucleotides may be unlabeled. Alternatively the second plurality of nucleotides may be labeled. Where both the first plurality of nucleotides and the second plurality of nucleotides are labeled, the first and second pluralities of nucleotides may be labeled with detectable moieties that are capable of yielding optical signals of a substantially same frequency or color upon excitation. In some instances, the second subset of the plurality of nucleic acid molecules may comprise a greater number of nucleic acid molecules than the first subset of the plurality of nucleic acid molecules. In other instances, the first subset of the plurality of nucleic acid molecules may comprise a greater number of nucleic acid molecules than the second subset of the plurality of nucleic acid molecules. Signals detected from the detection area that correspond to the first nucleotides incorporated into the first sequences coupled to the first subset of the plurality of nucleic acid molecules may then be used to identify one or more nucleic acid bases of the plurality of nucleic acid molecules. The signals may be optical signals. Alternatively, the signals may correspond to a change in impedance, charge, capacitance, current, or conductivity associated with the plurality of nucleic acid molecules. In some cases, the method further comprises detecting the signals from the detection area. The signals may be detected after providing the first reaction mixture. Alternatively or in addition, the signals may be detected before providing the second reaction mixture.

In some cases, the first subset of the plurality of nucleic acid molecules may comprise a greater number of nucleic acid molecules than the second subset of the plurality of nucleic acid molecules. For example, the first relative amount of first sequences into which nucleotides of the first reaction mixture are incorporated may correspond to greater than about 50%, 60%, 70%, 80%, 90%, 91%, 92%, 93%, 94%, 95%, 96%, 97%, 98%, 99% or more. In some cases, the second subset of the plurality of nucleic acid molecules may comprise a greater number of nucleic acid molecules than the first subset of the plurality of nucleic acid molecules. For example, a first relative amount of first sequences into which nucleotides of the first reaction mixture are incorporated may correspond to less than or equal to 50% of individual nucleic acid molecules of the plurality of nucleic acid molecules. For example, the first relative amount may correspond to less than or equal to 30%, 20%, 10%, or 5% of individual nucleic acid molecules of the plurality of nucleic acid molecules. A second relative amount of second sequences into which nucleotides of the second reaction mixture are incorporated may correspond to greater than or equal to 50% of individual nucleic acid molecules of said plurality of nucleic acid molecules. For example, the second relative amount may correspond to greater than or equal to 70% or 90% of individual nucleic acid molecules of the plurality of nucleic acid molecules. In some cases, a sum of the first relative amount and the second relative amount may correspond to greater than or equal to 90% of individual nucleic acid molecules of the plurality of nucleic acid molecules.

In some cases, the first plurality of nucleotides and/or the second plurality of nucleotides may be reversibly terminated. The method may further comprise, after detecting signals from the detection area, removing reversible terminators of the first nucleotides and/or the second nucleotides (e.g., as described herein). The first nucleotides of the first plurality of nucleotides may comprise a blocking group at their 3' ends. The 3' ends of the first nucleotides may comprise labels.

In some cases, the first plurality of nucleotides are labeled with a plurality of detectable moieties and, after providing the first reaction mixture to the plurality of nucleic acid molecules, the plurality of detectable moieties may be removed (e.g., as described herein).

The first nucleotides of the first plurality of nucleotides of the first reaction mixture may be incorporated at a first incorporation rate, and second nucleotides of the second plurality of nucleotides of the second reaction mixture may be incorporated at a second incorporation rate. The second incorporation rate may be greater than the first incorporation rate. Alternatively, the first incorporation rate may be greater than the second incorporation rate.

In some cases, the first reaction mixture may comprise a third plurality of nucleotides that are labeled, wherein the first plurality of nucleotides and the third plurality of nucleotides are of different types (e.g., include different nucleobases), and the method may further comprise detecting signals from the detection that correspond to third nucleotides of the third plurality of nucleotides that are incorporated into first sequences coupled to the first subset of the plurality of nucleic acid molecules. In an example, the first plurality of nucleotides may comprise adenine nucleobases (A) and the third plurality of nucleotides may comprise thymine nucleobases (T), such that the first reaction mixture comprises a mix of A and T bases. At a first detection event, the first detection may detect signals that are indicative of incorporation of either A or T at an available incorporation site. Then, the plurality of nucleic acid molecules may be brought in contact with a third reaction mixture comprising a fourth plurality of nucleotides that are labeled and a fifth plurality of nucleotides, where the fifth plurality of nucleotides are of a same type as the first plurality of nucleotides. This may be performed under conditions sufficient to incorporate fourth nucleotides of the fourth plurality of nucleotides and fifth nucleotides of the fifth plurality of nucleotides into third sequences complementary to a third subset of the plurality of nucleic acid molecules, which first plurality of nucleotides or fourth plurality of nucleotides are incorporated into the third sequences at the given open position across the third subset of the plurality of nucleic acid molecules. The first, third, and fourth plurality of nucleotides may be of different types. The fourth plurality of nucleotides and/or the fifth plurality of nucleotides may be labeled. For example, the fourth plurality of nucleotides and the fifth plurality of nucleotides may be labeled with detectable moieties that are capable of yielding optical signals of a substantially same color or frequency upon excitation. In some cases, the first plurality of nucleotides and the third plurality of nucleotides may be labeled with detectable moieties that are capable of yielding optical signals of a substantially same color or frequency upon excitation.

At a second detection event, signals indicative of fourth nucleotides of the fourth plurality of nucleotides and/or fifth nucleotides of the fifth plurality of nucleotides being incorporated into the third sequences of the third subset of the plurality of nucleic acid molecules may then be detected from the detection area. In the above example, the fourth plurality of nucleotides may comprise cytosine (C), such that the third reaction mixture comprises A and C bases. This second detection may detect signals that are indicative of incorporation of either A or C. All or a portion of the fourth plurality of nucleotides and/or the fifth plurality of nucleotides may be labeled with detectable moieties that yield optical signals of a substantially similar frequency. The first plurality of nucleotides and the third plurality of nucleotides may be labeled with detectable moieties that yield optical signals of substantially the same frequency. For example, the first plurality of nucleotides and the third plurality of nucleotides may be labeled with detectable moieties that yield optical signals of the same color. In an example, where the first/fifth (e.g., A base), third (e.g., T base), and fourth (e.g., C base) plurality of nucleotides are labeled with detectable moieties that yield optical signals of substantially the same frequency, a digital output may be computed from a difference between the second detection and the first detection to determine which of four base types are in the given position in the sequence. For example, where dark signals (e.g., no signals) are detected in both detection events, and the digital difference is 0, the digital output may be indicative of incorporation of a G base (or that the given position in the sequence is G). For example, where no signals are detected in the first detection event but a signal is detected in the second detection event, and the digital difference is a positive increase (e.g., +1), the digital output may be indicative of incorporation of a C base (or that the given position in the sequence is C). For example, where a signal is detected in the first detection event, but no change in signal is detected in the second detection event, and the digital difference is 0, the digital output may be indicative of incorporation of a T base (or that the given position in the sequence is T). For example, where a signal is detected in the first detection event, and there is an increase in signal in the second detection event, and the digital difference is a positive increase (e.g., +1), the digital output may be indicative of incorporation of an A base. In some cases, the first reaction mixture may comprise at least three different types of nucleotides. For example, the first reaction mixture may include four different types of nucleotides. In some cases, an additional reaction mixture (e.g., a fourth reaction mixture) comprising a sixth plurality of nucleotides of a fourth nucleotide type (e.g., nucleotides comprising a guanine base, G) may also be used, where the sixth plurality of nucleotides are unlabeled. This additional reaction mixture may represent the completion of a sequencing cycle to provide a plurality of nucleic acid molecules coupled to a plurality of sequences for which all or a majority of incorporation sites include a nucleotide from one of the various reaction mixtures.

In some cases, the first reaction mixture comprises at least three different types of nucleotides. In some cases, at least three different types of nucleotides may be labeled with detectable moieties that yield optical signals of substantially different frequencies. In certain cases, the first reaction mixture may comprise four different types of nucleotides. The at least four different types of nucleotides may be labeled with detectable moieties that yield optical signals of substantially different frequencies. Similarly, in some cases, the second reaction mixture may comprise at least three different types of nucleotides, such as at least four different types of nucleotides.

In some cases, the first reaction mixture and/or the second reaction mixture may comprise polymerizing enzymes. The plurality of nucleic acid molecules may be immobilized at a detection area via a plurality of primers.

In some cases, a method for nucleic acid sequence identification may comprise providing a plurality of nucleic acid molecules immobilized at a detection area, wherein the plurality of nucleic acid molecules have sequence homology with a template nucleic acid molecule. The plurality of nucleic acid molecules may be brought in contact with a first reaction mixture comprising a first plurality of nucleotides, under conditions sufficient to incorporate first nucleotides of the first plurality of nucleotides into a first subset of a plurality of sequences complementary to the plurality of nucleic acid molecules, to provide a second subset of the plurality of sequences in which the first nucleotides of the first plurality of nucleotides have not been incorporated. At least a subset of the first plurality of nucleotides may be labeled. The conditions may comprise, for example, reagents to regulate a rate of incorporation of the first plurality of nucleotides. For example, the conditions may comprise varying strontium, manganese, and/or magnesium concentrations or relative amounts, and/or varying incubation time of the first reaction mixture to the plurality of nucleic acid molecules. The plurality of nucleic acid molecules may then be brought in contact with a second reaction mixture comprising a second plurality of nucleotides that are of a same type as the first plurality of nucleotides, under conditions sufficient to incorporate second nucleotides of the second plurality of nucleotides into the second subset of the plurality of sequences. The second plurality of nucleotides may be unlabeled. Alternatively, all or a portion of the second plurality of nucleotides may be labeled. The first plurality of nucleotides and the second plurality of nucleotides may be labeled with detectable moieties that are capable of yielding optical signals of a substantially same frequency and/or color upon excitation.

In some cases, the first plurality of nucleotides and/or the second plurality of nucleotides may be reversibly terminated. The method may further comprise, after detecting signals from the detection area, removing reversible terminators of the first nucleotides and/or the second nucleotides (e.g., as described herein). The first nucleotides of the first plurality of nucleotides may comprise a blocking group at their 3' ends. The 3' ends of the first nucleotides may comprise labels.

In some cases, the first plurality of nucleotides are labeled with a plurality of detectable moieties and, after providing the first reaction mixture to the plurality of nucleic acid molecules, the plurality of detectable moieties may be removed (e.g., as described herein).

The second subset of the plurality of sequences may comprise a greater number of sequences than the first subset of the plurality of sequences.

The first nucleotides of the first plurality of nucleotides of the first reaction mixture may be incorporated at a first incorporation rate, and second nucleotides of the second plurality of nucleotides of the second reaction mixture may be incorporated at a second incorporation rate. The second incorporation rate may be greater than the first incorporation rate. Alternatively, the first incorporation rate may be greater than the second incorporation rate.

The first reaction mixture may comprise at least two different types of nucleotides, wherein the first plurality of nucleotides may be of a type that is different than a type of at least a third plurality of nucleotides in said first reaction mixture. The first reaction mixture may comprise at least three different types of nucleotides, which at least three different types of nucleotides may be labeled with detectable moieties that yield optical signals of substantially different frequencies. In some cases, the first reaction mixture may comprise four different types of nucleotides. The at least four different types of nucleotides may be labeled with detectable moieties that yield optical signals of substantially different frequencies. Similarly, the second reaction mixture may comprise at least two different types of nucleotides, wherein the second plurality of nucleotides may be of a type that is different than a type of at least a fourth plurality of nucleotides in said second reaction mixture. The second reaction mixture may comprise at least three different types of nucleotides, which at least three different types of nucleotides may be labeled with detectable moieties that yield optical signals of substantially different frequencies. In some cases, the second reaction mixture may comprise four different types of nucleotides. The at least four different types of nucleotides may be labeled with detectable moieties that yield optical signals of substantially different frequencies.

The first reaction mixture or the second reaction mixture may comprise polymerizing enzymes. The plurality of nucleic acid molecules may be immobilized at a detection area via a plurality of primers.

Signals detected from the detection area that correspond to the first nucleotides of the first plurality of nucleotides incorporated into the first subset of the plurality of sequences may then be used to identify one or more nucleic acid bases of the plurality of nucleic acid molecules. In some cases, the method may further comprise detecting signals from the detection area that are indicative of the first nucleotides of the first plurality of nucleotides incorporated into the first sequences. Signals may be detected prior to and/or subsequent to interaction of the second reaction mixture with the plurality of nucleic acid molecules. The signals may be optical signals. Alternatively, the signals may correspond to a change in impedance, charge, capacitance, current, or conductivity associated with the plurality of nucleic acid molecules. In some cases, the method further comprises detecting the signals from the detection area. The signals may be detected after providing the first reaction mixture. Alternatively or in addition, the signals may be detected before providing the second reaction mixture.

In some cases, a method for nucleic acid identification may comprise bringing a first plurality of nucleic acid molecules immobilized at a first detection area and second plurality of nucleic acid molecules immobilized at a second detection area in contact with a first reaction mixture comprising a first plurality of labeled nucleotides and a second plurality of labeled nucleotides. The first detection area of the second detection area may be on a planar array. The first plurality of labeled nucleotides and the second plurality of labeled nucleotides may be of different types. The first plurality of labeled nucleotides and the second plurality of labeled nucleotides may be brought into contact with the first plurality of nucleic acid molecules and the second plurality of nucleic acid molecules under conditions sufficient to incorporate first nucleotides of the first plurality of labeled nucleotides or second nucleotides of the second plurality of labeled nucleotides into first sequences hybridized and complementary to a first subset of the first plurality of nucleic acid molecules and second sequences hybridized and complementary to a first subset of the second plurality of nucleic acid molecules. The conditions may comprise, for example, reagents to regulate a rate of incorporation of the first plurality of nucleotides. For example, the conditions may comprise varying strontium, manganese, and/or magnesium concentrations or relative amounts, and/or varying incubation time of the first reaction mixture to the plurality of nucleic acid molecules. The first plurality of nucleic acid molecules and the second plurality of nucleic acid molecules may have sequence homology to different template nucleic acid molecules. A first set of signals (e.g., optical signals, or signals that correspond to a change in impedance, charge, capacitance, current, or conductivity associated with the first and/or second plurality of nucleic acid molecules) may then be detected from the first detection area and/or the second detection area. The first set of signals may be indicative of incorporation of the first nucleotides and/or the second nucleotides into the first sequences and/or second sequences. The first plurality of nucleic acid molecules and the second plurality of nucleic acid molecules may then be brought in contact with a second reaction mixture comprising a third plurality of labeled nucleotides and a fourth plurality of labeled nucleotides, under conditions sufficient to incorporate third nucleotides of the third plurality of labeled nucleotides and/or fourth nucleotides of the fourth plurality of labeled nucleotides into third sequences hybridized and complementary to a second subset of the first plurality of nucleic acid molecules and/or fourth sequences hybridized and complementary to a second subset of the second plurality of nucleic acid molecules. The third plurality of labeled nucleotides and the fourth plurality of labeled nucleotides may be of different types. The third plurality of labeled nucleotides may be of a same type as the first plurality of labeled nucleotides or the second plurality of labeled nucleotides, and the fourth plurality of labeled nucleotides may be of a different type than the first plurality of nucleotides and the second plurality of labeled nucleotides. A second set of signals may then be detected from the first detection area and/or the second detection area. The second set of signals may be indicative of incorporation of the third nucleotides of the third plurality of labeled nucleotides and/or the fourth nucleotides of the fourth plurality of labeled nucleotides into the third sequences and/or fourth sequences. At least the first set of signals and/or the second set of signals may be used to identify one or more nucleic acid bases of the first plurality of nucleic acid molecules or the second plurality of nucleic acid molecules. The first and second sets of signals may be substantially monochromatic optical signals. The first plurality of labeled nucleotides and the second plurality of labeled nucleotides may comprise detectable moieties that yield optical signals of the first set of signals at substantially the same color and/or frequency. Similarly, the third plurality of labeled nucleotides and the fourth plurality of labeled nucleotides may also comprise detectable moieties that yield optical signals of the second set of signals at substantially the same frequency and/or color. The frequency corresponding to the first plurality of labeled nucleotides and the second plurality of labeled nucleotides may be the same as or different from the frequency corresponding to the third plurality of labeled nucleotides and the fourth plurality of labeled nucleotides.

A first relative amount of the first sequences into which first nucleotides are incorporated and a second relative amount of the second sequences into which second nucleotides are incorporated may correspond to less than or equal to 50% of individual nucleic acid molecules of the first plurality of nucleic acid molecules and less than or equal to 50% of individual nucleic acid molecules of the second plurality of nucleic acid molecules. In some cases, the first relative amount and the second relative amount may correspond to less than or equal to 30% (e.g., 20%, 10%, or 5%) of individual nucleic acid molecules of the first plurality of nucleic acid molecules and less than or equal to 30% (e.g., 20%, 10%, or 5%) of individual nucleic acid molecules of the second plurality of nucleic acid molecules.

The first reaction mixture may comprise a first polymerizing enzyme that provides a first incorporation rate of the first nucleotides and/or the second nucleotides and the second reaction mixture comprises a second polymerizing enzyme that provides a second incorporation rate of the third nucleotides and/or the fourth nucleotides, and wherein the first incorporation rate is slower than the second incorporation rate. The second nucleotides that are incorporated into the second sequences may comprise a greater number of nucleotides than the first nucleotides that are incorporated into the first sequences. The third nucleotides that are incorporated into the third sequences may comprise a greater number of nucleotides than the fourth nucleotides that are incorporated into the fourth sequences. The first plurality of labeled nucleotides, the second plurality of labeled nucleotides, the third plurality of labeled nucleotides, and the fourth plurality of labeled nucleotides may be reversibly terminated. Nucleotides of the first plurality of labeled nucleotides, the second plurality of labeled nucleotides, the third plurality of labeled nucleotides, and the fourth plurality of labeled nucleotides may comprise a blocking group at their 3' ends. The 3' ends may comprise labels.

In some cases, a flow (e.g., reaction mixture) including fewer than four nucleotide types may be brought in contact with a plurality of nucleic acid molecules. For example, only a subset of the four canonical bases (adenine, guanine, cytosine, and thymine) may be included in the reaction mixture. All of the nucleotides included in the reaction mixture may be reversibly terminated. Enzymes (e.g., polymerizing enzymes) such as Therminator are known to misincorporate reversibly terminated nucleotides when only one nucleotide triphosphate type is available for incorporation. The methods described herein may minimize or avoid this error by controlling the rate of incorporation of nucleotides into nucleic acid molecules (e.g., sequences coupled to nucleic acid molecules immobilized to a support) and/or controlling the incubation time. Incorporation rates may be controlled via, for example, the concentration or amount of a given nucleotide in a reaction mixture relative to the plurality of nucleic acid molecules and the particular nucleotides and polymerizing enzymes selected for use (e.g., as described herein). By slowing incorporation, misincorporation rates are also slowed. Typically, for a reaction mixture including both labeled and unlabeled adenine-containing nucleotides, all of which are reversibly terminated, where no other nucleotides brought in contact with nucleic acid molecules, misincorporation of labeled and unlabeled adenine-containing nucleotides occur at a finite rate. For example, misincorporation may occur at 1/20 the rate of incorporation of the correct nucleotide. Because a correct nucleotide is incorporated at a very fast rate, and it may be difficult to stop a reaction at the exact moment when it is 100% complete, misincorporation events are measurable. In the methods of the present disclosure, incorporation of correct nucleotides may be slowed to, for example, 1/100 the normal rate due to the low concentration of nucleotides in a given reaction mixture relative to the number of nucleic acid molecules (e.g., template nucleic acid molecules immobilized to a support). Accordingly, an incorporation reaction may be stopped at, for example, 20% completion, such that misincorporation rates may be slowed to, for example, 1/2000 the rate of incorporation of the correct nucleotide. Misincorporation events may no longer be detectable at such low rates. Therefore, the methods described herein may facilitate the use of flows including only a subset of the four canonical bases without the usual misincorporation.

Provided herein is a method for nucleic acid sequence identification, comprising: (a) providing a plurality of nucleic acid molecules immobilized at a detection area, wherein the plurality of nucleic acid molecules have sequence homology with a template nucleic acid molecule, wherein the template nucleic acid molecule comprises a template sequence; (b) bringing the plurality of nucleic acid molecules in contact with a first reaction mixture comprising a first plurality of nucleotides, under conditions sufficient to incorporate first nucleotides of the first plurality of nucleotides into first sequences coupled to a first subset of the plurality of nucleic acid molecules, wherein the first nucleotides are incorporated into the first sequences at a given open position of the template sequence across the first subset of the plurality of nucleic acid molecules, wherein the first plurality of nucleotides is labeled; (c) subsequent to (b), bringing the plurality of nucleic acid molecules in contact with a second reaction mixture comprising a second plurality of nucleotides, under conditions sufficient to incorporate second nucleotides from the second plurality of nucleotides into second sequences coupled to a second subset of the plurality of nucleic acid molecules, wherein the second subset of the plurality of nucleic acid molecules is different than the first subset of the plurality of nucleic acid molecules, and wherein the second nucleotides are incorporated into the second sequences at the given open position of the template sequence across the second subset of the plurality of nucleic acid molecules; and (d) using signals detected from the detection area that correspond to the first nucleotides incorporated into the first sequences to identify one or more nucleic acid bases of the plurality of nucleic acid molecules.

In some cases, the method further comprises detecting the signals from the detection area that correspond to the first nucleotides incorporated into the first sequences coupled to the first subset of the plurality of nucleic acid molecules. In some cases, the signals are detected before (c). In some cases, the signals are detected subsequent to (b). In some cases, the signals are detected before (c).

In some cases, the second subset of the plurality of nucleic acid molecules comprises a greater number of nucleic acid molecules than the first subset of the plurality of nucleic acid molecules.

In some cases, the first nucleotides of the first plurality of nucleotides of the first reaction mixture are incorporated at a first incorporation rate, and wherein the second nucleotides of the second plurality of nucleotides of the second reaction mixture are incorporated at a second incorporation rate that is greater than the first incorporation rate.

In some cases, a first relative amount of the first sequences into which the first nucleotides of the first reaction mixture are incorporated corresponds to less than or equal to 50% of individual nucleic acid molecules of the plurality of nucleic acid molecules. In some cases, the first relative amount corresponds to less than or equal to 30% of individual nucleic acid molecules of the plurality of nucleic acid molecules. In some cases, the first relative amount corresponds to less than or equal to 20% of individual nucleic acid molecules of the plurality of nucleic acid molecules. In some cases, the first relative amount corresponds to less than or equal to 10% of individual nucleic acid molecules of the plurality of nucleic acid molecules. In some cases, the first relative amount corresponds to less than or equal to 5% of individual nucleic acid molecules of the plurality of nucleic acid molecules. In some cases, a second relative amount of the second sequences into which the second nucleotides of the second reaction mixture are incorporated corresponds to greater than or equal to 50% of individual nucleic acid molecules of the plurality of nucleic acid molecules. In some cases, the second relative amount corresponds greater than or equal to 70% of individual nucleic acid molecules of the plurality of nucleic acid molecules. In some cases, the second relative amount corresponds greater than or equal to 90% of individual nucleic acid molecules of the plurality of nucleic acid molecules. In some cases, a sum of the first relative amount and the second relative amount corresponds to greater than or equal to 90% of individual nucleic acid molecules of the plurality of nucleic acid molecules.

In some cases, the first plurality of nucleotides and/or the second plurality of nucleotides are reversibly terminated. In some cases, the method further comprises, subsequent to (d), removing reversible terminators of the first nucleotides and/or the second nucleotides. In some cases, the first plurality of nucleotides and the second plurality of nucleotides are reversibly terminated. In some cases, the first nucleotides of the first plurality of nucleotides comprise a blocking group at their 3' ends. In some cases, the 3' ends of the first nucleotides comprise labels.

In some cases, the first plurality of nucleotides is labeled with a plurality of detectable moieties, and wherein, subsequent to (b), the plurality of detectable moieties is removed.

In some cases, (i) (b) comprises bringing the first reaction mixture in contact with a second plurality of nucleic acid molecules, wherein the second plurality of nucleic acid molecules have sequence homology with a second template nucleic acid molecule, wherein the second template nucleic acid molecule comprises a second template sequence; (ii) the first reaction mixture comprises a third plurality of nucleotides that are labeled, wherein the first plurality of nucleotides and the third plurality of nucleotides are of different types; (iii) the conditions in (b) are sufficient to incorporate third nucleotides of the third plurality of nucleotides into third sequences coupled to a third subset of the second plurality of nucleic acid molecules, wherein the third nucleotides are incorporated into the third sequences at a given open position of the second template sequence across the third subset of the second plurality of nucleic acid molecules; and (iv) the method further comprises detecting signals that correspond to the first nucleotides incorporated into the first sequences and the third nucleotides incorporated into the third sequences.

In some cases, the method further comprises: (i) providing a third plurality of nucleic acid molecules, wherein the third plurality of nucleic acid molecules have sequence homology with a third template nucleic acid molecule, wherein the third template nucleic acid molecule comprises a third template sequence; (ii) prior to (c), bringing the plurality of nucleic acid molecules, the second plurality of nucleic acid molecules, and the third plurality of nucleic acid molecules in contact with a third reaction mixture comprising a fourth plurality of nucleotides that are labeled and a fifth plurality of nucleotides that are labeled, under conditions sufficient to incorporate fourth nucleotides of the fourth plurality of nucleotides into fourth sequences coupled to a fourth subset of the plurality of nucleic acid molecules, and sufficient to incorporate fifth nucleotides of the fifth plurality of nucleotides into fifth sequences coupled to a fifth subset of the third plurality of nucleic acid molecules, wherein the first nucleotides and the fourth nucleotides are of the same type, and wherein the first, third, and fifth plurality of nucleotides are of different types, wherein the fourth nucleotides are incorporated into the fourth sequences at the given open position of the template sequence across the fourth subset of the plurality of nucleic acid molecules, and wherein the fifth nucleotides are incorporated into the fifth sequences at a given open position of the third template sequence across the fifth subset of the third plurality of nucleic acid molecules; and (iii) detecting signals that correspond to the fourth nucleotides incorporated into the fourth sequences and the fifth nucleotides incorporated into the fifth sequences. In some cases, the fourth plurality of nucleotides and the fifth plurality of nucleotides are labeled with detectable moieties that are capable of yielding optical signals of a substantially same frequency upon excitation. In some cases, the first plurality of nucleotides and the third plurality of nucleotides are labeled with detectable moieties that are capable of yielding optical signals of the substantially same frequency upon excitation. In some cases, the first plurality of nucleotides and the third plurality of nucleotides are labeled with detectable moieties that are capable of yielding optical signals of a same color upon excitation. In some cases, the first reaction mixture comprises at least three different types of nucleotides. In some cases, the at least three different types of nucleotides are labeled with detectable moieties that yield optical signals of substantially different frequencies. In some cases, the first reaction mixture comprises four different types of nucleotides. In some cases, the at least four different types of nucleotides are labeled with detectable moieties that yield optical signals of substantially different frequencies.

In some cases, the second reaction mixture comprises at least two different types of nucleotides, wherein the second plurality of nucleotides is of a type that is different than a type of at least a third plurality of nucleotides in the second reaction mixture. In some cases, the second reaction mixture comprises at least three different types of nucleotides. In some cases, the second reaction mixture comprises four different types of nucleotides.

In some cases, the first reaction mixture or the second reaction mixture comprises polymerizing enzymes. In some cases, the plurality of nucleic acid molecules is immobilized at the detection area via a plurality of primers.

In some cases, the signals are optical signals. In some cases, the signals correspond to a change in impedance, charge, capacitance, current, or conductivity associated with the plurality of nucleic acid molecules.

In some cases, the conditions in (b) comprise reagents to regulate a rate of incorporation of the first plurality of nucleotides. In some cases, the conditions in (b) comprise varying strontium, manganese, and/or magnesium concentrations or relative amounts, and/or varying incubation time of the first reaction mixture to the plurality of nucleic acid molecules.

In some cases, the second plurality of nucleotides is unlabeled.

In some cases, the second plurality of nucleotides is labeled. In some cases, the first plurality of nucleotides and the second plurality of nucleotides are labeled with detectable moieties that are capable of yielding optical signals of a substantially same frequency upon excitation. In some cases, the first plurality of nucleotides and the second plurality of nucleotides are labeled with detectable moieties that are capable of yielding optical signals of a same color upon excitation.

In some cases, (d) comprises identifying the type of nucleic acid bases of the plurality of nucleic acid molecules, as between the at least four different types of nucleotides, based at least in part on the optical signals of the substantially different frequencies.

Further provided herein is a method for nucleic acid sequence identification, comprising: (a) providing a plurality of nucleic acid molecules immobilized at a detection area, wherein the plurality of nucleic acid molecules have sequence homology with a template nucleic acid molecule; (b) bringing the plurality of nucleic acid molecules in contact with a first reaction mixture comprising a first plurality of nucleotides, under conditions sufficient to incorporate first nucleotides of the first plurality of nucleotides into a first subset of a plurality of sequences hybridized to the plurality of nucleic acid molecules, to provide a second subset of the plurality of sequences in which the first nucleotides of the first plurality of nucleotides have not been incorporated, wherein at least a subset of the first plurality of nucleotides is labeled; (c) subsequent to (b), bringing the plurality of nucleic acid molecules in contact with a second reaction mixture comprising a second plurality of nucleotides that are of a same type as the first plurality of nucleotides, under conditions sufficient to incorporate second nucleotides of the second plurality of nucleotides into the second subset of the plurality of sequences; and (d) using signals detected from the detection area that correspond to the first nucleotides incorporated into the first subset of the plurality of sequences to identify one or more nucleic acid bases of the plurality of nucleic acid molecules.

In some cases, the method further comprises detecting the signals from the detection area that correspond to the first nucleotides incorporated into the first subset of the plurality of sequences. In some cases, the signals are detected before (c). In some cases, the signals are detected subsequent to (b). In some cases, the signals are detected before (c).

In some cases, the conditions in (b) comprise reagents to regulate a rate of incorporation of the first plurality of nucleotides. In some cases, the conditions in (b) comprise strontium, manganese, and/or magnesium concentrations or relative amounts, and/or varying exposure time of the first reaction mixture to the plurality of nucleic acid molecules.

In some cases, the second plurality of nucleotides is unlabeled.

In some cases, the second plurality of nucleotides is labeled. In some cases, the first plurality of nucleotides and the second plurality of nucleotides are labeled with detectable moieties that are capable of yielding optical signals of a substantially same frequency upon excitation. In some cases, the first plurality of nucleotides and the second plurality of nucleotides are labeled with detectable moieties that are capable of yielding optical signals of a same color upon excitation.

In some cases, the first plurality of nucleotides and/or the second plurality of nucleotides are reversibly terminated. In some cases, first nucleotides of the at least the subset of the first plurality of nucleotides comprise a blocking group at their 3' ends. In some cases, the 3' ends of the first nucleotides comprise labels. In some cases, the method further comprises subsequent to (d), removing reversible terminators of the first nucleotides and/or the second nucleotides.

In some cases, the second subset of the plurality of sequences comprises a greater number of sequences than the first subset of the plurality of sequences.

In some cases, the first nucleotides of the first plurality of nucleotides of the first reaction mixture are incorporated at a first incorporation rate, and wherein the second nucleotides of the second plurality of nucleotides of the second reaction mixture are incorporated at a second incorporation rate that is greater than the first incorporation rate.

In some cases, the first reaction mixture comprises at least two different types of nucleotides, wherein the first plurality of nucleotides is of a type that is different than a type of at least a third plurality of nucleotides in the first reaction mixture. In some cases, the first reaction mixture comprises at least three different types of nucleotides. In some cases, the at least three different types of nucleotides are labeled with detectable moieties that yield optical signals of substantially different frequencies. In some cases, the first reaction mixture comprises four different types of nucleotides. In some cases, the at least four different types of nucleotides are labeled with detectable moieties that yield optical signals of substantially different frequencies.

In some cases, the second reaction mixture comprises at least two different types of nucleotides, wherein the second plurality of nucleotides are of a type that is different than a type of at least a fourth plurality of nucleotides in the second reaction mixture. In some cases, the second reaction mixture comprises at least three different types of nucleotides. In some cases, the at least three different types of nucleotides are labeled with detectable moieties that yield optical signals of substantially different frequencies. In some cases, the second reaction mixture comprises four different types of nucleotides. In some cases, the at least four different types of nucleotides are labeled with detectable moieties that yield optical signals of substantially different frequencies.

In some cases, the first reaction mixture or the second reaction mixture comprises polymerizing enzymes. In some cases, the plurality of nucleic acid molecules is immobilized at the detection area via a plurality of primers.

In some cases, the signals are optical signals. In some cases, the signals correspond to a change in impedance, charge, capacitance, current, or conductivity associated with the plurality of nucleic acid molecules.

In some cases, (d) comprises identifying the type of nucleic acid bases of the plurality of nucleic acid molecules, as between the at least four different types of nucleotides, based at least in part on the optical signals of the substantially different frequencies.

Further provided herein is a method for nucleic acid identification, comprising: (a) bringing a first plurality of nucleic acid molecules immobilized at a first detection area and a second plurality of nucleic acid molecules immobilized at a second detection area in contact with a first reaction mixture comprising a first plurality of labeled nucleotides and a second plurality of labeled nucleotides, under conditions sufficient to incorporate first nucleotides of the first plurality of labeled nucleotides and/or second nucleotides of the second plurality of labeled nucleotides into (i) first sequences hybridized to a first subset of the first plurality of nucleic acid molecules and/or (ii) second sequences hybridized to a first subset of the second plurality of nucleic acid molecules, wherein the first plurality of labeled nucleotides and the second plurality of labeled nucleotides are of different types, and wherein the first plurality of nucleic acid molecules and the second plurality of nucleic acid molecules have sequence homology to different template nucleic acid molecules; (b) detecting a first set of signals from the first detection area and/or the second detection area, which first set of signals is indicative of incorporation of the first nucleotides and/or the second nucleotides into the first sequences and/or the second sequences; (c) bringing the first plurality of nucleic acid molecules and the second plurality of nucleic acid molecules in contact with a second reaction mixture comprising a third plurality of labeled nucleotides and a fourth plurality of labeled nucleotides, under conditions sufficient to incorporate third nucleotides of the third plurality of labeled nucleotides and/or fourth nucleotides of the fourth plurality of labeled nucleotides into third sequences hybridized to a second subset of the first plurality of nucleic acid molecules and/or fourth sequences hybridized to a second subset of the second plurality of nucleic acid molecules, wherein the third plurality of labeled nucleotides and the fourth plurality of labeled nucleotides are of different types, wherein the third plurality of labeled nucleotides are of a same type as the first plurality of labeled nucleotides or the second plurality of labeled nucleotides, and wherein the fourth plurality of labeled nucleotides are of a different type than the first plurality of labeled nucleotides and the second plurality of labeled nucleotides; (d) detecting a second set of signals from the first detection area and/or the second detection area, which second set of signals is indicative of incorporation of the third nucleotides and/or the fourth nucleotides into the third sequences and/or the fourth sequences; and (e) using at least the first set of signals and the second set of signals to identify one or more nucleic acid bases of the first plurality of nucleic acid molecules or the second plurality of nucleic acid molecules.

In some cases, the first detection area or the second detection area is on a planar array. In some cases, the first set of signals and the second set of signals are substantially monochromatic optical signals. In some cases, the first plurality of labeled nucleotides and the second plurality of labeled nucleotides comprise detectable moieties that yield optical signals of the first set of signals at a substantially same frequency. In some cases, the third plurality of labeled nucleotides and the fourth plurality of labeled nucleotides comprise detectable moieties that yield optical signals of the second set of signals at the substantially same frequency.

In some cases, the first set of signals or the second set of signals are optical signals. In some cases, the first set of signals or the second set of signals correspond to a change in impedance, charge, or conductivity associated with the first plurality of nucleic acid molecules or second plurality of nucleic acid molecules.

In some cases, a first relative amount of the first sequences into which first nucleotides are incorporated and a second relative amount of the second sequences into which second nucleotides are incorporated correspond to less than or equal to 50% of individual nucleic acid molecules of the first plurality of nucleic acid molecules and less than or equal to 50% of individual nucleic acid molecules of the second plurality of nucleic acid molecules. In some cases, the first relative amount and the second relative amount correspond to less than or equal to 30% of individual nucleic acid molecules of the first plurality of nucleic acid molecules and less than or equal to 30% of individual nucleic acid molecules of the second plurality of nucleic acid molecules. In some cases, the first relative amount and the second relative amount correspond to less than or equal to 20% of individual nucleic acid molecules of the first plurality of nucleic acid molecules and less than or equal to 20% of individual nucleic acid molecules of the second plurality of nucleic acid molecules. In some cases, the first relative amount and the second relative amount correspond to less than or equal to 10% of individual nucleic acid molecules of the first plurality of nucleic acid molecules and less than or equal to 10% of individual nucleic acid molecules of the second plurality of nucleic acid molecules. In some cases, the first relative amount and the second relative amount correspond to less than or equal to 5% of individual nucleic acid molecules of the first plurality of nucleic acid molecules and less than or equal to 5% of individual nucleic acid molecules of the second plurality of nucleic acid molecules.

In some cases, the first reaction mixture comprises a first polymerizing enzyme that provides a first incorporation rate of the first nucleotides and/or the second nucleotides and the second reaction mixture comprises a second polymerizing enzyme that provides a second incorporation rate of the third nucleotides and/or the fourth nucleotides, and wherein the first incorporation rate is slower than the second incorporation rate. In some cases, the second nucleotides that are incorporated into the second sequences comprise a greater number of nucleotides than the first nucleotides that are incorporated into the first sequences.

In some cases, the third nucleotides that are incorporated into the third sequences comprise a greater number of nucleotides than the fourth nucleotides that are incorporated into the fourth sequences.

In some cases, the first plurality of labeled nucleotides, the second plurality of labeled nucleotides, the third plurality of labeled nucleotides, and the fourth plurality of labeled nucleotides are reversibly terminated. In some cases, nucleotides of the first plurality of labeled nucleotides, the second plurality of labeled nucleotides, the third plurality of labeled nucleotides, and the fourth plurality of labeled nucleotides comprise a blocking group at their 3' ends. In some cases, the 3' ends comprise labels.

In another aspect, the present disclosure provides a method for nucleic acid sequence identification, comprising: (a) contacting a plurality of nucleic acid molecules immobilized to a support and having sequence homology with a template nucleic acid molecule, with a first plurality of nucleotides that are labeled, under conditions sufficient to incorporate first nucleotides of the first plurality of nucleotides into at least a subset of a plurality of sequences hybridized to the plurality of nucleic acid molecules, wherein the at least the subset of the plurality of sequences is less than all of the plurality of sequences; (b) separately from (a), contacting the plurality of nucleic acid molecules with a second plurality of nucleotides, under conditions sufficient to incorporate second nucleotides of the second plurality of nucleotides into at least a subset of a remainder of the plurality of sequences in which the first nucleotides have not been incorporated in (a); and (c) using signals detected from the first nucleotides to identify one or more nucleic acid bases of the plurality of nucleic acid molecules.

In some cases, the signals are detected prior to (b). In some cases, the signals are detected during incorporation of the first nucleotides. In some cases, the signals are detected after incorporation of the first nucleotides.

In some cases, the second plurality of nucleotides is unlabeled.

In some cases, the second plurality of nucleotides is labeled. In some cases, the first plurality of nucleotides and the second plurality of nucleotides are labeled with detectable moieties that are capable of yielding optical signals of a substantially same frequency upon excitation. In some cases, the first plurality of nucleotides and the second plurality of nucleotides are labeled with detectable moieties that are capable of yielding optical signals of a same color upon excitation.

In some cases, the first plurality of nucleotides and/or the second plurality of nucleotides are reversibly terminated. In some cases, first nucleotides of the first plurality of nucleotides comprise a blocking group at their 3' ends. In some cases, the 3' ends of the first nucleotides comprise labels. In some cases, the method further comprises, subsequent to (c), removing reversible terminators of the first nucleotides and/or the second nucleotides.

In some cases, the at least the subset of the remainder of the plurality of sequences of (b) comprises a greater number of sequences than the at least the subset of the plurality of sequences of (a).

In some cases, the first nucleotides of the first plurality of nucleotides are incorporated into the at least the subset of the plurality of sequences at a first incorporation rate, and wherein the second nucleotides of the second plurality of nucleotides are incorporated into the at least the subset of the remainder of the plurality of sequences at a second incorporation rate that is greater than the first incorporation rate.

In some cases, the first nucleotides of the first plurality of nucleotides are incorporated into the at least the subset of the plurality of sequences at a first incorporation rate, and wherein the second nucleotides of the second plurality of nucleotides are incorporated into the at least the subset of the remainder of the plurality of sequences at a second incorporation rate that is lower than the first incorporation rate.

In some cases, the plurality of nucleic acid molecules is immobilized to the support via a plurality of primers.

In some cases, the signals are optical signals. In some cases, the signals correspond to a change in impedance, charge, capacitance, current, or conductivity associated with the plurality of nucleic acid molecules.

In some cases, the first plurality of nucleotides and the second plurality of nucleotides are of a same type. In some cases, the first plurality of nucleotides and the second plurality of nucleotides are of a different type.

In some cases, the method further comprises repeating (a)-(c) with a third plurality of nucleotides that are labeled and a fourth plurality of nucleotides.

In some cases, the method further comprises, subsequent to (a) and prior to (b), contacting the plurality of nucleic acid molecules with a washing solution.

Further provided herein is a method for nucleic acid identification, comprising: (a) providing a substrate comprising a first plurality of nucleic acid molecules immobilized at a first detection area, a second plurality of nucleic acid molecules immobilized at a second detection area, a third plurality of nucleic acid molecules immobilized at a third detection area, and a fourth plurality of nucleic acid molecules immobilized at a fourth detection area, wherein the first plurality of nucleic acid molecules, the second plurality of nucleic acid molecules, the third plurality of nucleic acid molecules, and the fourth plurality of nucleic acid molecules have sequence homology to different template nucleic acid molecules; (b) bringing the substrate in contact with a first reaction mixture comprising a first plurality of labeled nucleotides and a second plurality of labeled nucleotides, under conditions sufficient to incorporate first nucleotides of the first plurality of labeled nucleotides into first sequences hybridized to a first subset of the first plurality of nucleic acid molecules and second nucleotides of the second plurality of labeled nucleotides into second sequences hybridized to a first subset of the second nucleic acid molecules, wherein the first plurality of labeled nucleotides and the second plurality of labeled nucleotides are of different types; (c) detecting a first set of signals from the first detection area, the second detection area, the third detection area, and the fourth detection area to generate a first data set, wherein the first set of signals are indicative of incorporation of the first nucleotides of the first plurality of labeled nucleotides into the first sequences and of the second nucleotides of the second plurality of labeled nucleotides into the second sequences; (d) bringing the substrate in contact with a second reaction mixture comprising a third plurality of labeled nucleotides and a fourth plurality of labeled nucleotides, under conditions sufficient to incorporate third nucleotides of the third plurality of labeled nucleotides into third sequences hybridized to a second subset of the first plurality of nucleic acid molecules and fourth nucleotides of the fourth plurality of labeled nucleotides into fourth sequences hybridized to a first subset of the third plurality of nucleic acid molecules, wherein the third plurality of labeled nucleotides are of a same type as the first plurality of labeled nucleotides, and wherein the fourth plurality of labeled nucleotides are of a different type than the first plurality of labeled nucleotides and second plurality of labeled nucleotides; (e) detecting a second set of signals from the first detection area, the second detection area, the third detection area, and the fourth detection area to generate a second data set, wherein the second set of signals are indicative of incorporation of the third nucleotides of the third plurality of labeled nucleotides into the third sequences and of the fourth nucleotides into the fourth plurality of labeled nucleotides into the fourth sequences; and (f) processing the first data set and the second data set to identify one or more nucleic acid bases of the first plurality of nucleic acid molecules, the second plurality of nucleic acid molecules, the third plurality of nucleic acid molecules, and the fourth plurality of nucleic acid molecules.

In some cases, the first set of signals and the second set of signals comprise optical signals.

In some cases, the first nucleotides of the first plurality of labeled nucleotides and the second nucleotides of the second plurality of labeled nucleotides are incorporated at a first incorporation rate, and wherein the third nucleotides of the third plurality of labeled nucleotides and the fourth nucleotides of the fourth plurality of labeled nucleotides are incorporated at a second incorporation rate that is greater than the first incorporation rate.

In some cases, a first relative amount of the first sequences into which the first nucleotides are incorporated corresponds to less than or equal to 90% of individual nucleic acid molecules of the first plurality of nucleic acid molecules.

In some cases, a second relative amount of the second sequences into which the second nucleotides are incorporated corresponds to less than or equal to 90% of individual nucleic acid molecules of the second plurality of nucleic acid molecules.

In some cases, a third relative amount of the third sequences into which the third nucleotides are incorporated corresponds to less than or equal to 90% of individual nucleic acid molecules of the third plurality of nucleic acid molecules.

In some cases, a fourth relative amount of the fourth sequences into which the fourth nucleotides are incorporated corresponds to less than or equal to 90% of individual nucleic acid molecules of the fourth plurality of nucleic acid molecules.

In some cases, the first plurality labeled nucleotides, the second plurality labeled nucleotides, the third plurality labeled nucleotides, and the fourth plurality labeled nucleotides are reversibly terminated. In some cases, the first plurality labeled nucleotides, the second plurality labeled nucleotides, the third plurality labeled nucleotides, and the fourth plurality labeled nucleotides comprise a blocking group at their 3' ends. In some cases, the 3' ends of the first plurality labeled nucleotides, the second plurality labeled nucleotides, the third plurality labeled nucleotides, and the fourth plurality labeled nucleotides comprise labels.

In some cases, the first plurality of labeled nucleotides and the second plurality of labeled nucleotides are labeled with a plurality of detectable moieties, and wherein, subsequent to (b), the plurality of detectable moieties is removed.

In some cases, the third plurality of labeled nucleotides and the fourth plurality of labeled nucleotides are labeled with a plurality of detectable moieties, and wherein, subsequent to (d), the plurality of detectable moieties is removed.

In some cases, the first plurality of nucleotides and the second plurality of nucleotides are labeled with detectable moieties that are capable of yielding optical signals of a substantially same frequency or color upon excitation.

In some cases, the first plurality of nucleotides and the third plurality of nucleotides are labeled with detectable moieties that are capable of yielding optical signals of a substantially same frequency or color upon excitation.

In some cases, the conditions in (b) and/or (d) comprise reagents to regulate a rate of incorporation of the first plurality of labeled nucleotides, the second plurality of labeled nucleotides, the third plurality of labeled nucleotides, and/or the fourth plurality of labeled nucleotides. In some cases, the conditions in (b) comprise varying strontium, manganese, and/or magnesium concentrations or relative amounts, and/or varying incubation time of the first reaction mixture and/or the second reaction mixture to the first plurality of nucleic acid molecules, the second plurality of nucleic acid molecules, the third plurality of nucleic acid molecules, and the fourth plurality of nucleic acid molecules.

Further provided herein is a method for identifying a nucleic acid sequence, comprising: (a) bringing a substrate comprising a plurality of nucleic acid molecules immobilized at a detection area in contact with a reaction mixture comprising a plurality of nucleotides, under conditions sufficient to incorporate nucleotides of the plurality of nucleotides into sequences hybridized to the plurality of nucleic acid molecules, wherein the plurality of nucleotides are reversibly terminated and labeled, and wherein the plurality of nucleic acid molecules has sequence homology with a template nucleic acid molecule; (b) detecting a set of signals from the detection area, wherein the set of signals is indicative of incorporation of the nucleotides of the plurality of nucleotides; (c) initiating unblocking reactions to remove terminators from the nucleotides of the plurality of nucleotides; and (d) during the unblocking reactions, repeating (a)-(c).

In some cases, (c) comprises bringing the substrate in contact with one or more reducing agents, and washing the one or more reducing agents prior to repeating (a)-(c). In some cases, the one or more reducing agents are phosphine agents.

In some cases, the plurality of nucleotides comprises 3'-OH disulfide reversible terminators.

In some cases, (d) comprises repeating (a)-(c) subsequent to at least 30% completion of the unblocking reactions. In some cases, (d) comprises repeating (a)-(c) subsequent to at least 40% completion of the unblocking reactions. In some cases, (d) comprises repeating (a)-(c) subsequent to at least 50% completion of the unblocking reactions. In some cases, (d) comprises repeating (a)-(c) subsequent to at least 90% completion of the unblocking reactions.

In some cases, (d) comprises repeating (a)-(c) with an additional plurality of nucleotides, wherein the additional plurality of nucleotides are reversibly terminated and labeled, and wherein the additional plurality of nucleotides are of a different type than the plurality of nucleotides. In some cases, the additional plurality of nucleotides and the plurality of nucleotides are labeled with detectable moieties that are capable of yielding optical signals of a substantially same frequency or color upon excitation.

In some cases, the plurality of nucleic acid molecules is immobilized at the detection area via a plurality of primers.

In some cases, the signals are optical signals. In some cases, the signals correspond to a change in impedance, charge, capacitance, current, or conductivity associated with the plurality of nucleic acid molecules.

In some cases, the conditions in (b) comprise reagents to regulate a rate of incorporation of the first plurality of nucleotides. In some cases, the conditions in (b) comprise varying strontium, manganese, and/or magnesium concentrations or relative amounts, and/or varying incubation time of the first reaction mixture to the plurality of nucleic acid molecules.

Reducing or Eliminating Lag Phasing

Provided herein are methods for reducing or eliminating phasing (e.g., lag and/or lead phasing) in analysis of a plurality of nucleic acid molecules, such as during nucleic acid sequencing (e.g., as described herein).

A method may comprise providing a plurality of nucleic acid molecules (e.g., as described herein), which plurality of nucleic acid molecules have sequence identity to one another. The plurality of nucleic acid molecules may be immobilized to a detection area (e.g., as described herein). The plurality of nucleic acid molecules may be brought into contact with a first reaction mixture (e.g., flow) comprising a first plurality of nucleotides of a same canonical base type (e.g., T, A, C, or G containing nucleotides, or analogs thereof, as described herein), under conditions sufficient to incorporate nucleotides of the first plurality of nucleotides into a first plurality of growing strands coupled to a first subset of the plurality of nucleic acid molecules. Some or all of the nucleotides in the first reaction mixture may be labeled nucleotides. A cleavage flow to remove labels from labeled nucleotides (e.g., as described herein) and/or one or more wash flows (e.g., as described herein) may be flowed prior to contacting the plurality of nucleic acid molecules with any subsequent reaction mixture. In some cases, a wash flow may be used to remove unincorporated nucleotides but labels may not be removed after the first reaction mixture is flowed. Subsequently, the plurality of nucleic acid molecules may be brought into contact with a second reaction mixture comprising a second plurality of nucleotides of the same canonical base type, under conditions sufficient to incorporate nucleotides of the second plurality of nucleotides into a second plurality of growing strands coupled to a second subset of the plurality of nucleic acid molecules. The nucleotides of the second mixture may all be unlabeled. Alternatively, at least some nucleotides of the second mixture may be labeled. For example, at least about 1%, 2%, 2.5%, 5%, 10%, or more nucleotides of the second mixture may be labeled. In some cases, the composition of the first reaction mixture and second reaction mixture may be the same (e.g., both reaction mixtures may comprise the same ratio of labeled to unlabeled nucleotides of the same canonical base type, such as about 2.5% labeled nucleotides). In some cases, nucleotides of the first plurality of nucleotides and/or nucleotides of the second plurality of nucleotides may comprise a non-terminated nucleotide. In some cases, the second reaction mixture may be flowed prior to or in absence of detecting a signal (e.g., an optical signal, such as a fluorescent signal) indicative of incorporation of nucleotides of the first plurality of nucleotides. In some cases, in the first and/or second reaction mixture, nucleotides of the same canonical base type are at a greater concentration than nucleotides of another canonical base type. For example, the first and/or second reaction mixture, nucleotides of the same canonical base type are at a greater concentration than nucleotides of another canonical base type. In an example, the first and/or second reaction mixture, nucleotides of the same canonical base type are at a greater concentration than nucleotides of each other canonical base type. The process may be repeated one or more times using nucleotide flows including different canonical base types.

The method may comprise contacting the plurality of nucleic acid molecules with a first reaction mixture comprising nucleotides of a canonical base type, and subsequently contacting the plurality of nucleic acid molecules with a second reaction mixture comprising nucleotides of the same canonical base type. The two flows may be interrupted by one or more intermediary flows (e.g., wash flows, cleavage flows, etc.) that do not comprise nucleotide. The consecutive flows of the same canonical base type may reduce or eliminate phasing by ensuring that most, if not all, of the plurality of nucleic acid molecules have incorporated a nucleotide of the canonical base type at all available incorporation sites (e.g., of growing strands coupled to the plurality of nucleic acid molecules), thus achieving 100% or substantially 100% incorporation rate.

Traditionally, upon contacting the plurality of nucleic acid molecules with a reaction mixture comprising nucleotides of a canonical base type, not all of the available incorporation sites will have incorporated a nucleotide of the canonical base type because of, for example, reaction kinetics and/or other factors that inhibit incorporation. Such incorporation failure events may be more likely when the reaction mixture comprises nucleotides that are fluorescently labeled because the polymerase may not be as compatible with such unnatural nucleotides. Thus, interrogation of the plurality of nucleic acid molecules for that canonical base type (or complement thereof) will conclude at less than 100% incorporation rate, and if a subsequent reaction mixture comprising nucleotides of a different canonical base type is brought into contact with the plurality of nucleic acid molecules, there will be lag phasing. Such lag phasing may eventually lead to deterioration of the sequencing quality and limit read length. Recognized herein is a need for methods that address at least the above-mentioned problems. The methods provided herein can contact the plurality of nucleic acid molecules with consecutive flows of the same canonical base type to ensure that most, if not all, of the plurality of nucleic acid molecules have incorporated a nucleotide of the canonical base type at all available incorporation sites (e.g., of growing strands coupled to the plurality of nucleic acid molecules), thus achieving 100% or substantially 100% incorporation rate and reducing or eliminating lag phasing. Achieving 100% or substantially 100% incorporation rates during interrogation for each canonical base type may further obviate the need for complicated phasing correction algorithms by addressing the problem at the signal source.

In an example flow scheme, a plurality of nucleic acid molecules is contacted with at least the following reaction mixtures in the listed order: a first reaction mixture comprising nucleotides of a first canonical base type; and a second reaction mixture comprising nucleotides of the first canonical base type. In another example flow scheme, a plurality of nucleic acid molecules is contacted with at least the following reaction mixtures in the listed order: a first reaction mixture comprising nucleotides of a first canonical base type, wherein the nucleotides comprise a mixture of labeled and unlabeled nucleotides; and a second reaction mixture comprising nucleotides of the first canonical base type, wherein the nucleotides comprise unlabeled nucleotides. Alternatively or in addition, the subsequent reaction mixture(s) (e.g., second reaction mixture) may comprise labeled nucleotides.

In another example flow scheme, a plurality of nucleic acid molecules is contacted with at least the following reaction mixtures in the listed order: a first reaction mixture comprising nucleotides of a first canonical base type; a wash reaction mixture configured to remove unincorporated nucleotides from the reaction site; and a second reaction mixture comprising nucleotides of the first canonical base type. In another example flow scheme, a plurality of nucleic acid molecules is contacted with at least the following reaction mixtures in the listed order: a first reaction mixture comprising nucleotides of a first canonical base type; a second reaction mixture comprising nucleotides of the first canonical base type; and a wash reaction mixture configured to remove unincorporated nucleotides from the reaction site.

In another example flow scheme, a plurality of nucleic acid molecules is contacted with at least the following reaction mixtures in the listed order: a first reaction mixture comprising nucleotides of a first canonical base type; a cleavage reaction mixture configured to cleave label moieties from labeled nucleotides; and a second reaction mixture comprising nucleotides of the first canonical base type. In another example flow scheme, a plurality of nucleic acid molecules is contacted with at least the following reaction mixtures in the listed order: a first reaction mixture comprising nucleotides of a first canonical base type; a second reaction mixture comprising nucleotides of the first canonical base type; and a cleavage reaction mixture configured to cleave label moieties from labeled nucleotides.

In another example flow scheme, a plurality of nucleic acid molecules is contacted with at least the following reaction mixtures in the listed order: a first reaction mixture comprising nucleotides of a first canonical base type; a wash reaction mixture configured to remove unincorporated nucleotides from the reaction site; a cleavage reaction mixture configured to cleave label moieties from labeled nucleotides; and a second reaction mixture comprising nucleotides of the first canonical base type. In another example flow scheme, a plurality of nucleic acid molecules is contacted with at least the following reaction mixtures in the listed order: a first reaction mixture comprising nucleotides of a first canonical base type; a cleavage reaction mixture configured to cleave label moieties from labeled nucleotides; a wash reaction mixture configured to remove unincorporated nucleotides from the reaction site; and a second reaction mixture comprising nucleotides of the first canonical base type. In another example flow scheme, a plurality of nucleic acid molecules is contacted with at least the following reaction mixtures in the listed order: a first reaction mixture comprising nucleotides of a first canonical base type; a second reaction mixture comprising nucleotides of the first canonical base type; a wash reaction mixture configured to remove unincorporated nucleotides from the reaction site; and a cleavage reaction mixture configured to cleave label moieties from labeled nucleotides. In another example flow scheme, a plurality of nucleic acid molecules is contacted with at least the following reaction mixtures in the listed order: a first reaction mixture comprising nucleotides of a first canonical base type; a second reaction mixture comprising nucleotides of the first canonical base type; a cleavage reaction mixture configured to cleave label moieties from labeled nucleotides; and a wash reaction mixture configured to remove unincorporated nucleotides from the reaction site. In another example flow scheme, a plurality of nucleic acid molecules is contacted with at least the following reaction mixtures in the listed order: a first reaction mixture comprising nucleotides of a first canonical base type; a wash reaction mixture configured to remove unincorporated nucleotides from the reaction site; a second reaction mixture comprising nucleotides of the first canonical base type; and a cleavage reaction mixture configured to cleave label moieties from labeled nucleotides. In another example flow scheme, a plurality of nucleic acid molecules is contacted with at least the following reaction mixtures in the listed order: a first reaction mixture comprising nucleotides of a first canonical base type; a cleavage reaction mixture configured to cleave label moieties from labeled nucleotides; a second reaction mixture comprising nucleotides of the first canonical base type; and a wash reaction mixture configured to remove unincorporated nucleotides from the reaction site. The flow schemes may comprise a cleavage reaction mixture or additional cleavage reaction mixture(s) subsequent to any nucleotide-containing reaction mixture containing labeled nucleotides. For example, the flow schemes may comprise two consecutive cleavage reaction mixtures contacting the plurality of nucleic acid molecules. The flow schemes may comprise a wash reaction mixture or additional wash reaction mixture(s) subsequent to any nucleotide-containing reaction mixture or prior to any nucleotide-containing reaction mixture. For example, the flow schemes may comprise two consecutive wash reaction mixtures contacting the plurality of nucleic acid molecules.

In another example flow scheme, a plurality of nucleic acid molecules is contacted with at least the following reaction mixtures in the listed order: a first reaction mixture comprising nucleotides of a first canonical base type; a wash reaction mixture configured to remove unincorporated nucleotides from the reaction site; a cleavage reaction mixture configured to cleave label moieties from labeled nucleotides; a second reaction mixture comprising nucleotides of the first canonical base type; and a second wash reaction mixture configured to remove unincorporated nucleotides from the reaction site.

The flow schemes may comprise any number of additional reaction mixture(s) comprising nucleotides of the first canonical base type. In an example flow scheme, a plurality of nucleic acid molecules is contacted with at least the following reaction mixtures in the listed order: a first reaction mixture comprising nucleotides of a first canonical base type; a second reaction mixture comprising nucleotides of the first canonical base type; and a third reaction mixture comprising nucleotides of the first canonical base type. In another example flow scheme, a plurality of nucleic acid molecules is contacted with at least the following reaction mixtures in the listed order: a first reaction mixture comprising nucleotides of a first canonical base type, wherein the nucleotides comprise a mixture of labeled and unlabeled nucleotides; a second reaction mixture comprising nucleotides of the first canonical base type, wherein the nucleotides comprise unlabeled nucleotides; and a third reaction mixture comprising nucleotides of the first canonical base type, wherein the nucleotides comprise unlabeled nucleotides. Alternatively or in addition, the subsequent reaction mixture (s) (e.g., second reaction mixture, third reaction mixture) may comprise labeled nucleotides. For example, the flow schemes may comprise 2, 3, 4, 5, 6, 7, 8, 9, 10 or more consecutive reaction mixtures comprising nucleotides of the same canonical base type, which may or may not be interrupted by non-nucleotide containing reaction mixtures (e.g., wash reaction mixtures, cleavage reaction mixtures, etc.).

In some instances, the flow schemes may comprise reaction mixtures comprising more than one canonical base type (e.g., 2 types, 3 types, 4 types), wherein the subsequent reaction mixture also contains the same more than one canonical base type. In another example flow scheme, a plurality of nucleic acid molecules is contacted with at least the following reaction mixtures in the listed order: a first reaction mixture comprising nucleotides of a first canonical base type and a second canonical base type; and a second reaction mixture comprising nucleotides of the first canonical base type and the second canonical base type. In another example flow scheme, a plurality of nucleic acid molecules is contacted with at least the following reaction mixtures in the listed order: a first reaction mixture comprising nucleotides of a first canonical base type and a second canonical base type, wherein the nucleotides comprise a mixture of labeled and unlabeled nucleotides; and a second reaction mixture comprising nucleotides of the first canonical base type and the second canonical base type, wherein the nucleotides comprise unlabeled nucleotides. Alternatively or in addition, the subsequent reaction mixture(s) (e.g., second reaction mixture) may comprise labeled nucleotides.

In some instances, the different reaction mixtures can be contacted with the plurality of nucleic acid molecules under different and/or predetermined reaction conditions. For example, any given reaction mixture may contact the nucleic acid molecules under reaction conditions modulated to expedite incorporation or decrease speed of incorporation. Reaction conditions may be modulated by adjusting, for example, reaction volume, incubation time, nucleotide concentration, temperature, pH level, salt concentration, enzyme concentration, magnesium concentration, manganese concentration, strontium concentration, other catalyst concentrations, crowding or viscosity reagent concentrations, reaction mixture dispense velocity, and other factors.

In an example, the first reaction mixture may contact the plurality of nucleic acid molecules under a first set of conditions and the second reaction mixture may contact the nucleic acid molecules under a second set of conditions, wherein the first set of conditions and/or the second set of conditions are modulated to allow the second reaction mixture to have a more rapid incorporation and/or otherwise higher incorporation rate than the first reaction mixture. For example, the second set of conditions may comprise higher concentration of nucleotides in the reaction mixture, lower concentration of labeled nucleotides in the reaction mixture compared to unlabeled nucleotides, longer incubation time, lower strontium concentrations, higher manganese concentrations, higher magnesium concentrations, higher temperature, and/or a combination thereof relative to the first set of conditions. Other factors such as salt concentrations, crowding or viscosity reagent concentrations, pH levels, reaction mixture dispense velocities, and the like may also be adjusted. For example, the second set of conditions may be configured to accelerate incorporation (e.g., as described elsewhere herein). Alternatively or in addition, the first set of conditions may be configured to decelerate or inhibit incorporation (e.g., as described elsewhere herein).

In some instances, the nucleotide concentration for the reaction mixture with the higher incorporation rate may be optimized to be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, 1000% or greater than in the other reaction mixture. In some instances, the nucleotide concentration(s) for the first and/or second reaction mixture(s) may be optimized to be between about 100 nanomoles per liter (nM) to about 20 micromoles per liter (μM). In some instances, the nucleotide concentration (s) for the first and/or second reaction mixture(s) may be optimized to be at least about 10 nM, 20 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, 1000 nM (or 1 μM), 2 μM, 3 μM, 4 μM, 5 μM, 6 μM, 7 μM, 8 μM, 9 μM, 10 μM, 11 μM, 12 μM, 13 μM, 14 μM, 15 μM, 16 μM, 17 μM, 18 μM, 19 μM, 20 μM, 30 μM, 40 μM, 50 μM, 60 μM, 70 μM, 80 μM, 90 μM, 100 μM or greater. Alternatively or in addition, the nucleotide concentration(s) for the first and/or second reaction mixture(s) may be optimized to be at most about 100 μM, 90 μM, 80 μM, 70 μM, 60 μM, 50 μM, 40 μM, 30 μM, 20 μM, 19 μM, 18 μM, 17 μM, 16 μM, 15 μM, 14 μM, 13 μM, 12 μM, 11 μM, 10 μM, 9 μM, 8 μM, 7 μM, 6 μM, 5 μM, 4 μM, 3 μM, 2 μM, 1 μM (or 1000 nM), 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM or less.

In some instances, a salt concentration for the reaction mixture with the higher incorporation rate may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, or 1000% greater than in the other reaction mixture. Alternatively, a salt concentration for the reaction mixture with the lower incorporation rate may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, or 1000% greater than in the other reaction mixture. In some instances, salt concentration(s) for the first and/or second reaction mixture (s) may be optimized to be between about 0 millimoles per liter (mM) to about 500 mM. In some instances, the salt concentration(s) for the first and/or second reaction mixture (s) may be optimized to be at least about 0 mM, 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 30 mM, 40 mM, 50 mM, 60 mM, 70 mM, 80 mM, 90 mM, 100 mM, 200 mM, 300 mM, 400 mM, 500 mM, 600 mM, 700 mM, 800 mM, 900 mM, 1000 mM or greater. Alternatively or in addition, the salt concentration(s) for the first and/or second reaction mixture (s) may be optimized to be at most about 1000 mM, 900 mM, 800 mM, 700 mM, 600 mM, 500 mM, 400 mM, 300 mM, 200 mM, 100 mM, 90 mM, 80 mM, 70 mM, 60 mM, 50 mM, 40 mM, 30 mM, 20 mM, 19 mM, 18 mM, 17 mM, 16 mM, 15 mM, 14 mM, 13 mM, 12 mM, 11 mM, 10 mM, 9 mM, 8 mM, 7 mM, 6 mM, 5 mM, 4 mM, 3 mM, 2 mM, 1 mM or less.

In some instances, the crowding or viscosity reagent (e.g., polyethylene glycol (PEG), polyvinylpyrrolidone (PVP), Dextran, Ficoll, etc.) concentration(s) for the first and/or second reaction mixture(s) may be optimized to be between about 0% to about 3%. In some instances, the crowding or viscosity reagent concentration(s) for the first and/or second reaction mixture(s) may be optimized to be at least about 0%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0% or greater. Alternatively or in addition, the crowding or viscosity reagent concentration(s) for the first and/or second reaction mixture (s) may be optimized to be at most about 5.0%, 4.9%, 4.8%, 4.7%, 4.6%, 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or less.

In some instances, the magnesium concentration for the reaction mixture with the higher incorporation rate may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, or 1000% greater than in the other reaction mixture. In some instances, the magnesium concentration(s) for the first and/or second reaction mixture(s) may be optimized between about 50 micromoles per liter (μM) to about 5 millimoles per liter (mM). In some instances, the magnesium concentration(s) for the first and/or second reaction mixture(s) may be optimized to at least about 10 μM, 20 μM, 30 μM, 40 μM, 50 μM, 60 μM, 70 μM, 80 μM, 90 μM, 100 μM, 200 μM, 300 μM, 400 μM, 500 μM, 600 μM, 700 μM, 800 μM, 900 μM, 1000 μM (or 1 mM), 1.1 mM, 1.2 mM, 1.3 mM, 1.4 mM, 1.5 mM, 1.6 mM, 1.7 mM, 1.8 mM, 1.9 mM, 2.mM, 2.1 mM, 2.2 mM, 2.3 mM, 2.4 mM, 2.5 mM, 2.6 mM, 2.7 mM, 2.8 mM, 2.9 mM, 3 mM, 3.1 mM, 3.2 mM, 3.3 mM, 3.4 mM, 3.5 mM, 3.6 mM, 3.7 mM, 3.8 mM, 3.9 mM, 4 mM, 4.1 mM, 4.2 mM, 4.3 mM, 4.4 mM, 4.5 mM, 4.6 mM, 4.7 mM, 4.8 mM, 4.9 mM, 5 mM, 6, mM, 7 mM, 8 mM, 9 mM, 10 mM, 11 mM, 12 mM, 13 mM, 14 mM, 15 mM, 16 mM, 17 mM, 18 mM, 19 mM, 20 mM, 30 mM, 40 mM, 50 mM, or greater. Alternatively or in addition, the magnesium concentration(s) for the first and/or second reaction mixture(s) may be optimized to at most about 50 mM, 50 mM, 30 mM, 20 mM, 19 mM, 18 mM, 17 mM, 16 mM, 15 mM, 14 mM, 13 mM, 12 mM, 11 mM, 10 mM, 9 mM, 8 mM, 7 mM, 6 mM, 5 mM, 4.9 mM, 4.8 mM, 4.7 mM, 4.6 mM, 4.5 mM, 4.4 mM, 4.3 mM, 4.2 mM, 4.1 mM, 4 mM, 3.9 mM, 3.8 mM, 3.7 mM, 3.6 mM, 3.5 mM, 3.4 mM, 3.3 mM, 3.2 mM, 3.1 mM, 3 mM, 2.9 mM, 2.8 mM, 2.7 mM, 2.6 mM, 2.5 mM, 2.4 mM, 2.3 mM, 2.2 mM, 2.1 mM, 2 mM, 1.9 mM, 1.8 mM, 1.7 mM, 1.6 mM, 1.5 mM, 1.4 mM, 1.3 mM, 1.2 mM, 1.1 mM, 1 mM (1000 μM), 900 μM, 800 μM, 700 μM, 600 μM, 500 μM, 400 μM, 300 μM, 200 μM, 100 μM, 90 μM, 80 μM, 70 μM, 60 μM, 50 μM, 40 μM, 30 μM, 20 μM, 10 μM or less.

In some instances, the manganese concentration for the reaction mixture with the higher incorporation rate may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, or 1000% greater than in the other reaction mixture.

In some instances, the strontium concentration in the reaction mixture with the lower incorporation rate may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, or 1000% greater more than in the other reaction mixture.

In some instances, the incubation time of the reaction mixture with the higher incorporation rate may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, or 1000% greater than of the other reaction mixture. In some instances, the incubation time(s) provided for the first and/or second reaction mixture (s) may be optimized between about 1 second to about 30 seconds. In some instances, the incubation time(s) provided for the first and/or second reaction mixture(s) may be optimized to be at least about on the order of at least about $10^{-3}$ seconds, $10^{-2}$ seconds, $10^{-1}$ seconds, 1 second, 10 seconds, $10^{2}$ seconds, or $10^{3}$ seconds. Alternatively or in addition, the incubation time(s) provided for the first and/or second reaction mixture(s) may be optimized to be at most about on the order of $10^{3}$ seconds, $10^{2}$ seconds, 10 seconds, 1 second, $10^{4}$ seconds, $10^{-2}$ seconds, $10^{-3}$ seconds or less.

In some instances, the volume for the reaction mixture with the higher incorporation rate that is provided to the plurality of nucleic acid molecules may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, or 1000% greater than for the other reaction mixture provided to the plurality of nucleic acid molecules. In some instances, the volume(s) for the first and/or second reaction mixture(s) that is provided to the plurality of nucleic acid molecules may be optimized between about 100 microliters (μL) to about 6 milliliters (mL). In some instances, the volume(s) for the first and/or second reaction mixture(s) that is provided to the plurality of nucleic acid molecules may be optimized to be at least about 10 μL, 20 μL, 30 μL, 40 μL, 50 μL, 60 μL, 70 μL, 80 μL, 90 μL, 100 μL, 200 μL, 300 μL, 400 μL, 500 μL, 600 μL, 700 μL, 800 μL, 900 μL, 1000 μL (or 1 mL), 1.1 mL, 1.2 mL, 1.3 mL, 1.4 mL, 1.5 mL, 1.6 mL, 1.7 mL, 1.8 mL, 1.9 mL, 2.mL, 2.1 mL, 2.2 mL, 2.3 mL, 2.4 mL, 2.5 mL, 2.6 mL, 2.7 mL, 2.8 mL, 2.9 mL, 3 mL, 3.1 mL, 3.2 mL, 3.3 mL, 3.4 mL, 3.5 mL, 3.6 mL, 3.7 mL, 3.8 mL, 3.9 mL, 4 mL, 4.1 mL, 4.2 mL, 4.3 mL, 4.4 mL, 4.5 mL, 4.6 mL, 4.7 mL, 4.8 mL, 4.9 mL, 5 mL, 5.1 mL, 5.2 mL, 5.3 mL, 5.4 mL, 5.5 mL, 5.6 mL, 5.7 mL, 5.8 mL, 5.9 mL, 6, mL, 7 mL, 8 mL, 9 mL, 10 mL, 11 mL, 12 mL, 13 mL, 14 mL, 15 mL, 16 mL, 17 mL, 18 mL, 19 mL, 20 mL, 30 mL, 40 mL, 50 mL, or greater. Alternatively or in addition, the volume(s) for the first and/or second reaction mixture(s) that is provided to the plurality of nucleic acid molecules may be optimized to be at most about 50 mL, 50 mL, 30 mL, 20 mL, 19 mL, 18 mL, 17 mL, 16 mL, 15 mL, 14 mL, 13 mL, 12 mL, 11 mL, 10 mL, 9 mL, 8 mL, 7 mL, 6 mL, 5.9 mL, 5.8 mL, 5.7 mL, 5.6 mL, 5.5 mL, 5.4 mL, 5.3 mL, 5.2 mL, 5.1 mL, 5 mL, 4.9 mL, 4.8 mL, 4.7 mL, 4.6 mL, 4.5 mL, 4.4 mL, 4.3 mL, 4.2 mL, 4.1 mL, 4 mL, 3.9 mL, 3.8 mL, 3.7 mL, 3.6 mL, 3.5 mL, 3.4 mL, 3.3 mL, 3.2 mL, 3.1 mL, 3 mL, 2.9 mL, 2.8 mL, 2.7 mL, 2.6 mL, 2.5 mL, 2.4 mL, 2.3 mL, 2.2 mL, 2.1 mL, 2 mL, 1.9 mL, 1.8 mL, 1.7 mL, 1.6 mL, 1.5 mL, 1.4 mL, 1.3 mL, 1.2 mL, 1.1 mL, 1 mL (1000 μL), 900 μL, 800 μL, 700 μL, 600 μL, 500 μL, 400 μL, 300 μL, 200 μL, 100 μL, 90 μL, 80 μL, 70 μL, 60 μL, 50 μL, 40 μL, 30 μL, 20 μL, 10 μM or less.

In some instances, the temperature in the reaction conditions for the reaction mixture with the higher incorporation rate may be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 300%, 400%, 500%, or 1000% greater than in the reaction conditions for the other reaction mixture. In some instances, the temperature(s) in the reaction conditions for the first and/or second reaction mixture(s) may be optimized between about ambient temperature or room temperature (e.g., 20-25 degrees Celsius) to about 60 degrees Celsius (° C.). In some instances, the temperature(s) in the reaction conditions for the first and/or second reaction mixture(s) may be optimized to be at least about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65° C. or higher. Alternatively or in addition, the temperature(s) in the reaction conditions for the first and/or second reaction mixture(s) may be optimized to at most about 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18° C., or less.

In some instances, the pH level(s) in the first and/or second reaction mixture(s) may be optimized between about 6.0 and 9.5. In some instances, the pH level(s) for the first and/or second reaction mixture(s) may be optimized to be at least about 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0 or higher. Alternatively or in addition, the pH level(s) first and/or second reaction mixture (s) may be optimized to be at most about 10.0, 9.9, 9.8, 9.7, 9.6, 9.5, 9.4, 9.3, 9.2, 9.1, 9.0, 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5 or less.

In some instances, the dispense velocity(ies) of the first and/or second reaction mixture(s) to the plurality of nucleic acid molecule may be optimized to achieve a desired incorporation rate after a given flow of the respective reaction mixture. In some instances, the first and/or second reaction mixture(s) may be distributed to the plurality of nucleic acid molecules using relative motion between a dispensing location for the reaction mixture(s) and a substrate wherein the plurality of nucleic acid molecules is disposed on the substrate (e.g., immobilized adjacent thereto or otherwise coupled thereto). In some instances, the velocity of the relative motion may be optimized. In some instances, the relative motion may comprise linear motion. Alternatively or in addition, the relative motion may comprise non-linear motion. In some instances, the angular velocity(ies) between dispensing location(s) the first and/or second reaction mixture(s) and the substrate may be optimized to be between about 50 rotations per minute (rpm) to about 1200 rpm. In some instances, an angular velocity of the substrate that is rotating with respect to an axis may be optimized to be between from about 50 rpm to about 1200 rpm. In some instances, a linear velocity of the substrate that is moving with respect to the dispensing location may be optimized.

In some instances, the fraction of the labeled to unlabeled nucleotides in the reaction mixture may be selected such as to provide a linear relationship between number of consecutive nucleotides (of the same canonical base type) incorporated to a growing strand and signal strength or intensity, for homopolymer detection and resolution.

The flow schemes described herein may be repeated with reaction mixtures comprising nucleotides of different canonical base types for any number of times. For example, a flow cycle may comprise cycling through a flow scheme for each of the four canonical base types.

In the flow schemes described herein, a detection operation may occur at any time subsequent to flowing any reaction mixture containing labeled nucleotides, such as subsequent to flowing a wash reaction mixture after the reaction mixture containing labeled nucleotides. The detection operation may occur at any time prior to flowing a reaction mixture containing labeled nucleotides of a different canonical base type.

Accelerating Nucleic Acid Sequence Identification

The present disclosure also provides systems and methods for accelerating nucleic acid sequence identification. A method for identifying a nucleic acid sequence may comprise initiating a new sequencing read cycle or portion thereof (e.g., a reaction mixture flow) prior to completion of cleavage of a blocking group of a reversibly terminated nucleotide incorporated from an immediately previous cycle or portion thereof. That is, a new sequencing read cycle or portion thereof may be initiated during cleavage of the blocking group.

A nucleotide in a reaction mixture introduced to a nucleic acid molecule for incorporation into a growing strand may be reversibly terminated, as described elsewhere herein. Terminated nucleotides may terminate primer extension reactions and ensure that only one, and not more than one, base is incorporated during a given sequencing cycle. Reversibly terminated nucleotides may be accepted by polymerases and incorporated into growing nucleic acid strands analogously to non-reversibly terminated nucleotides. A reversible terminator may comprise a blocking group attached to a 3' end of a nucleotides, such as to the 3'-oxygen atom of a sugar moiety (e.g., a pentose) of a nucleotide. For example, a blocking group may be an azidomethyl or disulfide blocking group. Examples of 3'-O-blocked reversible terminators include 3'-O-(2-nitrobenzyl) reversible terminators, 3'-O-azidomethyl reversible terminators, 3'-$ONH_2$ reversible terminators, 3'-O-allyl reversible terminators, and 3'-O-(2-cyanoethyl) reversible terminators. The blocking groups may be attached to the nucleotide via a cleavable linker. In some instances, the blocking groups may comprise a reporter moiety (e.g., dye moiety). Alternatively, the reporter moiety may be attached to the nucleotide at a different location (e.g., at a nucleobase) via an independent linker. In some instances, the linker for the blocking group and the linker for the dye may be the same type of linker and/or otherwise be cleavable via the same stimulus (e.g., cleaving agent). Cleavable linkers can include, for example, disulfide linkers and fluoride-cleavable linkers. The reversibly terminated nucleotide may be unblocked, such as by cleaving the blocking group (e.g., using a cleaving reagent or irradiation), to reverse the termination. Unblocking may be facilitated by introducing one or more cleaving agents. The cleaving agent may be dependent on the unblocking group present. For example, reducing agents may be used to cleave disulfide bonds or other reductive cleavage groups. Reducing agents include, but are not limited to, phosphine compounds, water soluble phosphines, nitrogen containing phosphines and salts and derivatives thereof, dithioerythritol (DTE), dithiothreitol (DTT) (cis and trans isomers, respectively, of 2,3-dihydroxy-1,4-dithiolbutane), 2-mercaptoethanol or β-mercaptoethanol (BME), 2-mercaptoethanol or aminoethanethiol, glutathione, thioglycolate or thioglycolic acid, 2,3-dimercaptopropanol and tris (2-carboxyethyl) phosphine (TCEP), tris(hydroxymethyl)phosphine (THP) and p-[tris(hydroxymethyl)phosphine] propionic acid (THPP). A phosphine reagent may include triaryl phosphines, trialkyl phosphines, sulfonate containing and carboxylate containing phosphines and derivatized water soluble phosphines. In another example, such as for 2-cyanoethyl blocking groups and/or cyanoethyl ester linkers, fluoride ions (e.g., solution comprising tetrabutylammonium fluoride (TBAF), etc.) can be used as cleaving agents. See, e.g., Diana C. Knapp et al., *Fluoride-Cleavable, Fluorescently Labelled Reversible Terminators: Synthesis and Use in Primer Extension,* 17 Chem. Eur. J. 2903-15 (2011), and Diana C. Knapp et al., *Fluorescent Labeling of (Oligo) Nucleotides by a New Fluoride Cleavable Linker Capable of Versatile Attachment Modes,* 21 Bioconjugate Chem. 1043-55 (2010), which are entirely incorporated herein by reference.

Unblocking reactions such as those described above may be relatively slow, and may take up to a minute or more to complete. Furthermore, such unblocking process may occur asymptotically (e.g., of a natural log) across a bulk number of strands. For example, it may take approximately 5 times as long to achieve 99.33% (e.g., $1-1/(e^5)$) completion of unblocking as it takes to get 63% (e.g., $1-1/e$) completion of unblocking in a colony. In standard reversibly terminated sequencing-by-synthesis (SBS) schemes, the next strand extension cycle may typically be initiated after unblocking is completely finished (e.g., ~100% finished) in order to keep the growing strands of the nucleic acid molecules (e.g., in a colony) in phase. For example, if only 99% of the nucleic acid molecules have been unblocked, the remaining 1% will lag in phase by 1 base and produce conflicting signals during detection. Such lags may be compounded and/or carried over with each consecutive cycle. Therefore, waiting for the unblocking reactions to complete causes significant delay in, and increases, overall sequencing time, as the limited reaction site (e.g., in the flow cell) remains occupied during such waiting time. Expensive imaging systems may also be caused to go into standby mode until the reaction is complete, although, in some SBS schemes, it may be theoretically possible to image during cleavage of reversible terminators by cleaving only the blocking groups without cleaving the dye and separately cleaving the dye linker after imaging.

Provided are methods for sequencing that comprise initiating a new sequencing read cycle prior to completion of cleavage of the blocking group of a reversibly terminated nucleotide incorporated from a previous cycle. Such methods may be used in conjunction with the various reaction mixture flow schemes described herein to avoid the phase lagging problems that can otherwise arise from prematurely initiating the new sequencing read cycle prior to complete cleavage.

Figure 5:
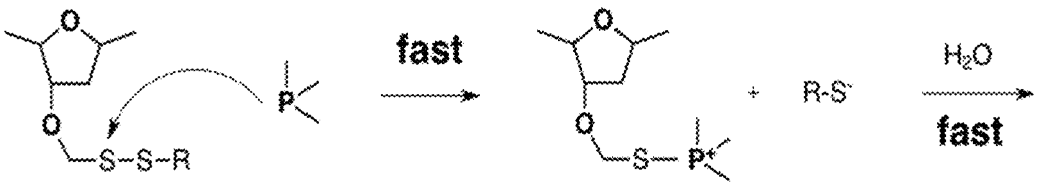
FIG. 5 illustrates an example of a 3'-disulfide terminated nucleotide and a cleavage scheme of the same.
Figure 5:
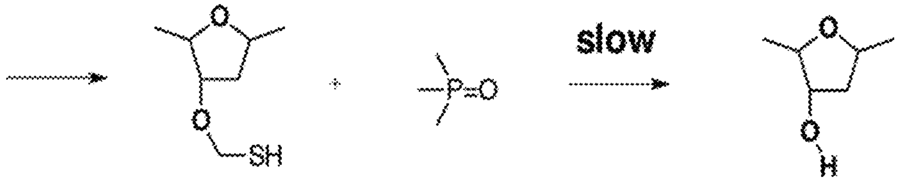
Figure 5:
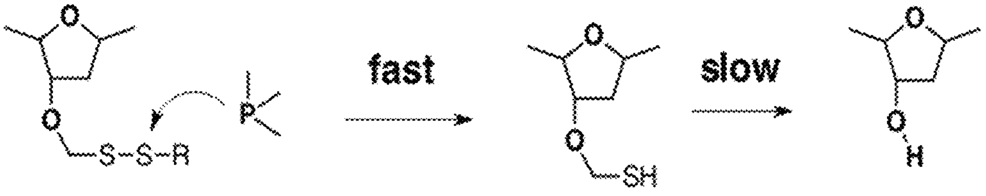

In some instances, the nucleotides of the present disclosure may be 3'-disulfide terminated nucleotides. FIG. 5 illustrates an example of a 3'-disulfide terminated nucleotide and a cleavage scheme of the same. Provided is a 3'-disulfide terminated nucleotide 508. To unblock the terminated nucleotide 508, unblocking reagents 502 may be introduced. For example, the unblocking reagents may be reducing reagents, such as phosphine reagents (e.g., THP or TCEP). The blocking 3'-disulfide residues are asymmetric and provide two potential sites of attack of the phosphorus of the unblocking reagent, as shown in panels A and B, respectively. In both cases, however, the initial reaction is fast and irreversible, leading in both cases to intermediate compound 510, which then hydrolyzes in a relatively slow reaction to yield the 3' unblocked primer 507, which is now available for a subsequent polymerase extension reaction. In panel A, there is another intermediate compound 509, which is converted to the intermediate compound 510 with the addition of $H_2O$. As shown in both panels A and B, the rate-limiting conversion (e.g., "slow") of intermediate compound 510 to primer 507 does not require the presence of the reducing reagents 502. Thus, removal of the excess reducing reagents 502 from the reaction mixture after a relatively short incubation time will not prevent or otherwise slow the unblocking process beyond the expected rate limiting rate.

Figure 6:
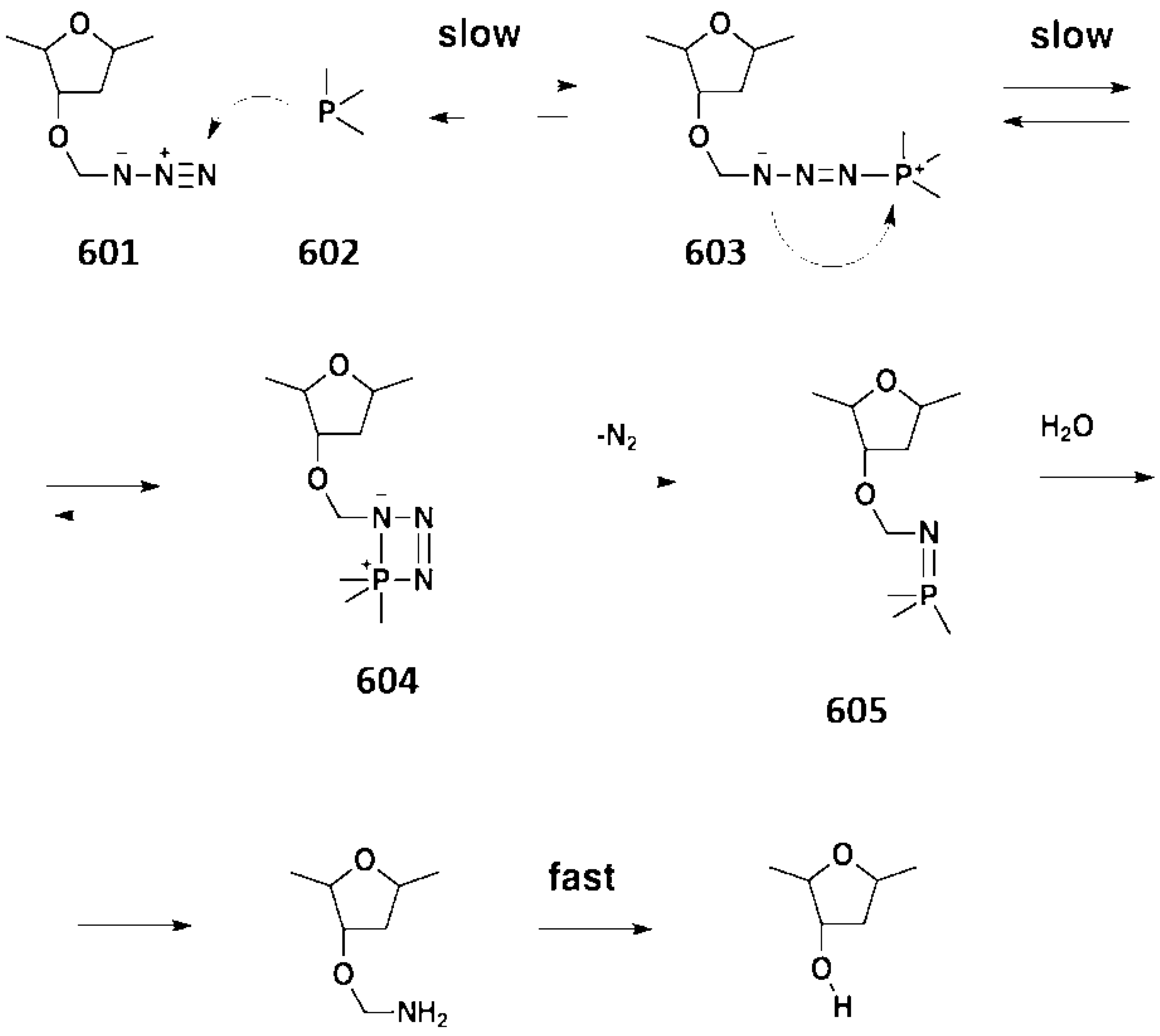
FIG. 6 illustrates an example of a 3'-azidomethyl terminated nucleotide and a cleavage scheme of the same.
Figure 7A:
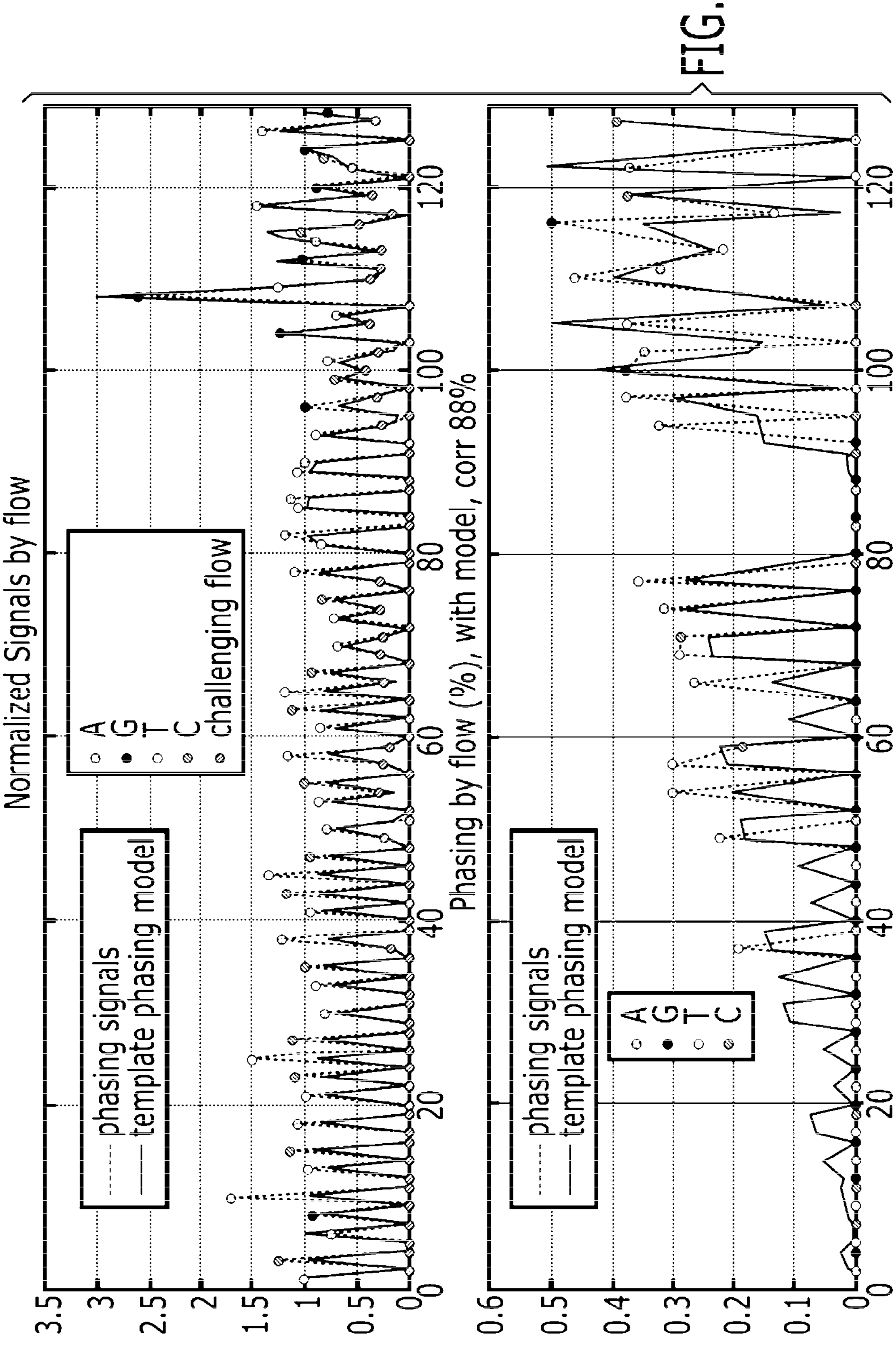
FIGS. 7A-7D show the normalized signals detected by imaging by flow (upper panel) and the % phasing by flow (lower panel) for protocols A (FIG. 7A), B (FIG. 7B), C (FIG. 7C), and D (FIG. 7D) against template TF5, as described in Example 3 herein.
Figure 7B:
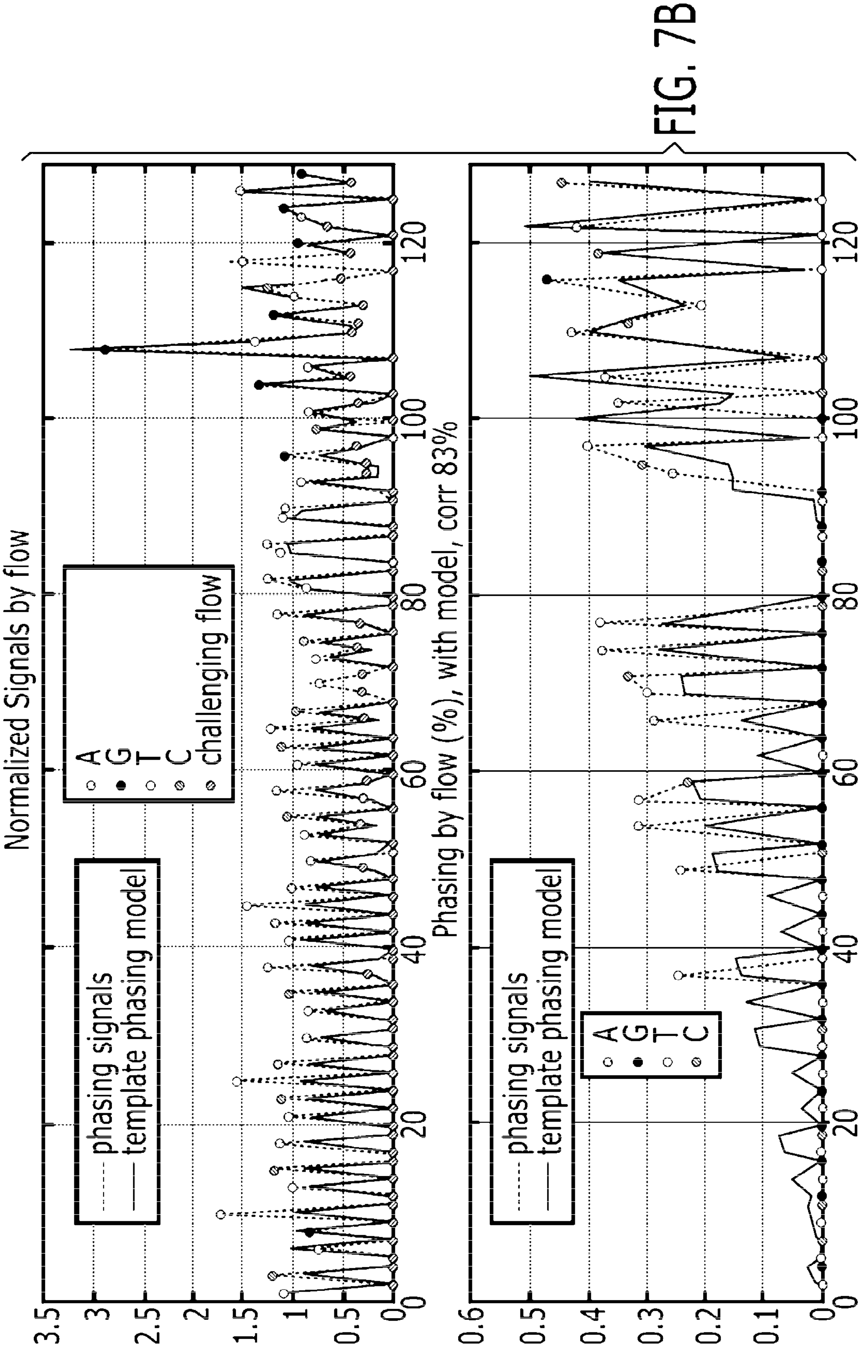
Figure 7C:
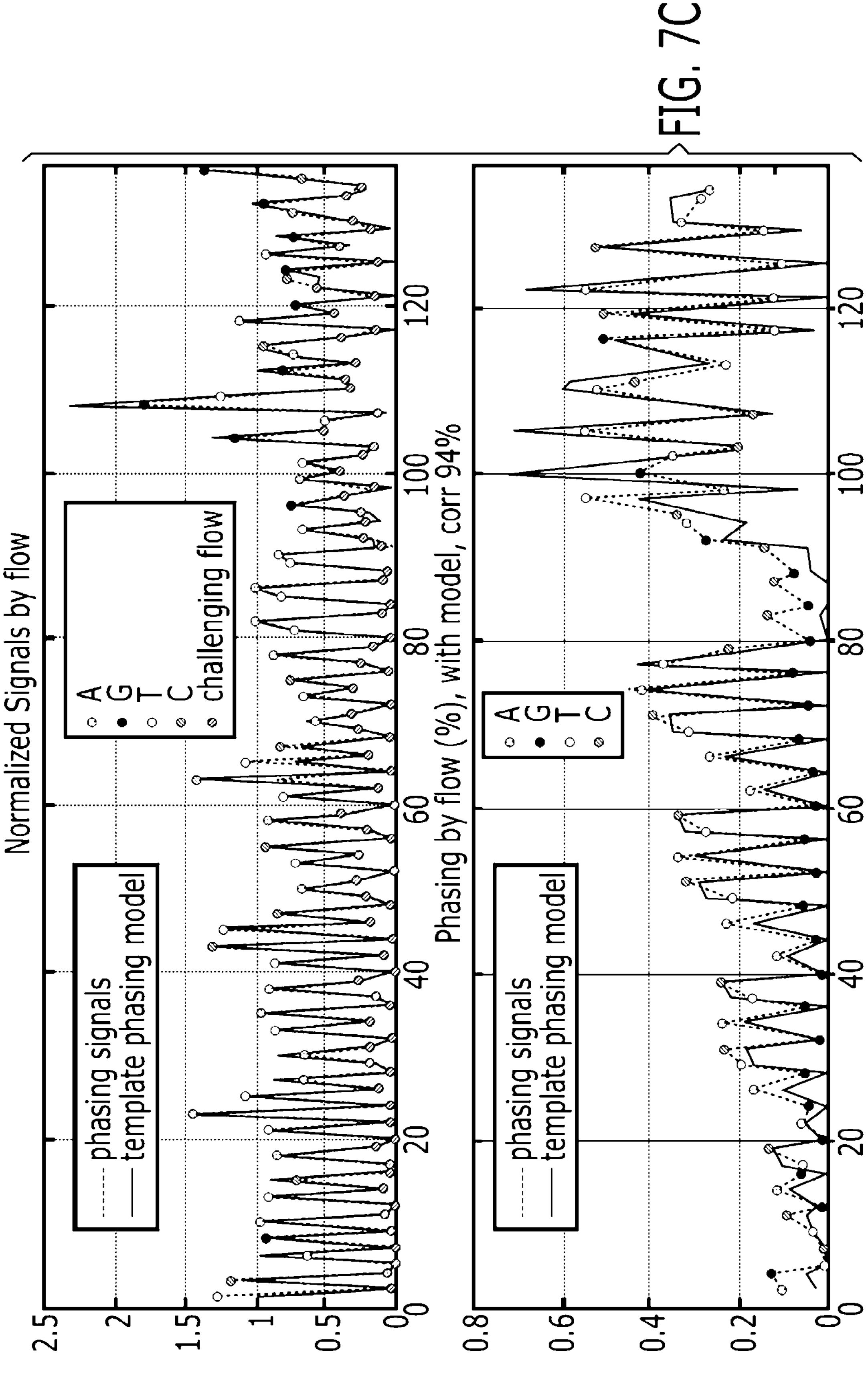
Figure 7D:
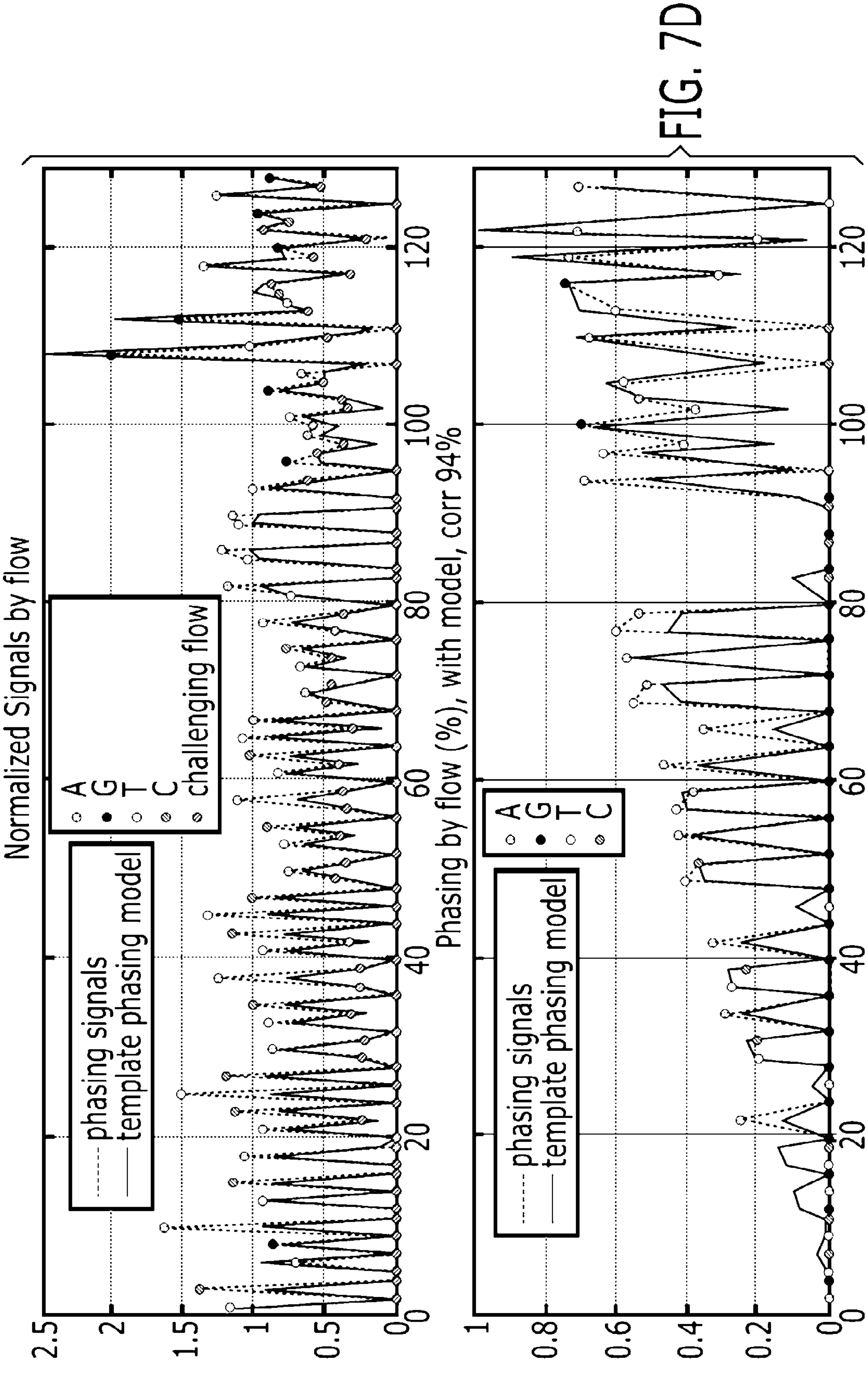

In some instances, the nucleotides of the present disclosure may be 3'-azidomethyl terminated nucleotides. FIG. 6 illustrates an example of a 3'-azidomethyl terminated nucleotide and a cleavage scheme of the same. Provided is a 3'-azidomethyl terminated nucleotide 601. To unblock the terminated nucleotide 601, unblocking reagents 602 may be introduced. For example, the unblocking reagents may be reducing reagents, such as phosphine reagents (e.g., THP or TCEP). Upon introduction of the unblocking reagents 602, intermediate compound 603 is formed in a relatively slow and reversible process, which then rearranges to cyclic structure 604 in still another relatively slow and reversible process. Cyclic structure 604 can lose nitrogen to result in intermediate compound 605, which can rapidly hydrolyze to intermediate compound 606. After another relatively rapid hydrolysis, 3' unblocked primer 607 is formed. The rate limiting step(s) may be the reversible reactions that transform the terminated nucleotide 601 to cyclic compound 604. For example, an excess of reducing reagents 602 may be added to drive the reversible reactions forward. Removal of reducing agents 602 prior to completion of the conversion to cyclic compound 604 may yield less amounts of the final product, the 3' unblocked primer 607.

Provided herein are methods for sequencing that comprise initiating a new sequencing read cycle prior to completion of cleavage of the blocking group of a reversibly terminated nucleotide incorporated from a previous cycle. Such methods may be used in conjunction with the various reaction mixture flow schemes described herein to avoid phase lagging problems.

As described elsewhere herein, a method for nucleic acid sequence identification may comprise providing a plurality of nucleic acid molecules immobilized at a detection area, wherein the plurality of nucleic acid molecules have sequence homology with a template nucleic acid molecule. The plurality of nucleic acid molecules may then be brought in contact with a first reaction mixture comprising a first plurality of nucleotides and a third plurality of nucleotides, under conditions sufficient to incorporate first nucleotides of the first plurality of nucleotides and/or third nucleotides of the third plurality of nucleotides into first sequences hybridized and complementary to a first subset of the plurality of nucleic acid molecules. The conditions may comprise, for example, reagents to regulate a rate of incorporation of the first plurality of nucleotides. For example, the conditions may comprise varying strontium, manganese, and/or magnesium concentrations or relative amounts, and/or varying incubation time of the first reaction mixture to the plurality of nucleic acid molecules. The first nucleotides and/or third nucleotides may be incorporated into the first sequences at a given open position across the first subset of the plurality of nucleic acid molecules. The first plurality of nucleotides and the third plurality of nucleotides may be of different canonical types. All or a portion of the first plurality of nucleotides and/or the third plurality of nucleotides may be labeled. Alternatively, the first plurality of nucleotides and/or the third plurality of nucleotides may be unlabeled. Similarly, all or a portion of the first plurality of nucleotides and/or the third plurality of nucleotides may be reversibly terminated (e.g., as described herein). At a first detection event, signals (e.g., optical signals, or signals that correspond to a change in impedance, charge, capacitance, current, or conductivity associated with the plurality of nucleic acid molecules) indicative of incorporation of the first nucleotides and/or the third nucleotides may be detected in the detection area (e.g., as described herein). In an example, the first plurality of nucleotides may each comprise an adenine nucleobase (A) and the third plurality of nucleotides may each comprise a thymine nucleobase (T), such that the first reaction mixture comprises a mix of A and T bases, and the first detection may detect signals that are indicative of incorporation of either A or T. For example, nucleotides comprising A bases may be labeled with a first label and nucleotides comprising T bases may be labeled with a second label, where the first label is different than the second label, and signals corresponding to labeled A- and T-containing nucleotides may be detected (e.g., as described herein). In another example, nucleotides comprising A bases may be labeled with a first label and nucleotides comprising T bases may be labeled with a second label, where the first label is the same as the second label, and signals corresponding to labeled A- and T-containing nucleotides may be detected (e.g., as described herein).

Subsequent to detection of incorporation of nucleotides from the first reaction mixture (and, in some cases, one or more wash or cleavage flows, as described herein), the plurality of nucleic acid molecules may be brought in contact with a second reaction mixture comprising a fourth plurality of nucleotides that are labeled and a fifth plurality of nucleotides, where the fifth plurality of nucleotides are of a same type as the first plurality of nucleotides. This may be performed under conditions sufficient to incorporate the fourth nucleotides or fifth nucleotides into second sequences hybridized and complementary to a second subset of the plurality of nucleic acid molecules (e.g., as described herein). The fourth nucleotides and fifth nucleotides may be incorporated into the second sequences at the same given open position across the second subset of the plurality of nucleic acid molecules. The first, third, and fourth plurality of nucleotides may be of different types. At a second detection event, signals (e.g., as described herein) indicative of the fourth nucleotides and/or fifth nucleotides being incorporated into the second sequences may be detected from the detection area. For example, the fourth plurality of nucleotides may comprise cytosine nucleobases (C), such that the second reaction mixture comprises A and C bases, and the second detection event detects signals that are indicative of incorporation of either A or C. The first, third, and fourth plurality of nucleotides may be labeled with detectable moieties that yield optical signals of substantially the same color or frequency. A digital output may be computed from a difference between the second detection and the first detection to determine which of the four base types are in the given position in the sequence, as described elsewhere herein.

Subsequent to detection of incorporation of nucleotides from the second reaction mixture (and, in some cases, one or more wash or cleavage flows, as described herein), the plurality of nucleic acid molecules may be brought in contact with a third reaction mixture comprising a second plurality of nucleotides, under conditions sufficient to incorporate second nucleotides of the second plurality of nucleotides into third sequences complementary to a third subset of the plurality of nucleic acid molecules different than the first and second subsets. The second nucleotides may be incorporated into the third sequences at the same given open position across the third subset of the plurality of nucleic acid molecules. The second plurality of nucleotides may be unlabeled. The second plurality of nucleotides may also be reversibly terminated (e.g., as described herein). The third subset of the plurality of nucleic acid molecules may comprise a greater number of nucleic acid molecules than the first and second subsets, individually and/or combined, of the plurality of nucleic acid molecules.

After complete incorporation (e.g., all of the plurality of nucleic acid molecules have incorporated a base in the given open position whether labeled or unlabeled), reversibly terminated, incorporated nucleotides may be unblocked and labels removed. The method may then be repeated to identify a subsequent base in the sequence. The method may be repeated as many times as needed to identify subsequent bases one base at a time, such as at least 2, 3, 4, 5, 6, 7, 8, 9, 10, 15, 20, 25, 30, 35, 40, 45, 50, 100 cycles or more. Alternatively or in addition, the method may be repeated at most about 100, 50, 45, 40, 35, 30, 25, 20, 15, 10, 9, 8, 7, 6, 5, 4, 3, 2 or 1 times.

As described with respect to FIG. 5, such as when using disulfide terminated nucleotides, during an unblocking process, after the reducing agents (e.g., 502) are introduced, in a first part of the unblocking process, labels (e.g., dyes) may rapidly cleave and the reversible terminators may rapidly undergo conversion to the intermediate compound, at which point, in a second part of the unblocking reaction, the unblocking process slows down as the intermediate compound slowly reverts to the natural 3' state to become available for further incorporations. That is, the number of nucleic acid molecules available for further incorporations will increase asymptotically (e.g., slowly) in the population of the plurality of nucleic acid molecules. However, the presence of the reducing agents is not needed for the second part of such reaction. Thus, the method may comprise, after the first part of the reaction (e.g., cleavage of the disulfide link and formation of the intermediate compound), washing the reducing agents and dye molecules, and without waiting for the completion of the relatively slow unblocking reaction, initiating the next cycle (e.g., repeating the above operations). Initiating the next cycle may comprise flowing in the first reaction mixture comprising the labeled, reversibly terminated nucleotides under conditions sufficient to only fractionally incorporate the labeled nucleotides. Such pre-completion initiation of the next cycle is possible because the first flow in the sequencing schemes described herein require only fractional incorporation (e.g., does not require all incorporation sites to be available), and because the dyes from the previous cycle have been cleaved and washed and will not interfere with current signals during detection. As the reducing agents have also been washed from the reaction site, the newly incorporated, reversibly terminated nucleotides are not cleaved.

Beneficially, the sequencing-by-synthesis schemes described in the present disclosure may use labeled nucleotides that comprise a label (e.g., dye moiety) coupled to an OH— site (e.g., as opposed to the base) of a nucleotide in flows where fractional incorporation is the objective (e.g., the first flow). Such a configuration, in which a potentially large and bulky dye molecule may be coupled to an OH— site, may make it difficult for the polymerase to incorporate the bulky, labeled nucleotide into the growing strand and may substantially slow down a primer extension reactions (which can make such nucleotides unviable for use in typical sequencing-by-synthesis schemes where labeled nucleotides are incorporated into all available sites). However, such problems may be avoided, and in some cases may even be beneficial, using the methods provided herein, because only fractional incorporation (e.g., about 5%) may be required and effective incorporation rates may be slowed down by the bulky nucleotides to achieve such fractional incorporation. Furthermore, once a dye is cleaved, an incorporated nucleotide may return to its natural state (e.g., without dye) or may include a scar (e.g., chemical residue) that may be well spaced from other scars of other incorporated nucleotides.

A similar process may pertain to methods involving azidomethyl terminated nucleotides, as shown in FIG. 6. Unblocking azidomethyl terminated nucleotides may comprise the use of cleaving agents (e.g., reducing agents 602). After such agents are introduced, the reversible terminators may undergo conversion to a cyclic intermediate compound (e.g., 604). This process may be reversible. Subsequently, the cyclic intermediate compound may lose nitrogen and undergo hydrolysis to provide the 3' unblocked state (e.g., 607), which may provide an available incorporation site for incorporation of an additional nucleotide. Cleaving agent (e.g., reducing agents) may not be needed for this second part of the unblocking process. Thus, the method may comprise, after the first part of the unblocking process (e.g., conversion to the cyclic intermediate), washing the plurality of nucleic acid molecules to remove cleaving agents (e.g., reducing agents) and dye molecules, and, without waiting for the completion of the unblocking reaction, initiating a next cycle (e.g., repeating the above described operations). Initiating a next cycle may comprise flowing in the first reaction mixture comprising the labeled, reversibly terminated nucleotides under conditions to only fractionally incorporate the labeled nucleotides. Such pre-completion initiation of the next cycle may be possible because the first flow in the sequencing schemes described herein require only fractional incorporation. As the reducing agents have also been washed from the reaction site, the newly incorporated, reversibly terminated nucleotides are not cleaved.

The first flow (e.g., of the first reaction mixture) of a second, third, fourth, etc. sequencing cycle may occur simultaneously with the second part of an unblocking reaction of a previous sequencing cycle. In some cases, the first detection event, second flow, and/or second detection event of a given sequencing cycle may all occur during an unblocking process (e.g., the second part of the unblocking process, as described above) of a previous sequencing cycle.

In some cases, the third flow (e.g., of the third reaction mixture) of a given sequencing cycle, which incorporates nucleotides (e.g., labeled nucleotides, unlabeled nucleotides, or a mixture of labeled and unlabeled nucleotides) into sequences coupled to a remainder of a plurality of nucleic acid molecules into which nucleotides have not yet been incorporated in previous flows (e.g., first and second flows) of the given sequencing cycle to bring the plurality of nucleic acid molecules in phase (e.g., as described herein), may occur after an unblocking process for a previous sequencing cycle has substantially completed. For example, the third flow may be initiated after at least about 95.0%, 95.5%, 96.0%, 96.5%, 97.0%, 97.5%, 98.0%, 98.5%, 99.0%, 99.1%, 99.2%, 99.3%, 99.4%, 99.5%, 99.6%, 99.7%, 99.8%, 99.9% completion of the unblocking process for the previous cycle. For example, the third flow may be initiated after at least about 95.0%, 95.5%, 96.0%, 96.5%, 97.0%, 97.5%, 98.0%, 98.5%, 99.0%, 99.1%, 99.2%, 99.3%, 99.4%, 99.5%, 99.6%, 99.7%, 99.8%, 99.9% of the strands become available for additional incorporation (excluding strands that have already incorporated a nucleotide from the first and/or second flows of the given sequencing cycle).

In some cases, the duration between the time of introduction of cleaving agents (e.g., reducing agents) to initiate the unblocking process in a previous sequencing cycle and the time of introduction of a first reaction mixture to initiate the next sequencing cycle may be less than the duration required for completion of the unblocking process. In some cases, the duration between the time of introduction of cleaving agents (e.g., reducing agents) to initiate the unblocking process in a previous sequencing cycle and the time of introduction of a first reaction mixture to initiate the next sequencing cycle may be less than the duration required for completion of the second part of the unblocking process. In some cases, this duration may be selected to allow nucleotides of a first reaction mixture to be introduced to a plurality of nucleic acid molecules when at least about 50%, 55%, 60%, 65%, 70%, 75%, 80%, 85%, 90%, 95% or more strands (e.g., sequences coupled to the plurality of nucleic acid molecules and having available incorporation sites) are available for incorporation (e.g., after completion of an unblocking process for a preceding cycle). In some cases, this duration may be selected to be constant between each consecutive sequencing cycle, such that the percentage of available strands is substantially constant and reaction conditions for incorporation of nucleotides from a first reaction mixture of a subsequent sequencing cycle are substantially constant.

Beneficially, without having to wait for full completion of unblocking reactions, overall sequencing time may be significantly reduced and efficiency increased. Furthermore, use of 3' disulfide reversible terminators in the methods described herein may facilitate reversion of incorporated nucleotides to their natural states when unblocking reactions are eventually completed, thus reducing the prevalence of chemical residues that could otherwise affect subsequent primer extension reactions.

Various schemes may be employed for analyzing nucleic acid molecules according to the methods provided herein. Several examples are described in the following sections.

Multi-Color Imaging Methods

In some cases, multi-color (e.g., four-color) imaging may be used to analyze nucleic acid molecules. Such methods may be used to identify nucleotides incorporated into growing strands (e.g., into sequences coupled to a plurality of nucleic acid molecules immobilized to a substrate, such as in a detection area). Detection of incorporated nucleotides may include detecting at least 1, 2, 3, 4 or more colors (or frequencies), or combinations of colors. Detection may include detecting one or more colors at different intensities.

In some examples, four-color imaging is employed. Two flows of reaction mixtures comprising various nucleotides may be utilized. A plurality of colonies of nucleic acid molecules (e.g., nucleic acid molecules immobilized to a substrate, such as in a detection area) may be provided, wherein the colonies have sequence homology to different template nucleic acid molecules having different sequences. The template nucleic acid molecules may be DNA molecules.

In the first flow, a first reaction mixture including four different fluorescent dye-labeled, reversibly-terminated nucleotides comprising four different canonical bases may be brought into contact with the plurality of colonies under conditions sufficient to incorporate nucleotides into sequences (e.g., sequencing primers) coupled (e.g., hybridized) to the nucleic acid molecules of the plurality of colonies (e.g., as described herein). For example, the first reaction mixture may comprise a plurality of nucleotides comprising A-bases (labeled with color 1), a plurality of nucleotides comprising C-bases (labeled with color 2), a plurality of nucleotides comprising G-bases (labeled with color 3), and a plurality of nucleotides comprising T-bases (labeled with color 4), where colors 1-4 are distinct and different. In some cases, the concentration of each of the four bases may be low enough to label only a small fraction of the available strands in the colonies. For example, the concentration of each of the four bases may correspond to about 5% of the available strands such that the first reaction mixture comprises enough nucleotides to occupy about 5% of the available incorporation sites of the strands. Accordingly, the relative concentrations within the first reaction mixture may be about 25% A-base nucleotides, about 25% C-base nucleotides, about 25% G-base nucleotides, and about 25% T-base nucleotides. In some cases, the relative concentrations within the first reaction mixture may be adjusted to, for example, account for GC bias. In some cases, the polymerizing enzyme (e.g., polymerizing enzyme used to incorporate the nucleotides into the available incorporation sites), incubation time, and/or particular nucleotides selected for use may be selected to slow effective incorporation rates of one or more nucleotides, such that nucleotides of the first reaction mixture are not incorporated at all available incorporation sites. The plurality of colonies may be imaged (e.g., after a washing process to remove unincorporated nucleotides). Colonies that show a fluorescent color signal of color 1, 2, 3, or 4 will have incorporated an A-base, C-base, G-base, or T-base, respectively, e.g., in about 5% of their strands.

The plurality of colonies may then be exposed (e.g., as described herein) to a second reaction mixture in a second flow comprising non-fluorescent, reversibly terminated nucleotides (e.g., A-, T-, G-, and C-containing nucleotides) in excess to ensure that the non-extended strands will all be extended by one-base; that is, that all the strands are in phase. In some cases, only a subset of strands may be extended during exposure of the plurality of colonies to the second reaction mixture. In some cases, the polymerizing enzyme (e.g., polymerizing enzyme used to incorporate the nucleotides into the available incorporation sites), incubation time, and/or particular nucleotides selected for use may be selected to enhance effective incorporation rates of one or more nucleotides, such that nucleotides are incorporated at more available incorporation sites.

The fluorescent dyes of incorporated nucleotides of the first reaction mixture and/or reversible terminators of incorporated nucleotides of the first and second reaction mixture may be removed (e.g., as described herein), and the process may be repeated by flowing a first reaction mixture comprising the low concentrations of the four bases and imaging, followed by flowing a second reaction mixture comprising an excess of non-fluorescent terminated bases, and removing the dye and reversible terminators. Cleavage of the dye moieties after imaging may be performed after every sequencing cycle or may be performed after multiple sequencing cycles (e.g., after 1, 2, 3, or more sequencing cycles). In some cases, the same cleaving process may be used to remove each different fluorescent dye and the reversible terminators. In other cases, multiple cleaving reagents and/or irradiation cycles may be used to remove each different fluorescent dye and the reversible terminators. Beneficially, only a small proportion (e.g., in this example, approximately 5%) of the clonal population may be 'scarred' by the cleavage of a dye moiety in a given sequencing cycle, minimizing the effect in subsequent sequencing cycles. In some cases, a first reaction mixture may be introduced to initiate a subsequent sequencing cycle prior to completion of the cleavage of the dyes and/or reversible terminators in the previous sequencing cycle, and after washing away cleaving agents (e.g., reducing agents), as described elsewhere herein.

In some cases, the limiting concentration of incorporating nucleotides in the first reaction mixture may be achieved indirectly by reducing the concentration of magnesium or manganese ions to rate-limiting levels. Metal chelators such as ethylenediaminetetraacetic acid (EDTA), ethylene glycol-bis(3-aminoethyl ether)-N,N,N',N'-tetraacetic acid) (egtazic acid, EGTA), citrate, and isocitrate may be used to modulate the level of free magnesium or manganese, which will in turn control the rate of reaction. For example, more nucleotides may be present than are needed to achieve about 5% incorporation, but in the preset amount of time in which the strands are exposed to the nucleotides, only a certain percentage may actually get incorporated.

Alternatively or in addition, inhibitors such as strontium ions may be used to reduce the incorporation of nucleotides, resulting in only a small fraction of available strands being extended. Additional examples of polymerase (e.g., DNA polymerase) inhibitors include, but are not limited to, Aphidicolin, Mithramycin A, and Rifamycin. Certain nucleotide analogs may also function as inhibitors.

In some cases, the first reaction mixture may comprise low levels of unlabeled, reversibly terminated nucleotides as well as fluorescently labeled, reversibly terminated nucleotides. Competition between the labeled and unlabeled nucleotides during incorporation may beneficially address and reduce context dependence problems and the dynamic range of the signals generated from the labeled nucleotides.

Three Flow Monochrome Imaging Methods (1)

A monochrome system with a single emission wavelength and a single collection range has greatly reduced complexity and may enable faster imaging. A single wavelength system may also facilitate use of an optimized imaging system with low cost and complexity, an optimal dye, and low background fluorescence. A monochrome imaging system may be used to analyze incorporation of four different nucleotides comprising four different canonical bases using three sequential flows of different nucleotide mixtures.

A plurality of colonies comprising a plurality of nucleic acid molecules (e.g., on a planar surface, bead or well, such as in a detection area) comprising a plurality of sequences (e.g., sequencing primers) coupled (e.g., hybridized) thereto may be exposed to a first reaction mixture comprising a plurality of fluorescent dye-labeled, reversibly-terminated nucleotides comprising A-bases and a plurality of similarly labeled and reversibly-terminated nucleotides comprising C-bases. In some cases, the concentration of nucleotides in the first reaction mixture may be low enough to label only a small fraction of the available strands in the colony (e.g., about 5%). The plurality of colonies may be imaged (e.g. after a washing process to remove unincorporated nucleotides, as described herein) to generate a first image. Colonies that show a fluorescent signal are likely to have incorporated either an A-base or a C-base in about 5% of their strands.

The plurality of colonies may then be exposed to a second reaction mixture that contains a low concentration of similarly labeled and reversibly terminated nucleotides comprising A-bases and T-bases. In some cases, the polymerizing enzyme, incubation time, and/or particular nucleotides selected for use in the first and second reaction mixtures may be selected to slow effective incorporation rates, such that nucleotides are not incorporated at all available incorporation sites. The colonies may be imaged again (e.g., after a washing process, as described herein) to generate a second image. Colonies that have turned fluorescent in the first image after the first exposure of A- and C-containing nucleotides may have incorporated either an A- or a C-containing nucleotide. Colonies that have an increase in fluorescence intensity in the second image compared to the first image may have incorporated an A-containing nucleotide. Colonies that have not increased in fluorescence intensity from the first image to the second image may have incorporated a C-containing nucleotide. Colonies that were previously dark (no fluorescence) but have become fluorescent after the second flow of A- and T-containing nucleotides have incorporated a T-containing nucleotide. Colonies that remain dark after the both imaging steps may have an open position for a G-containing nucleotide.

The colonies may then be exposed to non-fluorescent, reversibly terminated nucleotides in excess (e.g., A-, T-, G-, and C-containing nucleotides) to ensure that strands that had not extended because of the low concentration (or limited incubation time and/or limited effective incorporation rates, etc.) of the fluorescently-labeled reversibly-terminated nucleotides, or in the case of G-containing nucleotides, lack of exposure, may now all be extended by one-base; that is, all the strands may be in phase. In some cases, the polymerizing enzyme, incubation time, and/or particular nucleotides selected for use may be selected to enhance effective incorporation rates such that nucleotides are incorporated at more available incorporation sites.

The fluorescent dyes may be cleaved off and the terminators may be removed (e.g., in the same or different processes, as described herein), and the process may be repeated by performing a first flow of low concentrations of fluorescently-labeled, reversibly terminated A- and C-containing nucleotides followed by washing and imaging, performing a second flow of low concentration of fluorescently-labeled, reversibly terminated A- and T-containing nucleotides followed by washing and imaging, and performing a third flow with a high concentration of non-fluorescent, reversibly terminated nucleotides (e.g., A-, T-, G-, and C-containing nucleotides). Table 1 below summarizes the three flow monochrome imaging scheme. By measuring the signal in Image 1, and determining the difference between the signal in Image 2 and that in Image 1 (Image 2-Image 1), a digital output is obtained. A signal of 1,1 (Image 1, digital output) reads as an A; a signal of 1,0 reads as a C; a signal of 0,0 reads as a G; and a signal of 0,1 reads as a T.

TABLE 1

Three flow monochrome imaging scheme.

| Image 1 Fluorescence after A-and C-base | Image 2 Fluorescence after A-and T-base | Image 2 − Image 1 | Base call |
|---|---|---|---|
| 1 | 1 + 1 | 1 | A |
| 1 | 1 | 0 | C |
| 0 | 0 | 0 | G |
| 0 | 1 | 1 | T |

The three flow monochrome imaging scheme is schematically illustrated in FIG. 1.

In some cases, cleavage of dye moieties after imaging may be performed after every sequencing cycle or may be performed after multiple sequencing cycles.

In some cases, the first reaction mixture may be introduced to initiate the next sequencing cycle prior to completion of the cleavage of reversible terminators in the previous sequencing cycle, after washing away cleaving agents (e.g., reducing agents), as described elsewhere herein.

In some cases, a limiting concentration of incorporating nucleotides may be achieved indirectly by reducing the concentration of magnesium ions or manganese ions to rate-limiting levels. Metal chelators such as EDTA, EGTA, citrate, and isocitrate may be used to modulate the level of free magnesium or manganese, which may in turn affect the rate of reaction. For example, more nucleotides may be present in a given flow than are needed to achieve about 5% incorporation, but in the preset amount of time in which the strands are exposed to the nucleotides, only a certain percentage may actually get incorporated.

Alternatively or in addition, an inhibitor such as strontium ions may be used to reduce incorporation of nucleotides, resulting in only a small fraction of available strands being extended. Additional examples of polymerase (e.g., DNA polymerase) inhibitors include, but are not limited to, Aphidicolin, Mithramycin A, and Rifamycin. Certain nucleotide analogs may also function as inhibitors.

In some cases, a reaction mixture may comprise low levels of unlabeled reversibly terminated nucleotides as well as fluorescently labeled nucleotides.

As will be appreciated, reaction mixtures may comprise different combinations of canonical base types other than the specific example illustrated herein (e.g., first reaction mixture may comprise T and C, second reaction mixture may comprise T and A, third reaction mixture may comprise A, T, G, C, etc.).

Three Flow Monochrome Imaging Methods (2)

In another scheme employing three flows, a monochrome imaging system may be used to analyze incorporation of nucleotides comprising four canonical bases using three sequential flows of different nucleotide mixtures. A plurality of colonies of nucleic acid molecules (e.g., on a planar surface, bead or well, such as at a detection area, as described herein) having sequences (e.g., sequencing primers) coupled (e.g., hybridized) thereto may be exposed to a first reaction mixture (e.g., as described herein). The first reaction mixture may comprise a plurality of fluorescent dye-labeled, reversibly-terminated nucleotides comprising A-bases, a plurality of similarly labeled and reversibly-terminated nucleotides comprising C-bases, and a plurality of unlabeled, reversibly-terminated nucleotides comprising C-bases. The reaction conditions may be modulated such that only a small fraction of the available strands in a colony that are configured to accept a nucleotide comprising an A-base (e.g., about 5%) actually incorporate a labeled A-containing nucleotide, and the remaining strands may be available to incorporate nucleotides comprising A-bases in subsequent flow(s). The reaction conditions may be modulated such that only a small fraction of the available strands in a colony that are configured to accept a nucleotide comprising a C-base (e.g., about 5%) incorporate a labeled C-containing nucleotide. For example, at least a subset (e.g., a minority, majority, or all) of the remaining available strands may accept an unlabeled C-containing nucleotide from the first reaction mixture. The colonies may be imaged (e.g., after a washing process, as described herein) to generate a first image. Colonies that show a fluorescent signal are likely to have incorporated either an A-containing nucleotide or a C-containing nucleotide in about 5% of their strands. After the first flow, all strands configured to accept a C-containing nucleotide may have accepted a C-containing nucleotide (labeled or unlabeled), such that the C-base incorporation sites are in phase. Alternatively, there may be remaining strands available to incorporate C-containing nucleotides in subsequent flow(s).

The colonies may then be exposed to a second reaction mixture. The second reaction mixture may comprise a plurality of fluorescent dye-labeled, reversibly-terminated nucleotides comprising A-bases; a plurality of similarly labeled and reversibly-terminated nucleotides comprising T-bases; a plurality of unlabeled, reversibly-terminated nucleotides comprising A-bases, and a plurality of unlabeled, reversibly-terminated nucleotides comprising T-bases. The reaction conditions may be modulated such that only a small fraction of the available strands configured to accept a nucleotide comprising an A-base (e.g., about 5% of available strands before or after the first flow) actually incorporate a labeled nucleotide comprising an A-base from the second reaction mixture. For example, at least a subset (e.g., a minority, majority, or all) of the remaining available strands may accept an unlabeled nucleotide comprising an A-base from the second reaction mixture. The reaction conditions may be modulated such that only a small fraction of the available strands configured to accept a nucleotide comprising a T-base (e.g., about 5%) actually incorporate a labeled T-containing nucleotide from the second reaction mixture. For example, at least a subset (e.g., a minority, majority, or all) of the remaining available strands may accept an unlabeled nucleotide comprising a T-base from the second reaction mixture. After the second flow, all strands configured to accept a nucleotide comprising an A-base may have accepted a nucleotide comprising an A-base (labeled or unlabeled) and the A-base incorporation sites may be in phase. Alternatively, there may be remaining strands available to incorporate A-bases in subsequent flow(s). After the second flow, all strands configured to accept a nucleotide comprising a T-base may have accepted a nucleotide comprising a T-base (labeled or unlabeled) and the T-base incorporation sites may be in phase. Alternatively, there may be remaining strands available to incorporate T-bases in subsequent flow(s). The colonies may be imaged again (e.g., after a washing process, as described herein) to generate a second image. Colonies that have an increase in fluorescence intensity in the second image compared to the first image may have incorporated a nucleotide comprising an A-base. Colonies that have not increased in fluorescence intensity from the first image to the second image may have incorporated a nucleotide comprising a C-base. Colonies that were previously dark (no fluorescence) but have become fluorescent after the second flow of nucleotides comprising A- and T-bases have incorporated a nucleotide comprising a T-base. Colonies that remain dark after the both imaging steps may have an open position configured to accept a nucleotide comprising a G-base.

In some cases, the polymerizing enzyme, incubation time, and/or the particular nucleotides selected for use in the first and second reaction mixtures may be selected to slow effective incorporation rates, such that nucleotides are not incorporated at all available incorporation sites. In some cases, the limiting concentration of incorporating nucleotides may be achieved indirectly by reducing the concentration of magnesium ions or manganese ions to rate limiting levels. Metal chelators such as EDTA, EGTA, citrate, and isocitrate may be used to modulate the level of free magnesium or manganese, which may in turn affect the rate of reaction. For example, more nucleotides may be present than are needed to achieve about 5% incorporation, but in the preset amount of time in which the strands are exposed to the nucleotides, only a certain percentage may actually get incorporated. In some cases, an inhibitor such as strontium ions may be used to reduce the incorporation of nucleotides, resulting in only a small fraction of available strands being extended. Additional examples of polymerase (e.g., DNA polymerase) inhibitors include, but are not limited to, Aphidicolin, Mithramycin A, and Rifamycin. Certain nucleotide analogs may also function as inhibitors.

The colonies may then be exposed to a third reaction mixture comprising non-fluorescent, reversibly terminated nucleotides in excess (e.g., A-, T-, G-, and C-containing nucleotides) to ensure that strands that had not extended because of the low concentration (or limited incubation time and/or limited effective incorporation rates, etc.) of the fluorescently-labeled, reversibly-terminated nucleotides, or, in the case of the G-containing nucleotides, lack of exposure, may now all be extended by one-base; that is, all the strands may be in phase. The third reaction mixture may comprise any combination of types of bases that are unlabeled. For example, in some cases, the third reaction mixture may comprise unlabeled nucleotides comprising A-, T-, G-, and C-bases. In some cases, the third reaction mixture may comprise unlabeled nucleotides comprising A-, T-, and G-bases such as where all C-base incorporation sites have been occupied after the first flow. In some cases, the third mixture may comprise unlabeled nucleotides comprising C-, T-, and G-bases such as where all A-base incorporation sites have been occupied after the second flow. In some cases, the third mixture may comprise unlabeled nucleotides comprising A-, C-, and G-bases such as where all T-base incorporation sites have been occupied after the second flow. In some cases, the third mixture may comprise nucleotides comprising G-bases only, such as where all C-base, A-base, and T-base incorporation sites have been occupied after the second flow. In some cases, unlabeled nucleotides comprising G-bases may be included in the first and/or second reaction mixtures. In some cases, the polymerizing enzyme, incubation time, and/or particular nucleotides selected for use may be selected to enhance effective incorporation rates such that nucleotides are incorporated at more available incorporation sites.

The fluorescent dyes may be cleaved off and the terminators may be removed (e.g., in the same or different processes, as described herein), and the process may be repeated to determine digital outputs between the two images for each cycle to determine the sequences of the plurality of nucleic acid molecules.

In some cases, cleavage of dye moieties after imaging may be performed after every sequencing cycle or may be performed after multiple sequencing cycles.

In some cases, the first reaction mixture may be introduced to initiate the next sequencing cycle prior to completion of cleavage of reversible terminators in the previous sequencing cycle, after washing away cleaving agents (e.g., reducing agents), as described elsewhere herein.

In some cases, a reaction mixture may comprise low levels of unlabeled, reversibly terminated nucleotides as well as fluorescently labeled, reversibly terminated nucleotides. As will be appreciated, reaction mixtures may comprise different combinations of canonical base types other than the specific example illustrated herein (e.g., first reaction mixture may comprise T- and C-containing nucleotides, second reaction mixture may comprise T- and A-containing nucleotides, third reaction mixture may comprise A-, T-, G-, and C-containing nucleotides, etc.).

Two Flow Monochrome Imaging Methods (1)

As an alternative to the methods described above, a two flow monochrome imaging scheme may be employed. A monochrome imaging system may be used to analyze the incorporation of nucleotides comprising four different canonical bases with two sequential flows of different nucleotide mixtures. A plurality of colonies of nucleic acid molecules (e.g., on a planar surface, bead or well, such as at a detection area, as described herein) comprising sequences (e.g., sequencing primers) coupled (e.g., hybridized) thereto may be exposed to a first reaction mixture comprising a plurality of fluorescent dye-labeled, reversibly-terminated nucleotides comprising A-bases and a plurality of similarly labeled and reversibly-terminated nucleotides comprising C-bases. The reaction conditions may be controlled such that labeled nucleotides are incorporated into only a small fraction of the available strands in a colony (e.g., about 5%). In some cases, the polymerizing enzyme, incubation time, and/or particular nucleotides selected for use in the first reaction mixture may be selected to slow effective incorporation rates such that the nucleotides are not incorporated at all available incorporation sites. For example, incubation time may be adjusted with respect to the effective incorporation rates such that the nucleotides are not incorporated at all available incorporation sites. The colonies may be imaged (e.g., after a washing process, as described herein) to generate a first image. Colonies that show a fluorescent signal are likely to have incorporated either a nucleotide comprising an A-base or a C-base in about 5% of their strands.

The colonies may then be exposed to a second reaction mixture comprising a plurality of fluorescent dye-labeled, reversibly-terminated nucleotides comprising A-bases; a plurality of similarly labeled and reversibly-terminated nucleotides comprising T-bases; a plurality of non-fluorescent, reversibly-terminated nucleotides comprising C-bases; and a plurality of non-fluorescent, reversibly-terminated nucleotides comprising G-bases. Nucleotides comprising each of the canonical base types may be provided in excess to ensure that strands that had not extended because of the low concentration, slow effective incorporation rates, and/or limited exposure time in the first flow may now all be extended by one-base; that is, all the strands may be in phase. In some cases, the polymerizing enzyme, incubation time, and/or particular nucleotides selected for use may be used to enhance effective incorporation rates such that nucleotides are incorporated at more available incorporation sites. The colonies may be imaged again (e.g., after a washing process, as described herein) to generate a second image. Colonies that have turned fluorescent after the first exposure of A- and C-containing nucleotides may have incorporated either an A-containing nucleotide or a C-containing nucleotide. Colonies that have an increase in fluorescence intensity in the second image compared to the first image may have incorporated an A-containing nucleotide. Colonies that have not increased in fluorescence intensity from the first image to the second image may have incorporated a C-containing nucleotide. Colonies that were previously dark (not fluorescent) but have become fluorescent after the second flow of A- and T-containing nucleotides may have incorporated a T-containing nucleotide. Colonies that remain dark after the both imaging steps may have incorporated a G-containing nucleotide. The fluorescent dyes may be cleaved off and the terminators may be removed, and the process may be repeated by performing the two flows, including the washing and imaging operations after each flow.

By measuring the signal in Image 1, and determining the difference between the signal in Image 2 and that in Image 1 (Image 2-Image 1), a digital output is obtained. Compared to the three flow monochrome imaging scheme described above, the difference between the signal in the first image (after the first flow) and the signal in the second image (after the second flow) may vary. For example, a signal of 1,x reads as an A; a signal of 1,0 reads as a C; a signal of 0,0 reads as a G; and a signal of 0,y reads as a T (where x and y are positive values). Beneficially, incorporation of nucleotides comprising the four different bases may be analyzed with two sequential flows, obviating the need for a third flow.

In other cases, the second reaction mixture may comprise two different labeled nucleotide types comprising two different canonical base types, and four different unlabeled nucleotide types comprising four different canonical base types. All six types of nucleotides may be provided in excess to allow all available incorporation sites to incorporate nucleotides and bring them in phase. Where both unlabeled and labeled nucleotides are present for a canonical base type (e.g., A), the unlabeled nucleotides may be present in greater concentration to minimize 'scarring' effects from the labeled nucleotides. For example, referring to the above example, the second reaction mixture may comprise a plurality of fluorescent dye-labeled reversibly-terminated nucleotides comprising A-base; a plurality of similarly labeled and reversibly-terminated nucleotides comprising T-bases; a plurality of non-fluorescent, reversibly-terminated nucleotides comprising C-bases; a plurality of non-fluorescent, reversibly-terminated nucleotides comprising G bases; a plurality of non-fluorescent, reversibly-terminated nucleotides comprising A-bases; and a plurality of non-fluorescent, reversibly-terminated nucleotides comprising T-bases. In some cases, unlabeled nucleotides comprising A-bases may be provided in greater concentration than labeled nucleotides comprising A-bases in the second reaction mixture, such that more unlabeled nucleotides comprising A-bases are incorporated than labeled nucleotides comprising A-bases to minimize 'scarring' effects. Similarly, unlabeled nucleotides comprising T-bases may be provided in greater concentration than labeled nucleotides comprising T-bases in the second reaction mixture, such that more unlabeled nucleotides comprising T-bases are incorporated than labeled nucleotides comprising T-bases to minimize 'scarring' effects.

In other cases, the first reaction mixture may comprise a plurality of nucleotides comprising a first type of canonical base (e.g., A) that is labeled, a plurality of nucleotides comprising a second type of canonical base (e.g., C) that is labeled, and a plurality of nucleotides comprising the second type of canonical base (e.g., C) that is unlabeled, and the second reaction mixture may comprise a plurality of nucleotides comprising the first type of canonical base (e.g., A) that is labeled, a plurality of nucleotides comprising a third type of canonical base (e.g., T) that is labeled, and a plurality of unlabeled nucleotides comprising bases of the first type (e.g., A), third type (e.g., T), and a fourth type (e.g., G). In the first reaction mixture, the nucleotides comprising the second type of canonical base (e.g., C), whether labeled or unlabeled, may be provided in excess such that all incorporation sites configured to accept nucleotides comprising the second type of canonical base incorporate a nucleotide of the first reaction mixture, whether labeled or unlabeled. In some cases, the unlabeled nucleotides comprising bases of the second canonical base type may be present in a greater concentration than the labeled nucleotides comprising bases of the second canonical base type in the first reaction mixture to minimize 'scarring' effects from the labeled nucleotides. In some instances, where the nucleotides comprising the second type of canonical base (e.g., C) are not provided in excess (or introduced under conditions for incorporation into all available incorporation sites) in the first reaction mixture, the second reaction mixture may further comprise unlabeled nucleotides comprising the second type of canonical base. In some instances, of nucleotides comprising the four different canonical bases, the base type selected as the second type of canonical base in this example may be the base type having slowest incorporation.

In some cases, cleavage of dye moieties after imaging may be performed after every sequencing cycle or may be performed after multiple sequencing cycles.

In some cases, the first reaction mixture may be introduced to initiate a next sequencing cycle prior to completion of cleavage of reversible terminators in the previous sequencing cycle, after washing away cleaving agents (e.g., reducing agents), as described elsewhere herein.

In some cases, a limiting concentration of incorporating nucleotides may be achieved indirectly by reducing the concentration of magnesium ions or manganese ions to rate limiting levels. Metal chelators such as EDTA, EGTA, citrate, and isocitrate may be used to modulate the level of free magnesium or manganese, which may in turn affect the rate of reaction. For example, more nucleotides may be present than are needed to achieve about 5% incorporation, but in the preset amount of time in which the strands are exposed to the nucleotides, only a certain percentage may actually get incorporated.

Alternatively or in addition, an inhibitor such as strontium ions may be used to reduce incorporation of nucleotides, resulting in only a small fraction of available strands being extended. Additional examples of polymerase (e.g., DNA polymerase) inhibitors include, but are not limited to, Aphidicolin, Mithramycin A, and Rifamycin. Certain nucleotide analogs may also function as inhibitors.

In some cases, a reaction mixture may comprise low levels of unlabeled reversibly terminated nucleotides as well as fluorescently labeled nucleotides.

Two Flow Monochrome Imaging Methods (2)

The following example provides an alternative to the two flow monochrome imaging scheme described above. A plurality of colonies of nucleic acid molecules (e.g., on a planar surface, bead or well, such as in a detection area, as described herein) with sequences (e.g., sequencing primers) coupled (e.g., hybridized) thereto may be exposed to a mixture of a low concentration of a fluorescent dye-labeled, reversibly-terminated nucleotides in a manner that creates a different brightness for the different bases.

In some cases, the first reaction mixture may comprise multiple different labeled nucleotides in different concentrations (e.g., 0% A-containing nucleotides, 5% C-containing nucleotides, 10% G-containing nucleotides, and 20% T-containing nucleotides). The average concentration may be low enough to label only a small fraction of the available strands in the colony (e.g., 35%/4=8.75% in this example). The maximal concentration may also be limited (20% in this case) to prevent neighboring dye accumulation in homopolymers. In some cases, the polymerizing enzyme, incubation time, and/or particular nucleotides selected for use may be selected to slow effective incorporation rates such that nucleotides are not incorporated at all available incorporation sites. The colonies may be imaged (e.g., after a washing process, as described herein). The relative brightness of the fluorescent signal may indicate which of the nucleotides are incorporated into strands of a given colony.

In some cases, the first reaction mixture may comprise multiple different labeled nucleotides in approximately the same concentrations. Each nucleotide of the reaction mixture may have a different fluorescence intensity either due to the use of dyes with similar excitation wavelengths and similar emission wavelengths but substantially different fluorescence yields or dyes that have shifted excitation and emission peaks and hence will have a different brightness at the specific excitation and emission wavelengths of an imaging system.

In some cases, different brightness for different nucleotides comprising different bases in a reaction mixture may be obtained by mixing fluorescently-labeled nucleotides with non-fluorescently labeled nucleotides. For example, the first reaction mixture may comprise multiple different nucleotides comprising different canonical bases, where each different nucleotide type includes fluorescently- and non-fluorescently labeled nucleotides. As in preceding examples, the first reaction mixture may comprise nucleotides at concentrations or relative amounts corresponding to a small fraction of the plurality of nucleic acid molecules, such as 5% of the plurality of nucleic acid molecules. For example, 100% of the A-containing nucleotides (e.g., 100% of the 5% incorporated) may be labeled with a fluorescent dye, 50% of the C-containing nucleotides may be labeled with the same fluorescent dye, 25% of the T-containing nucleotides may be labeled with the same fluorescent dye, and 0% of the G-containing nucleotides may be labeled.

In the above examples, the colonies may then be exposed to a second reaction mixture comprising non-fluorescent, reversibly terminated nucleotides in excess to ensure that strands that had not extended because of the low-concentration of the fluorescent-labeled, reversibly-terminated nucleotides in the first flow may now all be extended by one-base; that is, all the strands may be in phase. The fluorescent dyes may be cleaved off and the terminator may be removed (e.g., in the same or different processes, as described herein), and the process may be repeated.

In some cases, the first reaction mixture may be introduced to initiate the next sequencing cycle prior to completion of cleavage of reversible terminators of incorporated nucleotides in the previous sequencing cycle, after washing away cleaving agents (e.g., reducing agents), as described elsewhere herein.

Four Flow Methods

The methods provided herein may comprise the use of a four flow monochrome imaging scheme. A monochrome imaging system may be used to analyze incorporation of nucleotides comprising four different bases with four sequential flows of different nucleotide mixtures. A plurality of colonies of nucleic acid molecules (e.g., on a planar surface, bead or well, such as at a detection area, as described herein) comprising sequences (e.g., sequencing primers) coupled (e.g., hybridized) thereto may be exposed to a first reaction mixture. The first reaction mixture may comprise a plurality of fluorescent dye-labeled reversibly-terminated nucleotides comprising A-bases and a plurality of unlabeled, reversibly terminated nucleotides comprising A-bases. The reaction conditions may be modulated such that only a small fraction of the available strands in a colony that are configured to accept an A-base containing nucleotide (e.g., about 5%) actually incorporate a labeled nucleotide. For example, at least a subset (e.g., a minority, majority, or all) of the remaining available strands may accept an unlabeled nucleotide of the first reaction mixture. The colonies may be imaged (e.g., after a washing process) to generate a first image. Colonies that show a fluorescent signal may have incorporated an A-base containing nucleotide in about 5% of their strands. After the first flow, all strands accepting an A-base containing nucleotide may have accepted an A-base containing nucleotide (labeled or unlabeled), such that the A-base incorporation sites are in phase. Alternatively, there may be remaining strands available to incorporate A-containing nucleotides in subsequent flow(s).

The colonies may then be exposed to a second reaction mixture. The second reaction mixture may comprise a plurality of fluorescent dye-labeled reversibly-terminated nucleotides comprising C-bases and a plurality of unlabeled, reversibly terminated nucleotides comprising C-bases. The reaction conditions may be modulated such that only a small fraction of the available strands in a colony that are configured to accept a C-containing nucleotide (e.g., about 5%) actually incorporate a labeled nucleotide. For example, at least a subset (e.g., a minority, majority, or all) of the remaining available strands may accept an unlabeled nucleotide of the second reaction mixture. The colonies may be imaged (e.g., after a washing process) to generate a second image. Colonies that were previously dark in the first image but become fluorescent in the second image may have incorporated a C-containing nucleotide in about 5% of their strands. After the second flow, all strands configured to accept a C-containing nucleotide may have accepted a C-base (labeled or unlabeled), such that the C-base incorporation sites are in phase. Alternatively, there may be remaining strands available to incorporate C-containing nucleotides in subsequent flow(s).

The colonies may then be exposed to a third reaction mixture. The third reaction mixture may comprise a plurality of fluorescent dye-labeled reversibly-terminated nucleotides comprising T-bases (or U-bases) and a plurality of unlabeled, reversibly terminated nucleotides comprising T-bases. The reaction conditions may be modulated such that only a small fraction of the available strands in a colony that are configured to accept a T-containing nucleotide (e.g., about 5%) actually incorporate a labeled nucleotide. For example, at least a subset (e.g., a minority, majority, or all) of the remaining available strands may accept an unlabeled nucleotide of the third reaction mixture. The colonies may be imaged (e.g., after a washing process) to generate a third image. Colonies that were previously dark in the first and second images but become fluorescent in the third image may have incorporated a T-containing nucleotide in about 5% of their strands. Colonies that remain dark in all three images may be indicative of an available G-base incorporation site. After the third flow, all strands configured to accept a T-containing nucleotide may have accepted a T-containing nucleotide (labeled or unlabeled), such that the T-base incorporation sites are in phase. Alternatively, there may be remaining strands available to incorporate T-containing nucleotides in subsequent flow(s).

In some cases, the polymerizing enzyme, incubation time, and/or particular nucleotides selected for use in the first, second, and third reaction mixtures may be selected to slow effective incorporation rates, such that nucleotides are not incorporated at all available incorporation sites in a given flow. In some cases, limiting concentrations of incorporating nucleotides may be achieved indirectly by reducing the concentration of magnesium ions or manganese ions to rate limiting levels. Metal chelators such as EDTA, EGTA, citrate, and isocitrate may be used to modulate the level of free magnesium or manganese, which may in turn affect the rate of reaction. For example, more nucleotides may be present than are needed to achieve about 5% incorporation, but in the preset amount of time in which the strands are exposed to the nucleotides, only a certain percentage may actually get incorporated. In some cases, an inhibitor such as strontium ions may be used to reduce incorporation of nucleotides, resulting in only a small fraction of available strands being extended. Additional examples of polymerase (e.g., DNA polymerase) inhibitors include, but are not limited to, Aphidicolin, Mithramycin A, and Rifamycin. Certain nucleotide analogs may also function as inhibitors.

The colonies may then be exposed to a fourth reaction mixture comprising non-fluorescent, reversibly terminated nucleotides in excess (e.g., A-, T-, G-, and C-containing nucleotides) to ensure that strands that had not extended because of the low concentration (or limited incubation time and/or limited effective incorporation rates, etc.) of the nucleotides, or in the case of the G-containing nucleotides, lack of exposure in the previous flows, may now all be extended by one-base; that is, all the strands may be in phase. The fourth reaction mixture may comprise any combination of types of bases that are unlabeled. For example, in some cases, the fourth reaction mixture may comprise unlabeled nucleotides comprising A-, T-, G-, and C-bases. In some cases, the fourth reaction mixture may comprise unlabeled nucleotides comprising C-, T-, and G-bases such as where all A-base incorporation sites have been occupied after the first flow. In some cases, the fourth mixture may comprise unlabeled nucleotides comprising A-, T-, and G-bases such as where all C-base incorporation sites have been occupied after the second flow. In some cases, the fourth mixture may comprise unlabeled nucleotides comprising G bases only, such as where all C-base, A-base, and T-base incorporation sites have been occupied after the third flow. In some cases, unlabeled nucleotides comprising G-bases may be included in the first, second, and/or third reaction mixtures. In some cases, the polymerizing enzyme, incubation time, and/or particular nucleotides selected for use may be selected to enhance effective incorporation rates such that nucleotides are incorporated at more available incorporation sites.

The fluorescent dyes may be cleaved off and the terminators may be removed (e.g., in the same or different processes, as described herein), and the process may be repeated to determine digital outputs between the three images for each cycle to determine the sequences of the plurality of nucleic acid molecules.

In some cases, cleavage of dye moieties after imaging may be performed after every sequencing cycle or may be performed after multiple sequencing cycles.

In some cases, the first reaction mixture may be introduced to initiate a next sequencing cycle prior to completion of cleavage of reversible terminators in a previous sequencing cycle, after washing away cleaving agents (e.g., reducing agents), as described elsewhere herein.

As will be appreciated, reaction mixtures may comprise different combinations of canonical base types other than the specific example illustrated herein (e.g., first reaction mixture may comprise labeled and unlabeled nucleotides comprising T-bases, second reaction mixture may comprise labeled and unlabeled nucleotides comprising C-bases, third reaction mixture may comprise labeled and unlabeled nucleotides comprising A-bases, and fourth reaction mixture may comprise unlabeled nucleotides comprising A-, T-, G-, and C-bases, etc.).

Single Flow Methods

In some cases, a single flow (e.g., reaction mixture) may comprise multiple non-labeled, reversibly terminated nucleotide types comprising different bases (e.g., canonical base types) as well as varying ratios of labeled nucleotides comprising different bases. As in a preceding example, measured relative brightness may be used to determine which nucleotide type was incorporated. This system may have a 'context dependence' issue (e.g., as described herein). For example, in different locations the ratio of incorporation of labeled nucleotides to incorporation of unlabeled nucleotides may vary and hence the brightness may vary. Uncorrected, this may cause confusion between two bases. For example, high incorporation of a labeled nucleotide included in the reaction mixture at a low concentration may appear similar to lower incorporation of a labeled nucleotide included in the reaction mixture at a higher concentration. However, if all of the nucleotides in the reaction mixture are reversibly terminated, no homopolymers will be incorporated, and any corrections or calibrations needed to facilitate nucleic acid sequence identification will be straightforward.

In another example, a single flow (e.g., reaction mixture) containing multiple bases labeled with different colors may be used. For example, each different nucleotide type may be labeled with a different fluorescent dye (e.g., as described herein). The reaction mixture may also include unlabeled bases, such that only a single flow may be used rather than the two flow scheme described in the "Multi-color imaging methods" section included above.

Nucleic Acid Molecules

Nucleic acid molecules analyzed using the methods of the present disclosure may be of any type or origin. A nucleic acid molecule may be a target nucleic acid molecule. As used herein, the terms "template nucleic acid", "target nucleic acid", "nucleic acid molecule," "nucleic acid sequence," "nucleic acid fragment," "oligonucleotide," "polynucleotide," and "nucleic acid" generally refer to polymeric forms of nucleotides of any length, such as deoxyribonucleotides (dNTPs) or ribonucleotides (rNTPs), or analogs thereof, and may be used interchangeably. Nucleic acids may have any three dimensional structure, and may perform any function, known or unknown. An oligonucleotide is typically composed of a specific sequence of four nucleotide bases: adenine (A); cytosine (C); guanine (G); and thymine (T) (uracil (U) for thymine (T) when the polynucleotide is RNA). Oligonucleotides may include one or more nonstandard nucleotide(s), nucleotide analog(s) and/or modified nucleotides. Non-limiting examples of nucleic acids include deoxyribonucleic acid (DNA), ribonucleic acid (RNA), genomic DNA (e.g., gDNA such as sheared gDNA), cell-free DNA (e.g., cfDNA), synthetic DNA or RNA, coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, complementary DNA (cDNA), plasmid DNA, recombinant nucleic acid molecules, branched nucleic acid molecules, plasmids, vectors, isolated DNA of any sequence, isolated RNA of any sequence, nucleic acid probes, artificial nucleic acid analogs (e.g., peptide nucleic acids, morpholino oligomers, locked nucleic acids, glycol nucleic acids, and threose nucleic acids), chromatin, and primers. A nucleic acid may comprise one or more modified nucleotides, such as methylated nucleotides and nucleotide analogs. If present, modifications to the nucleotide structure may be made before or following assembly of the nucleic acid. The sequence of nucleotides of a nucleic acid may be interrupted by non-nucleotide components. A nucleic acid may be further modified following polymerization, such as by conjugation or binding with a reporter agent. In some cases, a nucleic acid molecule may be a DNA molecule. In other cases, a nucleic acid molecule may be an RNA molecule.

A nucleic acid molecule may be double-stranded or single-stranded. In some cases, a nucleic acid molecule immobilized to a detection area may be a double-stranded molecule, and the nucleic acid molecule may be denatured to remove one strand in preparation for analysis by sequencing. In some cases, a complement of a target nucleic acid strand may be analyzed. In other cases, the target nucleic acid strand, or a duplicate thereof (e.g., an amplicon) may be analyzed. Denaturation may be performed by, for example, altering a temperature or pH condition or by exposing a nucleic acid molecule to a chemical denaturant such as a detergent.

Nucleic acid molecules may have any useful characteristics. For example, a nucleic acid molecule may have any useful size (e.g., length). For example, a single-stranded nucleic acid molecule may comprise at least 10 bases (e.g., nucleobases), 20 bases, 30 bases, 40 bases, 50 bases, 60 bases, 70 bases, 80 bases, 90 bases, 100 bases, 200 bases, 300 bases, 400 bases, 500 bases, 600 bases, 700 bases, 800 bases, 900 bases, 1 kilobase (kb), 2 kb, 3 kb, 4 kb, 5 kb, 6 kb, 7 kb, 8 kb, 9 kb, 10 kb, or more bases. Similarly, a double-stranded nucleic acid molecule may comprise at least 10 base pairs (bp), 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1,000 bp, 2,000 bp, 3,000 bp, 4,000 bp, 5,000 bp, 6,000 bp, 7,000 bp, 8,000 bp, 9,000 bp, 10,000 bp, or more base pairs.

A nucleic acid molecule may include naturally occurring and/or non-naturally occurring nucleotides (e.g., modified nucleotides or nucleotide analogs, as described herein).

A nucleic acid molecule may include a label such as a detectable moiety (e.g., as described herein). For example, a nucleic acid molecule may include a fluorescent tag (e.g., in or attached to a nucleotide). Nucleic acid molecules may also include one or more features such as introns, exons, coding regions, untranslated regions, priming sequences, unique molecular identifiers, molecular lineage tags, and barcode sequences. In some cases, a nucleic acid molecule may include an adapter (e.g., ligated thereto, or incorporated into a sequence following an amplification process). An adapter may include a priming sequence and one or more additional sequences such as a barcode sequence or unique molecular identifier, a functional sequence facilitating attachment of a nucleic acid molecule to a support, or another sequence. An adapter may have any useful length, base content, or other characteristic. In some cases, a nucleic acid molecule may include a first adapter at a first end of the molecule and a second adapter at a second end of the molecule. An adapter may be single-stranded or double-stranded.

A nucleic acid molecule may be immobilized to a support (e.g., as described herein). For example, a nucleic acid molecule may be immobilized to a planar array. A support may include a plurality of nucleic acid molecules attached thereto. For example, a support may include one or more colonies each including a plurality of nucleic acid molecules. Colonies of nucleic acid molecules may be produced using clonal amplification methods (e.g., as described herein). For example, colonies of nucleic acid molecules may be produced using bridge amplification, recombinase polymerase amplification, wildfire amplification, or other methods. Different colonies included on a support may include different populations of nucleic acids. For example, a first colony may include nucleic acid molecules having a first set of characteristics and a second colony may include nucleic acid molecules having a second set of characteristics. The nucleic acid molecules of the first and second colonies may derive from the same source and in some cases may be or derive from fragments of the same nucleic acid molecule (e.g., nucleic acid molecules of the first colony may derive from a first fragment of a larger nucleic acid molecule and nucleic acid molecules of the second colony may derive from a second fragment of the same larger nucleic acid molecule). Nucleic acid molecules deriving from the same source may include overlapping sequences. Colonies of nucleic acid molecules may be included in a detection area of a support (e.g., as described herein). A detection area may include one or more colonies of nucleic acid molecules. For example, a detection area may include at least 1, 2, 3, 4, 5, 6, 7, 8, 9, 10, 11, 12, 13, 14, 15, 16, 17, 18, 19, 20, or more colonies. Colonies may include the same or different numbers of nucleic acid molecules. For example, a first colony may include more nucleic acid molecules than a second colony. Colonies may be arranged on a support (e.g., a detection area of a support) in a pattern or may be irregularly arranged. In some cases, the distribution of nucleic acid molecules (e.g., colonies of nucleic acid molecules) on a support may be driven by a distribution of adapters attached to the support that may be used in clonal amplification methods.

A nucleic acid molecule may derive from cells or may be a cell-free nucleic acid molecule (e.g., as described herein). Nucleic acid molecules may be extracellular or may be contained within one or more cells. Nucleic acid molecules included within cells may be accessed by lysing or permeabilizing the cells. For example, a mechanical method (e.g., mechanical agitation such as vortexing, stirring, bead beating, shaking, centrifuging, or a combination thereof) and/or a chemical agent (e.g., addition of one or more reagents such as lysis buffers or solvents) may be used to lyse or permeabilize a cell to provide access to one or more nucleic acid molecules contained therein.

A nucleic acid molecule analyzed by the methods described herein may derive from an environmental or a biological source. A biological source may be, for example, from a subject. The term "subject," as used herein, generally refers to an individual or entity from which a biological sample (e.g., a biological sample that is undergoing or will undergo processing or analysis as described herein) may be derived. A subject may be a human, a plant, or an animal (e.g., mammal or non-mammal) such as a primate, rodent, cat, dog, rabbit, horse, pig, bird, simian, farm animal, companion animal, sport animal, or other animal. A subject may be a patient. The subject may have or be suspected of having a disease or disorder, such as cancer (e.g., breast cancer, colorectal cancer, brain cancer, leukemia, lung cancer, skin cancer, liver cancer, pancreatic cancer, lymphoma, esophageal cancer, or cervical cancer) or an infectious disease. Alternatively or in addition, a subject may be known to have previously had a disease or disorder. The subject may have or be suspected of having a genetic disorder such as achondroplasia, alpha-1 antitrypsin deficiency, antiphospholipid syndrome, autism, autosomal dominant polycystic kidney disease, Charcot-Marie-tooth, cri du chat, Crohn's disease, cystic fibrosis, Dercum disease, down syndrome, Duane syndrome, Duchenne muscular dystrophy, factor V Leiden thrombophilia, familial hypercholesterolemia, familial Mediterranean fever, fragile x syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency, sickle cell disease, spinal muscular atrophy, Tay-Sachs, thalassemia, trimethylaminuria, Turner syndrome, velocardiofacial syndrome, WAGR syndrome, or Wilson disease. A subject may be undergoing treatment for a disease or disorder. A subject may be symptomatic or asymptomatic of a given disease or disorder. A subject may be healthy (e.g., not suspected of having disease or disorder). A subject may have one or more risk factors for a given disease. A subject may have a given weight, height, body mass index, or other physical characteristic. A subject may have a given ethnic or racial heritage, place of birth or residence, nationality, disease or remission state, family medical history, or other characteristic.

As used herein, the term "biological sample" generally refers to a sample obtained from a subject. The biological sample may be obtained directly or indirectly from the subject. A sample may be obtained from a subject via any suitable method, including, but not limited to, spitting, swabbing, blood draw, biopsy, obtaining excretions (e.g., urine, stool, sputum, vomit, or saliva), excision, scraping, and puncture. A sample may be obtained from a subject by, for example, intravenously or intraarterially accessing the circulatory system, collecting a secreted biological sample (e.g., stool, urine, saliva, sputum, etc.), breathing, or surgically extracting a tissue (e.g., biopsy). The sample may be obtained by non-invasive methods including but not limited to: scraping of the skin or cervix, swabbing of the cheek, or collection of saliva, urine, feces, menses, tears, or semen. Alternatively, the sample may be obtained by an invasive procedure such as biopsy, needle aspiration, or phlebotomy. A sample may comprise a bodily fluid such as, but not limited to, blood (e.g., whole blood, red blood cells, leukocytes or white blood cells, platelets), plasma, serum, sweat, tears, saliva, sputum, urine, semen, mucus, synovial fluid, breast milk, colostrum, amniotic fluid, bile, bone marrow, interstitial or extracellular fluid, or cerebrospinal fluid. For example, a sample may be obtained by a puncture method to obtain a bodily fluid comprising blood and/or plasma. Such a sample may comprise both cells and cell-free nucleic acid material. Alternatively, the sample may be obtained from any other source including but not limited to blood, sweat, hair follicle, buccal tissue, tears, menses, feces, or saliva. The biological sample may be a tissue sample, such as a tumor biopsy. The sample may be obtained from any of the tissues provided herein including, but not limited to, skin, heart, lung, kidney, breast, pancreas, liver, intestine, brain, prostate, esophagus, muscle, smooth muscle, bladder, gall bladder, colon, or thyroid. The methods of obtaining provided herein include methods of biopsy including fine needle aspiration, core needle biopsy, vacuum assisted biopsy, large core biopsy, incisional biopsy, excisional biopsy, punch biopsy, shave biopsy or skin biopsy. The biological sample may comprise one or more cells. A biological sample may comprise one or more nucleic acid molecules such as one or more deoxyribonucleic acid (DNA) and/or ribonucleic acid (RNA) molecules (e.g., included within cells or not included within cells). Nucleic acid molecules may be included within cells. Alternatively or in addition, nucleic acid molecules may not be included within cells (e.g., cell-free nucleic acid molecules). The biological sample may be a cell-free sample.

The term "cell-free sample," as used herein, generally refers to a sample that is substantially free of cells (e.g., less than 10% cells on a volume basis). A cell-free sample may be derived from any source (e.g., as described herein). For example, a cell-free sample may be derived from blood, sweat, urine, or saliva. For example, a cell-free sample may be derived from a tissue or bodily fluid. A cell-free sample may be derived from a plurality of tissues or bodily fluids. For example, a sample from a first tissue or fluid may be combined with a sample from a second tissue or fluid (e.g., while the samples are obtained or after the samples are obtained). In an example, a first fluid and a second fluid may be collected from a subject (e.g., at the same or different times) and the first and second fluids may be combined to provide a sample. A cell-free sample may comprise one or more nucleic acid molecules such as one or more DNA or RNA molecules.

A sample that is not a cell-free sample (e.g., a sample comprising one or more cells) may be processed to provide a cell-free sample. For example, a sample that includes one or more cells as well as one or more nucleic acid molecules (e.g., DNA and/or RNA molecules) not included within cells (e.g., cell-free nucleic acid molecules) may be obtained from a subject. The sample may be subjected to processing (e.g., as described herein) to separate cells and other materials from the nucleic acid molecules not included within cells, thereby providing a cell-free sample (e.g., comprising nucleic acid molecules not included within cells). The cell-free sample may then be subjected to further analysis and processing (e.g., as provided herein). Nucleic acid molecules not included within cells (e.g., cell-free nucleic acid molecules) may be derived from cells and tissues. For example, cell-free nucleic acid molecules may derive from a tumor tissue or a degraded cell (e.g., of a tissue of a body). Cell-free nucleic acid molecules may comprise any type of nucleic acid molecules (e.g., as described herein). Cell-free nucleic acid molecules may be double-stranded, single-stranded, or a combination thereof. Cell-free nucleic acid molecules may be released into a bodily fluid through secretion or cell death processes, e.g., cellular necrosis, apoptosis, or the like. Cell-free nucleic acid molecules may be released into bodily fluids from cancer cells (e.g., circulating tumor DNA (ctDNA)). Cell free nucleic acid molecules may also be fetal DNA circulating freely in a maternal blood stream (e.g., cell-free fetal nucleic acid molecules such as cffDNA). Alternatively or in addition, cell-free nucleic acid molecules may be released into bodily fluids from healthy cells.

A biological sample may comprise a plurality of target nucleic acid molecules. For example, a biological sample may comprise a plurality of target nucleic acid molecules from a single subject. In another example, a biological sample may comprise a first target nucleic acid molecule from a first subject and a second target nucleic acid molecule from a second subject.

A biological sample may be obtained directly from a subject and analyzed without any intervening processing, such as, for example, sample purification or extraction. For example, a blood sample may be obtained directly from a subject by accessing the subject's circulatory system, removing the blood from the subject (e.g., via a needle), and transferring the removed blood into a receptacle. The receptacle may comprise reagents (e.g., anti-coagulants) such that the blood sample is useful for further analysis. Such reagents may be used to process the sample or analytes derived from the sample in the receptacle or another receptacle prior to analysis. In another example, a swab may be used to access epithelial cells on an oropharyngeal surface of the subject. Following obtaining the biological sample from the subject, the swab containing the biological sample may be contacted with a fluid (e.g., a buffer) to collect the biological fluid from the swab.

Any suitable biological sample that comprises one or more nucleic acid molecules may be obtained from a subject. A sample (e.g., a biological sample or cell-free biological sample) suitable for use according to the methods provided herein may be any material comprising tissues, cells, degraded cells, nucleic acids, genes, gene fragments, expression products, gene expression products, and/or gene expression product fragments of an individual to be tested. A biological sample may be solid matter (e.g., biological tissue) or may be a fluid (e.g., a biological fluid). In general, a biological fluid may include any fluid associated with living organisms. Non-limiting examples of a biological sample include blood (or components of blood—e.g., white blood cells, red blood cells, platelets) obtained from any anatomical location (e.g., tissue, circulatory system, bone marrow) of a subject, cells obtained from any anatomical location of a subject, skin, heart, lung, kidney, breath, bone marrow, stool, semen, vaginal fluid, interstitial fluids derived from tumorous tissue, breast, pancreas, cerebral spinal fluid, tissue, throat swab, biopsy, placental fluid, amniotic fluid, liver, muscle, smooth muscle, bladder, gall bladder, colon, intestine, brain, cavity fluids, sputum, pus, microbiota, meconium, breast milk, prostate, esophagus, thyroid, serum, saliva, urine, gastric and digestive fluid, tears, ocular fluids, sweat, mucus, earwax, oil, glandular secretions, spinal fluid, hair, fingernails, skin cells, plasma, nasal swab or nasopharyngeal wash, spinal fluid, cord blood, emphatic fluids, and/or other excretions or body tissues. Methods for determining sample suitability and/or adequacy are provided. A sample may include, but is not limited to, blood, plasma, tissue, cells, degraded cells, cell-free nucleic acid molecules, and/or biological material from cells or derived from cells of an individual such as cell-free nucleic acid molecules. The sample may be a heterogeneous or homogeneous population of cells, tissues, or cell-free biological material. The biological sample may be obtained using any method that can provide a sample suitable for the analytical methods described herein.

A sample may undergo one or more pre-processing operations in preparation for processing or analysis. For example, a sample may be processed to lyse or permeabilize cells, remove solid or other materials, denature proteins and/or nucleic acid molecules, dilute the sample, buffer the sample to a particular pH, or any combination thereof A sample (e.g., a biological sample or cell-free biological sample) may undergo one or more processes in preparation for analysis. For example, a sample may be processed to lyse or permeabilize cells, remove solid or other materials, denature proteins and/or nucleic acid molecules, dilute the sample, buffer the sample to a particular pH, or any combination thereof. Phase separation to separate one or more liquid and solid phases may also be performed. For example, a precipitation, extraction, clarification, crystallization, sedimentation, centrifugation, fluid flow, mechanical agitation (e.g., bead beating), or filtration process may be performed. Pre-processing of a sample may comprise heating a sample and/or combining a sample with one or more reagents such as buffers and washes. In some cases, a sample may undergo one or more processes such as filtration, centrifugation, selective precipitation, permeabilization, isolation, agitation, heating, purification, and/or other processes. For example, a sample may be filtered to remove contaminants or other materials. In an example, a sample comprising cells may be processed to separate the cells from other material in the sample. Such a process may be used to prepare a sample comprising only cell-free nucleic acid molecules. Such a process may consist of a multi-step centrifugation process. Multiple samples, such as multiple samples from the same subject (e.g., obtained in the same or different manners from the same or different bodily locations, and/or obtained at the same or different times (e.g., seconds, minutes, hours, days, weeks, months, or years apart)) or multiple samples from different subjects may be obtained for analysis as described herein. In an example, the first sample is obtained from a subject before the subject undergoes a treatment regimen or procedure and the second sample is obtained from the subject after the subject undergoes the treatment regimen or procedure. Alternatively or in addition, multiple samples may be obtained from the same subject at the same or approximately the same time. Different samples obtained from the same subject may be obtained in the same or different manner. For example, a first sample may be obtained via a biopsy and a second sample may be obtained via a blood draw. Samples obtained in different manners may be obtained by different medical professionals, using different techniques, at different times, and/or at different locations. Different samples obtained from the same subject may be obtained from different areas of a body. For example, a first sample may be obtained from a first area of a body (e.g., a first tissue) and a second sample may be obtained from a second area of the body (e.g., a second tissue).

A biological sample as used herein (e.g., a biological sample comprising one or more nucleic acid molecules) may not be purified when provided in a reaction vessel. Furthermore, for a biological sample comprising one or more nucleic acid molecules, the one or more nucleic acid molecules may not be extracted when the biological sample is provided to a reaction vessel. For example, ribonucleic acid (RNA) and/or deoxyribonucleic acid (DNA) molecules of a biological sample may not be extracted from the biological sample when providing the biological sample to a reaction vessel. Moreover, a target nucleic acid (e.g., a target RNA or target DNA molecules) present in a biological sample may not be concentrated when providing the biological sample to a reaction vessel. Alternatively, a biological sample may be purified and/or nucleic acid molecules may be isolated from other materials in the biological sample.

Alternatively, a sample may be an environmental sample. An environmental sample may be collected from a surface or reservoir. For example, an environmental sample may be collected from a surface that is handled by or interacts with a human or animal. An environmental sample may comprise solid or fluid material. For example, an environmental sample may comprise water derived from a body of water or a plumbed system.

Nucleic acid molecules contained within a sample may derive from one or more different sources. For example, an environmental sample may comprise nucleic acid molecules associated with multiple organisms, such as multiple humans who have interacted with the same surface from which a sample may derive.

Computer Systems

Figure 4:
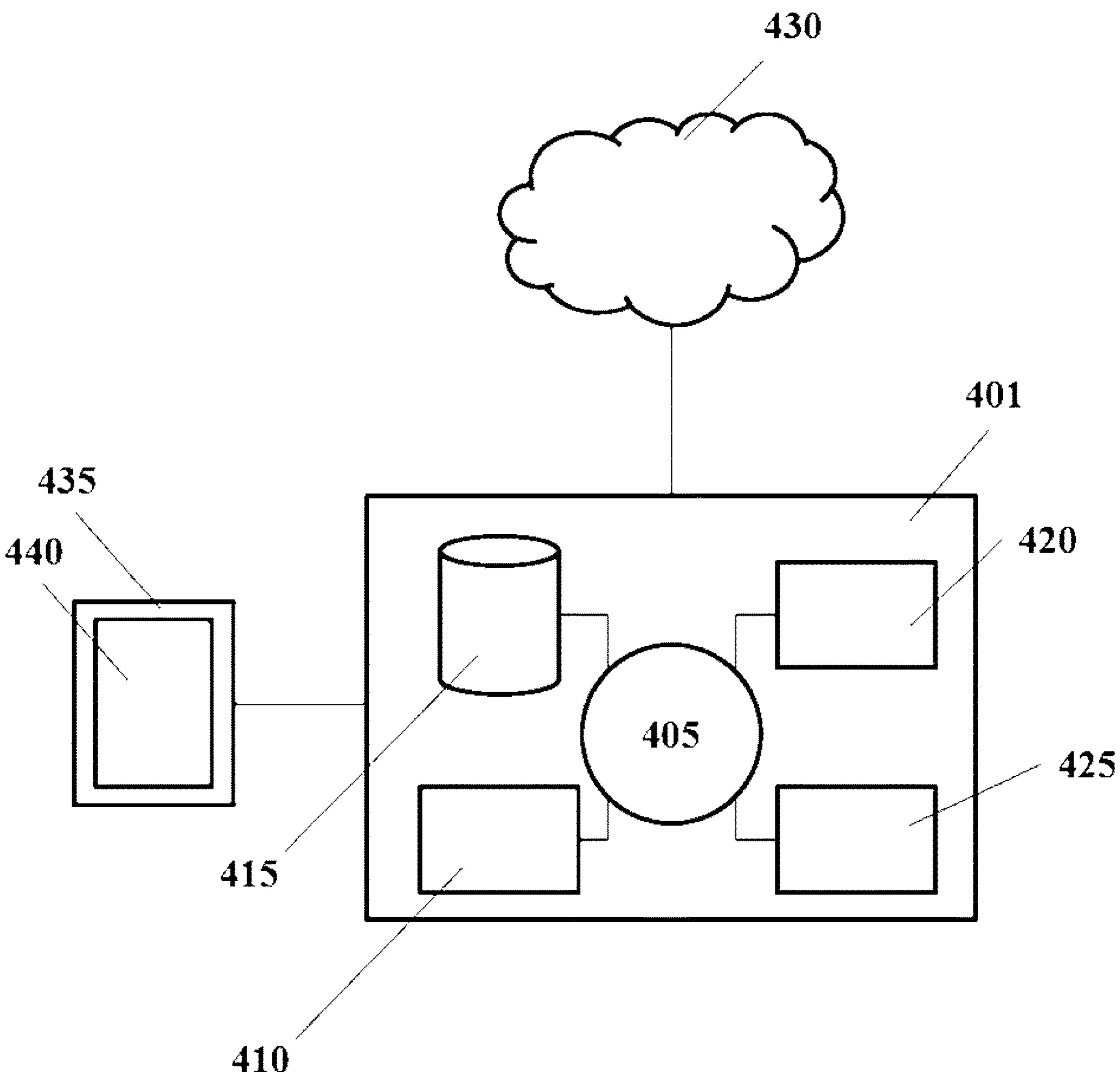
FIG. 4 shows a computer system that is programmed or otherwise configured to implement methods provided herein.

The present disclosure provides computer systems that are programmed to implement methods of the disclosure. FIG. 4 shows a computer system 401 that is programmed or otherwise configured to, for example, control one or more flows to a plurality of nucleic acid molecules or imaging of a detection area (e.g., a detection area comprising the plurality of nucleic acid molecules). The computer system 401 can regulate various aspects of the nucleic acid identification methods of the present disclosure, such as, for example, reagent flows, temperatures, and imaging parameters. The computer system 401 can be an electronic device of a user or a computer system that is remotely located with respect to the electronic device. The electronic device can be a mobile electronic device.

The computer system 401 includes a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. The instructions can be directed to the CPU 405, which can subsequently program or otherwise configure the CPU 405 to implement methods of the present disclosure. Examples of operations performed by the CPU 405 can include fetch, decode, execute, and writeback.

The CPU 405 can be part of a circuit, such as an integrated circuit. One or more other components of the system 401 can be included in the circuit. In some cases, the circuit is an application specific integrated circuit (ASIC).

The storage unit 415 can store files, such as drivers, libraries and saved programs. The storage unit 415 can store user data, e.g., user preferences and user programs. The computer system 401 in some cases can include one or more additional data storage units that are external to the computer system 401, such as located on a remote server that is in communication with the computer system 401 through an intranet or the Internet.

The computer system 401 can communicate with one or more remote computer systems through the network 430. For instance, the computer system 401 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface (UI) 440 for providing, for example, input regarding flow and imaging parameters. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 405. The algorithm can, for example, control the flow of various reaction mixtures to a support including a plurality of nucleic acid molecules thereon.

EXAMPLES

Example 1: Controlling the Extent of Incorporation of Dye-Labeled Nucleotides The extent of incorporation of dye-labeled nucleotides may be controlled by varying parameters such as ion concentrations and ratios thereof, nucleotide concentrations, and time.

Figure 2A:
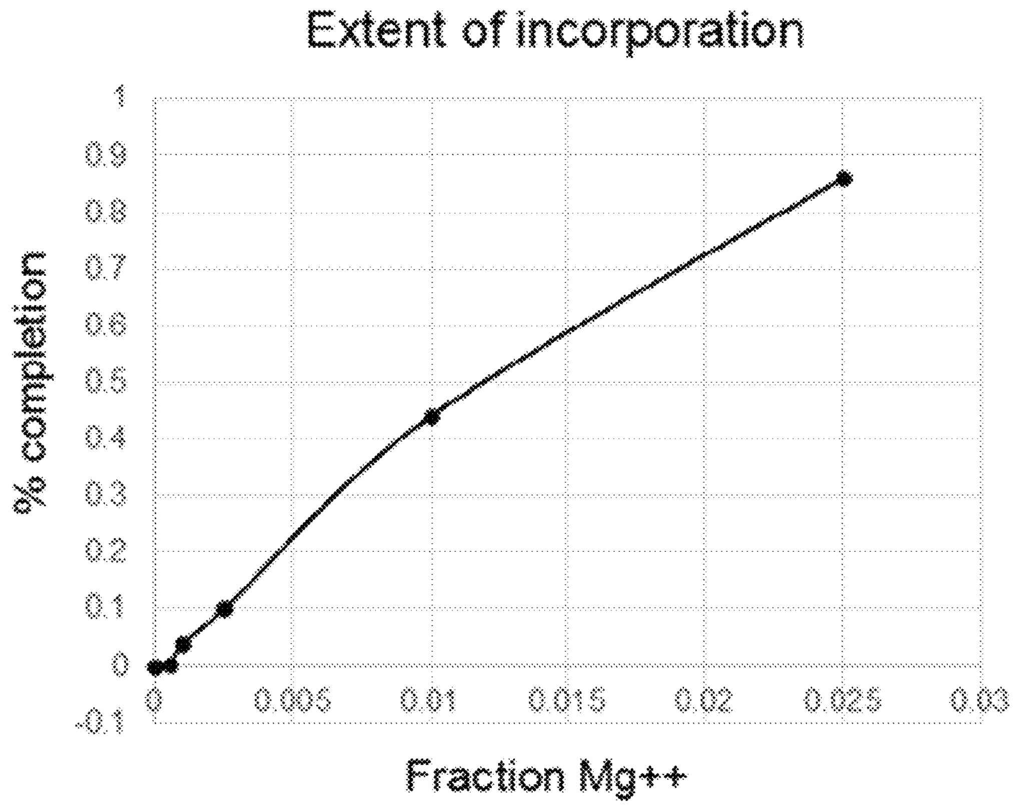

Template-hybridized primers were brought in contact with a reaction mixture comprising 100 nanoMolar (nM) dGTP-16-Cy5 for 30 seconds. A Therminator DNA polymerase was used to extend the primer at various fractions of Mg++ in Sr++. The total concentration of divalent metal ions was 2 mM. The extent of reaction was assessed using a flow cytometer. As shown in FIG. 2A, the extent of reaction was effectively varied in a controlled manner. Accordingly, the extent of an incorporation reaction may be controlled by adjustment of the ratio of metal ions (e.g., Mg++, Mn++, Sr++, etc.) at a constant time.

Figure 2B:
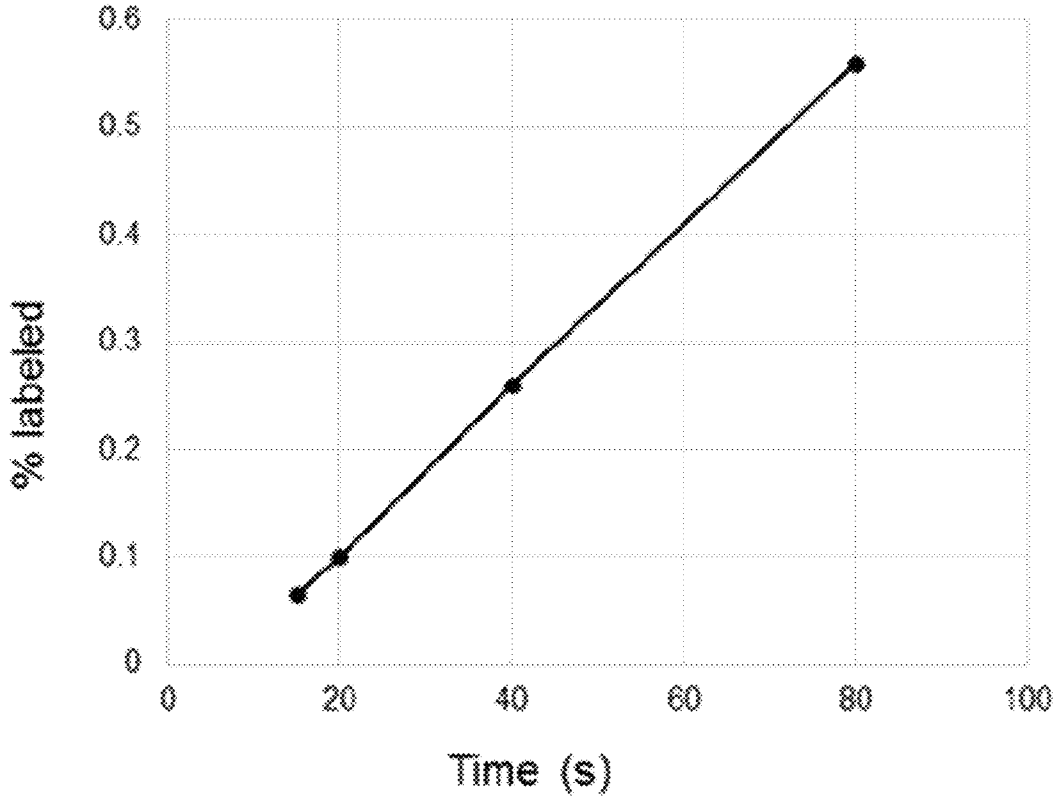
FIG. 2B shows the extent of incorporation of a given nucleotide at various extension times.

The extent of incorporation of a labeled nucleotide may also be controlled by varying the time permitted for extension. Template-hybridized primers were brought in contact with a reaction mixture comprising 100 nM dGTP-16-Cy5 for various durations. A Therminator DNA polymerase was used to extend the primer at Mg++/Sr++ concentrations of 0.05/1.95 mM (Mg++ fraction=0.025). The reaction was stopped with EDTA at different time points and the extent of labeling was assessed. As shown in FIG. 2B, the extent of reaction was effectively varied in a controlled manner. Accordingly, the extent of an incorporation reaction may be controlled by adjustment of the extension time.

Example 2: Three Flow Single Color Imaging Method

A three flow, single color imaging method was performed. Nucleotides were reversibly terminated with 3'-azidomethyl blocking groups. The fluorescent dye Cy5 was attached to nucleotides via a disulfide linker. Structures of the labeled nucleotides including 3'-azidomethyl blocking groups are included below:

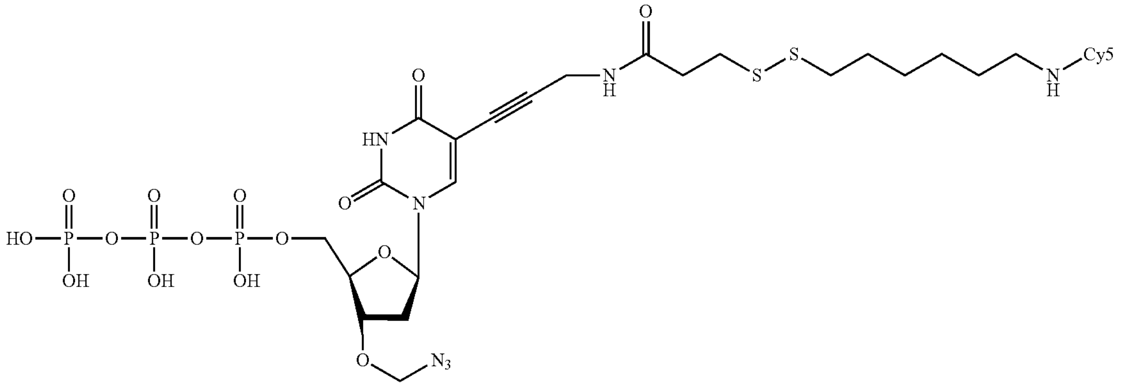

bdUTP-SS-Cy5

-continued

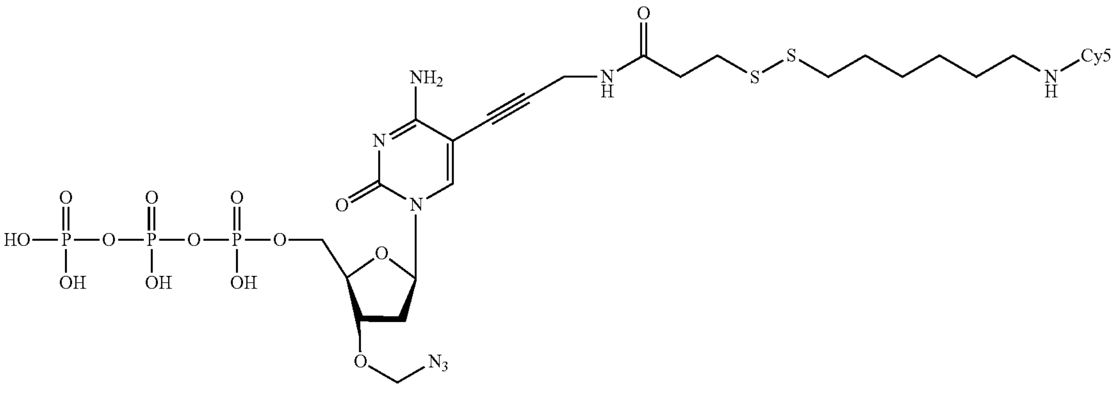

bdCTP-SS-Cy5

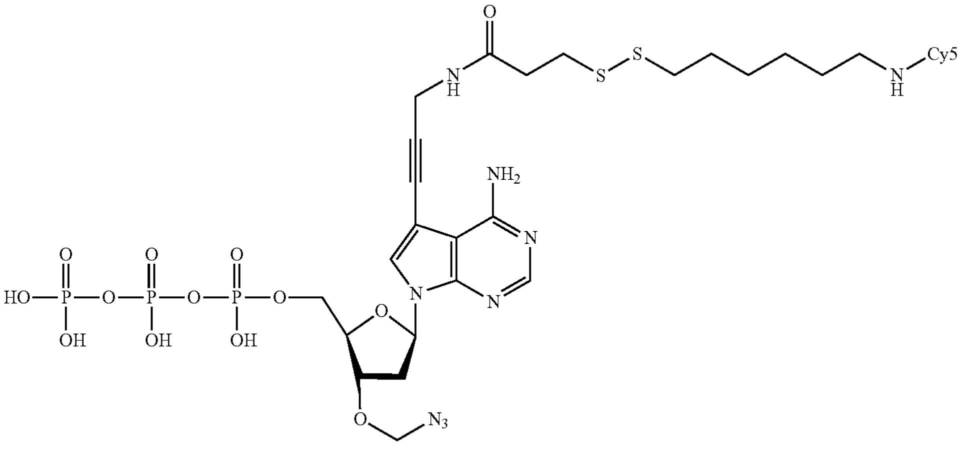

bdATP-SS-Cy5

A set of reaction mixtures including (i) reversibly terminated and labeled adenine- and cytosine-containing nucleotides at 25 nM each; (ii) reversibly terminated and labeled adenine- and uracil-containing nucleotides at 25 and 15 nM, respectively; (iii) reversibly terminated and unlabeled adenine-, cytosine-, uracil-, and guanine-containing nucleotides; and (iv) THP (10 mM) cleavage solution in Tris pH 8.8 were prepared.

Magnetic streptavidin beads with biotinylated template and annealed primer were affixed to an aminosilane flow cell. The template-hybridized primers were brought in contact with reaction mixtures (i), (ii), and (iii) sequentially for about 20 seconds each. Strontium ions were not included as nucleotides incorporated very slowly in the presence of magnesium ions alone. A set of four 3'-azidomethyl-dNTPs (the 3'-azidomethyl-dGTP analog is shown below), was used to extend the unextended primer/templates. The duration of cleavage with reaction mixture (iv) was 3 minutes.

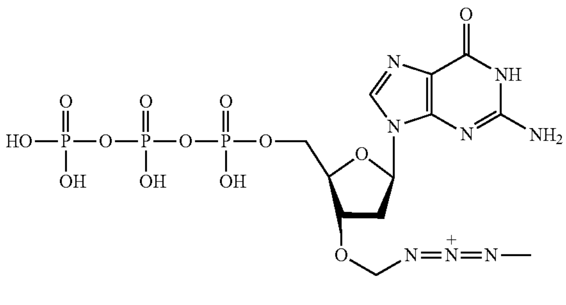

The cycle included (1) a first flow of reaction mixture (i) including labeled adenine- and cytosine-containing nucleotides, (2) washing and imaging, (3) a second flow of reaction mixture (ii) including labeled adenine- and uracil-containing nucleotides, (4) washing and imaging, (5) a third flow of reaction mixture (iii) including unlabeled ("dark") nucleotides, (6) cleavage of dyes and reversible terminators, and (7) washing and imaging. Signals obtained after the second flow, (3), were subtracted from the signal obtained after the first flow, (1), to give the second flow signals. The data were interpreted as follows: initial signal following the first flow and no signal following the second flow indicates that a cytosine-containing nucleotide was incorporated (i.e., signal of 1,0); signal following the first flow and signal following the second flow indicates that a adenine-containing nucleotide was incorporated (i.e., signal of 1,1); no initial signal following the first flow and signal following the second flow indicates that a uracil-containing nucleotide was incorporated (i.e., 0,1); and no signal following either flow indicates that a guanine-containing nucleotide was incorporated (i.e., 0,0).

Figure 3:
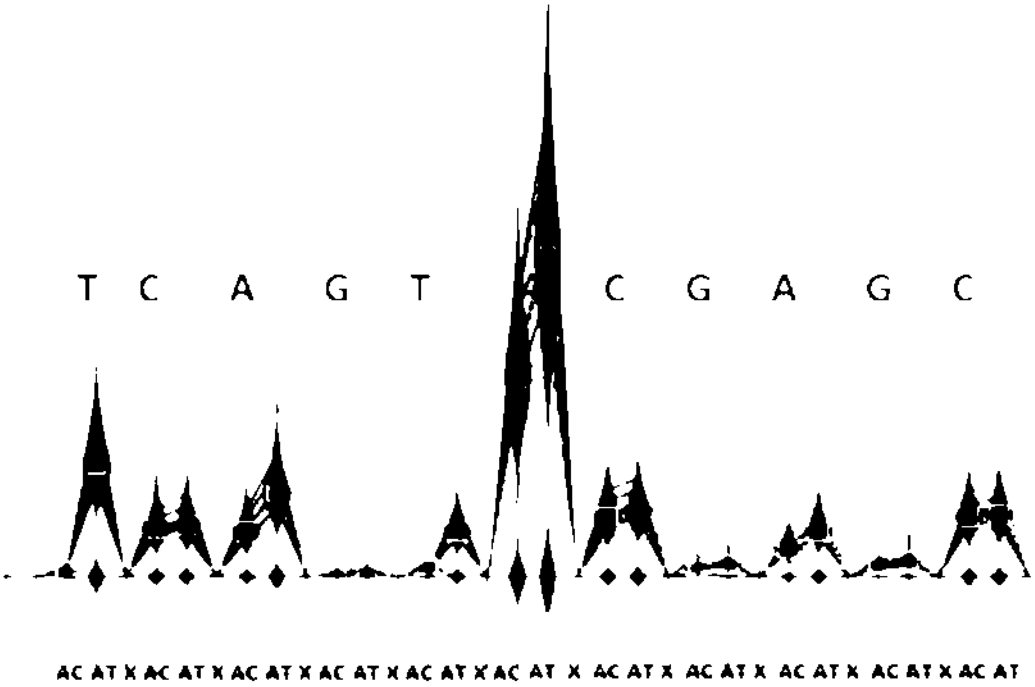
FIG. 3 shows sequencing signals corresponding to a multi-flow monochrome imaging method. Figure discloses SEQ ID NO: 1.

FIG. 3 shows sequencing results corresponding to the three-flow, two-image, single-color method. Shown in the black "onions" are the array of signal values for the beads; the mean signal is shown in the red crosses and the green square depicts the standard deviation. The true sequence is TCAGTACGAGC (SEQ ID NO: 1); the digital signature for each flow is shown. As shown in FIG. 3, the correct sequence could be read by interpreting the signals after the cycle of flows. For example, for the sequence to read T, the first flow of AC should give a signal of zero, the second flow of AT should give a signal of one. For the sequence to read C, the first flow of AC should give a signal of one, the second flow of AC should give a (subtracted) signal of zero. For the sequence to read G, the first and the second flows should give signals of zero. For the sequence to read A, the first flow should give a signal of one, and the second flow should give a (subtracted) signal of one.

Example 3: Phasing in Multiple Flow Experiments

A multiple flow experiment was performed. Three different template nucleic acid molecule populations (TF3, TF5, and TF6), each having different nucleic acid sequences, are immobilized to a detection area (e.g., as described herein).

The templates were interrogated with several different flow protocols (protocols A-D). Protocol D used a single flow of different canonical bases according to the sequence T-A-C-G. In this protocol, a T flow indicates that a first reaction mixture (e.g., flow) comprising a plurality of nucleotides comprising a T-base were flowed. A small percentage (2.5%) of the nucleotides of the first reaction mixture are labeled. A second reaction mixture comprising a plurality of nucleotides comprising a C-base (2.5% labeled) was then flowed. A third reaction mixture comprising a plurality of nucleotides comprising an A-base (2.5% labeled) was then flowed. Finally, a fourth reaction mixture comprising a plurality of nucleotides comprising a G-base (2.5% labeled) was flowed. Washing, cleaving, and imaging were performed consistently between reaction mixture flows (e.g., as described herein). Flowing of the first through fourth reaction mixtures, as well as associated washing, cleaving, and imaging, makes up a single flow cycle. At least 32 flow cycles were run where each cycle included a T-A-C-G flow sequence.

Protocols A-C used multiple flows of different canonical bases according to the sequence T-T-A-A-C-C-G-G. In each of these protocols, a T flow indicates that a first reaction mixture (e.g., flow) comprising a plurality of nucleotides comprising a T-base are flowed. A small percentage (2.5%) of the nucleotides of the first reaction mixture were labeled. Subsequently, a second reaction mixture comprising the same composition (e.g., 2.5% labeled T-containing nucleotides and 97.5% unlabeled T-containing nucleotides) was provided. Imaging to detect incorporations of T-containing nucleotides was performed after the first and/or second flows. A third reaction mixture comprising a plurality of nucleotides comprising an A-base (2.5% labeled) was then flowed, following by a fourth reaction mixture that had the same composition as the third reaction mixture. A fifth reaction mixture comprising a plurality of nucleotides comprising a C-base (2.5% labeled) was then flowed, followed by a sixth reaction mixture that had the same composition as the fifth reaction mixture. A seventh reaction mixture comprising a plurality of nucleotides comprising a G-base (2.5% labeled) was then flowed, followed by an eighth reaction mixture that had the same composition as the seventh reaction mixture. Washing, cleaving, and imaging were performed consistently between reaction mixture flows (e.g., as described herein). Flowing of the first through eighth reaction mixtures, as well as associated washing, cleaving, and imaging, makes up a single flow cycle. At least 32 flow cycles were run for protocols A and B, where each cycle included a T-T-A-A-C-C-G-G flow sequence. At least 33 flow cycles were run for protocol C, where each cycle included a T-T-A-A-C-C-G-G flow sequence.

Table 2 summarizes the local phasing (%) after 32 cycles for the three different template sequences.

TABLE 2

Local phasing after 32 cycles for different template sequences.

| | | Local phasing (%) | | |
|---|---|---|---|---|
| Protocol | Flow sequence | TF3 | TF5 | TF6 |
| A | T-T-A-A-C-C-G-G | 40 | 39 | 40 |
| B | T-T-A-A-C-C-G-G | 40 | 43 | 43 |
| C | T-T-A-A-C-C-G-G | 42 | 42 | 45 |
| D | T-C-A-G | 70 | 71 | 99 |

As shown in Table 2, accumulated phasing was significantly higher for Protocol D in which each canonical nucleotide is flowed a single time per cycle. Accumulated phasing was lower for Protocols A-C in which each canonical nucleotide is flowed twice per cycle.

FIGS. 7A-7D show the normalized signals detected by imaging by flow (upper panel) and the % phasing by flow (lower panel) for protocols A (FIG. 7A), B (FIG. 7B), C (FIG. 7A), and D (FIG. 7D), respectively, against template TF5. The vertical axis in the upper panel maps normalized medium signal strength for each nucleotide incorporated. The vertical axis in the lower panel maps normalized medium signal strength of each challenging flow (e.g., nucleotides in flow not expected to be incorporated). The horizontal axis for each of the upper and lower panel maps the flow sequence. For the flow sequence including double flows of the same nucleotide type, signals were only measured for one of the duplicate flows. In the upper panels, incorporations of a given base are indicated with a peak. Dotted open circle symbols correspond to A-containing nucleotides, empty open circle symbols correspond to T-containing nucleotides, solid dot symbols correspond to G-containing nucleotides, and right-to-left hashed symbols correspond to C-containing nucleotides. Left-to-right hashed symbols at or near 0 on the vertical axis indicate that a nucleotide from a given flow was not expected to be incorporated (e.g., a challenge flow). Dashed lines connect consecutive symbols (data points) to guide the eye, while a least squares fit is shown as a solid line. The fitting parameters corresponding to each figure are included in Table 3 below. In the lower panels, each symbol corresponds to a flow in the upper panel in which a nucleotide was not expected to be incorporated. The nucleotide identity of a challenge flow (e.g., represented by a circle filled with left-to-right hashed symbol) in the upper panel could be determined by the corresponding flow sequence from the lower panel. For example, in FIG. 7A, fluorescent signals were observed for the first challenge flow at flow sequence 37 (also known as flow position), which had a normalized medium signal around 0.2. This challenge flow was determined to be a T flow, as represented by the first dashed peak at the same flow sequence/position in the lower panel. As in the upper panels, dotted lines connect consecutive symbols to guide the eye while the solid gray line corresponds to a phase model where parameters such as phase lag, phase lead and phase droop were fitted to best correlate the observed signals (including signals from challenge flows).

Local phasing in challenge flow f, base b is a ratio of a challenge flow (e.g., nucleotides in flow not expected to be incorporated) signal to the previous and next incorporation signals in that base and is given as: localphasing $$(f, b) = \frac{2 * \mathrm{Signal}(f)}{(nextInc(b) + prevInc(b))}.$$

A local phasing of 1 implies that a challenge flow (e.g., nucleotides in flow not expected to be incorporated) has as much signal as an incorporation, and the strands are completely out of phase.

TABLE 3

Fitting parameters corresponding to protocols A-D run against template TF5.

| Protocol | Lag (%) | Lead (%) | Droop (%) | Variation Explained (%) |
|---|---|---|---|---|
| A | 0.4 | 0.3 | 0.0 | 79% |
| B | 0.4 | 0.3 | −0.1 | 80% |
| C | 0.5 | 0.6 | 0.3 | 73% |
| D | 1.6 | 0.2 | −0.2 | 77% |

The fitting parameters in Table 3 provide an estimated measure of phasing observed in the data. The explained variation %, which was between 70-80% for each protocol fit, indicates how well the respective mathematical fits account for the variations of the data sets. As shown in Table 3, lag phasing was significantly enhanced for protocol D, in which each canonical nucleotide was flowed a single time per cycle, relative to the other protocols in which each canonical nucleotide was flowed consecutively twice per cycle. Droop corresponds to drop out of nucleic acid molecules from the sequencing experiment during the course of the experiment.

Table 4 below shows the base quality score for various templates (TF3, TF4, etc.) for different flow sequences. For example, Run No. 283 corresponds to a flow sequence of T-T-A-C-G (e.g., a single flow cycle includes first and second reaction mixtures each including T-containing nucleotides, a third reaction mixture including A-containing nucleotides, a fourth reaction mixture including C-containing nucleotides, and a fifth reaction mixture including G-containing nucleotides). Washing, cleaving of labels/linkers, and imaging between flows including different canonical nucleotides was performed as described elsewhere herein. Run No. 296 corresponds to a flow sequence of T-T-A-A-C-C-G-G, where labels were cleaved between consecutive same-base nucleotide flows, and a wash was performed between consecutive same-base nucleotide flows, as described elsewhere herein. Run No. 290 corresponds to a flow sequence of T-T-T-A-A-A-C-C-C-G-G-G, where each base type was flowed three times in consecution, where labels were cleaved between at least two consecutive same-base nucleotide flows, and a wash was performed between at least two consecutive same-base nucleotide flows. Run No. 291 corresponds to the flow sequence of Run No. 296, but no cleaving was performed between consecutive same-base nucleotide flows. Run No. 292 corresponds to the flow sequence of Run No. 296, but neither washing nor cleaving of labels was performed between flows including the same canonical nucleotides (e.g., between the first and second flows that both include T-containing nucleotides). For each run, each flow used reaction mixtures comprising a mixture of labeled and unlabeled nucleotides (e.g., for Run No. 296, the first flow used a reaction mixture comprising a mixture of labeled T-containing nucleotides and unlabeled T-containing nucleotides, the second flow used a reaction mixture comprising a mixture of labeled T-containing nucleotides and unlabeled T-containing nucleotides, the third flow used a reaction mixture comprising a mixture of labeled A-containing nucleotides and unlabeled A-containing nucleotides, the fourth flow used a reaction mixture comprising a mixture of labeled A-containing nucleotides and unlabeled A-containing nucleotides, and so on). The base quality (BQ) score was calculated as a function of base calling error probabilities (P), by the formula, $BQ=-10 \log_{10} P$, such that a BQ score of 30 is equivalent to the probability of an incorrect base call 1 in 1000 times (or P=0.001).

TABLE 4

Comparison of flow protocol performance

| | Run No. | | | | |
|---|---|---|---|---|---|
| | 283 | 296 | 290 | 291 | 292 |
| Flow sequence | T-T-A-C-G | T-T-A-A-C-C-G-G | T-T-T-A-A-A-C-C-C-G-G-G | T-T-A-A-C-C-G-G | T-T-A-A-C-C-G-G |
| Label cleaved between double flow? | Yes | Yes | Yes | No | No |

TABLE 4 -continued

| Comparison of flow protocol performance | | | | | | |
|---|---|---|---|---|---|---|
| | | Run No. | | | | |
| | | 283 | 296 | 290 | 291 | 292 |
| Wash between double flow? | | Yes | Yes | Yes | Yes | No |
| Base quality score of templates | TF3 | 20 | 22 | 22 | 19 | 18 |
| | TF4 | 7 | 11 | 10 | 11 | 8 |
| | TF1 | 8 | 12 | 15 | 13 | 10 |
| | TF6 | 8 | 12 | 12 | 11 | 9 |
| | TF5 | 10 | 13 | 13 | 13 | 12 |
| | PhiX | 8 | 11 | 13 | 12 | 9 |
| | TF4 (modified) | 13 | 16 | 17 | 15 | 11 |

As shown in Table 4, duplicative flows with two or more consecutive same-base nucleotide flows help improve base quality scores. Washing and cleaving between duplicative flows both help improve base quality scores.

Example 4: Phasing in Multiple Flow Experiments

A multiple flow experiment was performed. A population of template nucleic acid molecules having the same nucleic acid sequence was immobilized to a detection area (e.g., as described herein). The template nucleic acid molecules were interrogated with two different flow protocols, as summarized in Table 5 below. Protocol E used the flow sequence T*-T*-C*-C*-A*-A*-G*-G* and is alternately referred to as a "bright polish" protocol, while Protocol F used the flow sequence T*-T-C*-C-A*-A-G*-G and is alternately referred to as a "bright polish" protocol. In the preceding flow sequences, an asterisk is indicative of a reaction mixture including labeled nucleotides (e.g., 2.5% labeled nucleotides), while the absence of an asterisk is indicative of a reaction mixture including only unlabeled nucleotides. Labeled nucleotides are linked to fluorescent labels via disulfide linkers.

TABLE 5

| Comparison of bright and dark polish phasing. | | | |
|---|---|---|---|
| Protocol | Flow sequence | Overall lag rate | Overall lead rate |
| E | T*-T*-C*-C*-A*-A*-G*-G* | 0.75 | 0.57 |
| F | T*-T-C*-C-A*-A-G*-G | 0.43 | 0.55 |

As shown in Table 5, the "dark polish" protocol (e.g., protocol F) demonstrated lower phasing overall than the "bright polish" protocol.

In additional to reducing phasing issues, the use of a "dark polish" protocol (e.g., flowing a first reaction mixture including labeled nucleotides of a same canonical type and then a second reaction mixture including unlabeled nucleotides of the same canonical type) may provide further advantages over a "bright polish" protocol (e.g., flowing a first reaction mixture including labeled nucleotides of a same canonical type and then a second reaction mixture also including labeled nucleotides of the same canonical type). Unlabeled nucleotides can be purchased directly from a supplier or prepared according to established procedures using available reagents, where labeled nucleotides may be acquired at higher cost and require significantly more preparation. Labels of labeled nucleotides are often cleaved (e.g., as described herein) to reduce context issues in sequencing. Accordingly, the use of a reaction mixture including only unlabeled nucleotides can eliminate a need to use multiple different cleaving flows between different reaction mixtures and may also reduce washing flows, as well as reduce scarring effects. Concentrations of unlabeled nucleotides included in, e.g., a second or other subsequent reaction mixture may also be higher than concentrations of nucleotides (e.g., labeled and unlabeled nucleotides) included in a first reaction mixture. For example, the concentration of unlabeled (e.g., dark) nucleotides of a given same canonical type in a second reaction mixture (e.g., dark flow) may be more than 100% of the concentration of total nucleotides (labeled and unlabeled) of the given same canonical type in a first reaction mixture, such as at least about 110%, 120%, 125%, 130%, 140%, 150%, 160%, 170%, 180%, 190%, 200%, or higher. In some embodiments, a dark polish can have a concentration that is higher than that of a corresponding bright flow, ranging from about 150% to over 200%, including but not limited to 250%, 300%, up to 500% or even higher. In an example dark polish protocol having the flow sequence T*-T-A*-A-C*-C-G*-G, concentrations in the second reaction mixtures of the various canonical nucleotides (e.g., dark polish flows) were [T, A, C, G]=[200%, 200%, 200%, 154%].

A dark polish scheme may be applied to any flow sequence or protocol provided herein. In some cases, one or more dark flows may be used. For example, a flow sequence may comprise the use of a first reaction mixture comprising both labeled and unlabeled nucleotides of a given same canonical base type (for example, T), a second reaction mixture comprising only unlabeled nucleotides of the given same canonical base type, and a third reaction mixture comprising only unlabeled nucleotides of the given same canonical base type. Similarly, multiple bright flows may be used in combination with one or more dark flows. In another example, a flow sequence may comprise the use of a first reaction mixture comprising both labeled and unlabeled nucleotides of a given same canonical base type (for example, T, such as 2.5% labeled T-containing nucleotides and 97.5% unlabeled T-containing nucleotides), a second reaction mixture comprising both labeled and unlabeled nucleotides of the given same canonical base type in the same or different concentrations (for example, 2.5% labeled T-containing nucleotides and 97.5% unlabeled T-containing nucleotides, or a different amount of labeled T-containing nucleotides such as 1% T-containing nucleotides), and a third reaction mixture comprising only unlabeled nucleotides of the given same canonical base type.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for sequencing, comprising:

(a) providing a plurality of nucleic acid molecules, wherein said plurality of nucleic acid molecules has sequence identity with respect to one another;

(b) repeating, at least four times, the following steps:

(i) contacting said plurality of nucleic acid molecules with a first reaction solution comprising a first plurality of nucleotides at a first concentration, under conditions sufficient to incorporate said first plurality of nucleotides into a first plurality of growing strands of a first subset of said plurality of nucleic acid molecules by a first polymerase in a first primer extension reaction, wherein said first plurality of nucleotides comprises only one kind of identical purine or pyrimidine nucleotides and comprises labeled nucleotides that comprise a first detectable label;

(ii) subsequent to step (i), removing nucleotides of said first reaction solution that are not incorporated into the first plurality of growing strands of the first subset of said plurality of nucleic acid molecules by bringing a mixture formed in step (i) into contact with a first washing solution;

(iii) subsequent to step (ii), bringing a mixture formed in step (ii) into contact with a second reaction solution comprising a second plurality of nucleotides at a second concentration, under conditions sufficient to incorporate said second plurality of nucleotides into a second plurality of growing strands of a second subset of said plurality of nucleic acid molecules by a second polymerase in a second primer extension reaction, wherein said second concentration is higher than said first concentration, wherein said second plurality of nucleotides comprises only said one kind of identical purine or pyrimidine nucleotides and comprises only unlabeled nucleotides;

(iv) subsequent to step (iii), removing nucleotides of said second reaction solution that are not incorporated into the second plurality of growing strands of the second subset of said plurality of nucleic acid molecules by bringing a mixture formed in step (iii) into contact with a second washing solution; and (v) detecting one or more signals from said first detectable label in the mixture formed in step (ii) or a mixture formed in step (iv), wherein the one or more signals are indicative that said first plurality of nucleotides is incorporated into the first plurality of growing strands of the first subset of said plurality of nucleic acid molecules, wherein, when step (b) is repeated for at least four times, in each time of the at least four times, said one kind of identical purine or pyrimidine nucleotides in step (b) is different.

2. The method of claim 1, wherein said conditions sufficient to incorporate said first plurality of nucleotides into said first plurality of growing strands of said first subset of said plurality of nucleic acid molecules are different from said conditions sufficient to incorporate said second plurality of nucleotides into said second plurality of growing strands of said second subset of said plurality of nucleic acid molecules.

3. The method of claim 1, wherein said first plurality of nucleotides further comprises unlabeled nucleotides.

4. The method of claim 3, wherein the concentration of said unlabeled nucleotides of said first plurality of nucleotides is higher than the concentration of said labeled nucleotides of said first plurality of nucleotides.

5. The method of claim 1, wherein said first plurality of nucleotides or said second plurality of nucleotides is non-terminated nucleotides.

6. The method of claim 1, wherein said first plurality of nucleotides and said second plurality of nucleotides are non-terminated nucleotides.

7. The method of claim 1, wherein said plurality of nucleic acid molecules comprises a homopolymer sequence, wherein: (1) a subset of said first plurality of nucleotides is incorporated into nucleotide positions of a growing strand of said first plurality of growing strands of said first subset of said plurality of nucleic acid molecules which is complementary to said homopolymer sequence or (2) a subset of said second plurality of nucleotides is incorporated into nucleotide positions in a growing strand of said second plurality of growing strands of said second subset of said plurality of nucleic acid molecules which is complementary to said homopolymer sequence.

8. The method of claim 1, wherein said first plurality of growing strands and said second plurality of growing strands do not share a common growing strand.

9. The method of claim 1, wherein said first plurality of growing strands and said second plurality of growing strands share at least one common growing strand.

10. The method of claim 1, further comprising, subsequent to step (v), bringing a mixture formed in step (v) into contact with a cleaving solution to cleave the first detectable label from said first plurality of growing strands of said first subset of said plurality of nucleic acid molecules.

11. The method of claim 1, wherein nucleic acid molecules of at least a portion of said first subset of said plurality of nucleic acid molecules and nucleic acid molecules of at least a portion of said second subset of said plurality of nucleic acid molecules are identical.

12. The method of claim 1, further comprising, subsequent to step (iii), bringing said mixture formed in step (iii) into contact with a third reaction solution comprising a third plurality of nucleotides, under conditions sufficient to incorporate said third plurality of nucleotides into a third plurality of growing strands of a third subset of said plurality of nucleic acid molecules by a third polymerase in a third primer extension reaction, wherein said third plurality of nucleotides comprises only said one kind of identical purine or pyrimidine nucleotides.

13. The method of claim 1, further comprising, repeating steps (i)-(iv) using a third reaction solution instead of said first reaction solution, wherein said third reaction solution comprises a third plurality of nucleotides, wherein said third plurality of nucleotides comprises only another one kind of identical purine or pyrimidine nucleotides that is different from said one kind of identical purine or pyrimidine nucleotides and comprises labeled nucleotides that comprise a second detectable label, and using a fourth reaction solution instead of said second reaction solution, wherein said fourth reaction solution comprises a fourth plurality of nucleotides, wherein said fourth plurality of nucleotides comprises only said another one kind of identical purine or pyrimidine nucleotides and comprises only unlabeled nucleotides; and repeating step (v), wherein detecting one or more signals from said second detectable label in a mixture formed in the repeated step (ii) or a mixture formed in the repeated step (iv) indicates that said third plurality of nucleotides is incorporated into said plurality of nucleic acid molecules.

14. The method of claim 1, wherein step (iii) is performed prior to said detecting one or more signals from said first detectable label in said mixture formed in step (iv).

15. The method of claim 1, wherein said second concentration is at least about 10% higher than said first concentration.

16. The method of claim 1, wherein said second concentration is at least about 500% higher than said first concentration.

17. The method of claim 1, wherein said first plurality of nucleotides or said second plurality of nucleotides are reversibly terminated nucleotides.

* * * * *